US011325956B2

(12) United States Patent
Boye et al.

(10) Patent No.: US 11,325,956 B2
(45) **Date of Patent: *May 10, 2022**

(54) DUAL-AAV VECTOR-BASED SYSTEMS AND METHODS FOR DELIVERING OVERSIZED GENES TO MAMMALIAN CELLS

(71) Applicant: University of Florida Research Foundation, Incorporated, Gainesville, FL (US)

(72) Inventors: Sanford L. Boye, Gainesville, FL (US); Shannon E. Boye, Gainesville, FL (US); Frank Dyka, Gainesville, FL (US); William W. Hauswirth, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/265,864

(22) Filed: Feb. 1, 2019

(65) Prior Publication Data

US 2019/0153050 A1 May 23, 2019

Related U.S. Application Data

(60) Division of application No. 14/279,142, filed on May 15, 2014, now Pat. No. 10,214,572, which is a continuation of application No. PCT/US2012/065645, filed on Nov. 16, 2012.

(60) Provisional application No. 61/560,437, filed on Nov. 16, 2011.

(51) Int. Cl.

*C07K 14/47* (2006.01)
*A61K 48/00* (2006.01)
*C12N 15/86* (2006.01)

(52) U.S. Cl.

CPC .......... *C07K 14/47* (2013.01); *A61K 48/0066* (2013.01); *C12N 15/86* (2013.01); *C07K 14/4716* (2013.01); *C12N 2750/14143* (2013.01); *C12N 2800/40* (2013.01); *C12N 2830/50* (2013.01); *C12N 2840/445* (2013.01); *C12N 2999/007* (2013.01)

(58) Field of Classification Search

CPC ..... C07K 14/47; A61K 48/0066; C12N 15/86
USPC ...................................................... 435/320.1
See application file for complete search history.

(56) References Cited

U.S. PATENT DOCUMENTS 10,214,572 B2 2/2019 Boye et al.
2010/0003218 A1 1/2010 Duan et al.
2010/0266551 A1 10/2010 Richard et al.
2012/0003190 A1 1/2012 Yamoah et al.
2013/0210895 A1 8/2013 Boye et al.
2014/0249208 A1 9/2014 Bancel et al.
2014/0256802 A1 9/2014 Boye et al.
2018/0015172 A1 1/2018 Muzyczka et al.

(Continued)

FOREIGN PATENT DOCUMENTS

WO WO 2008/088895 A2 7/2008
WO WO 2014/170480 A1 10/2014

(Continued)

OTHER PUBLICATIONS

Duan et al. (Expanding AAV Packaging Capacity with Trans-splicing or Overlapping Vectors: A Quantitative Comparison; Molecular Therapy vol. 4, No. 4, pp. 383-391, Oct. 2001 (Year: 2001).*
Daya et al. (Gene Therapy Using Adeno-Associated Virus Vectors; Clinical Microbiology Reviews, vol. 21, No. 4, pp. 583-593, Oct. 2008 (Year: 2008).*

(Continued)

*Primary Examiner* — Antonio Galisteo Gonzalez
(74) *Attorney, Agent, or Firm* — Wolf, Greenfield & Sacks, P.C.

(57) ABSTRACT

Disclosed are materials and methods for treating diseases of the mammalian eye, and in particular, Usher syndrome 1B (USH1B). The invention provides AAV-based, dual-vector systems that facilitate the expression of full-length proteins whose coding sequences exceed that of the polynucleotide packaging capacity of an individual AAV vector. In one embodiment, vector systems are provided that include i) a first AAV vector polynucleotide that includes an inverted terminal repeat at each end of the polynucleotide and a suitable promoter followed by a partial coding sequence that encodes an N-terminal portion of a full-length polypeptide; and ii) a second AAV vector polynucleotide that includes an inverted terminal repeat at each end of the polynucleotide and a partial coding sequence that encodes a C-terminal portion of a full-length polypeptide, optionally followed by a polyadenylation (pA) signal sequence. In another embodiment, the vector system includes i) a first AAV vector polynucleotide comprising an inverted terminal repeat at each end, a suitable promoter followed by a partial coding sequence that encodes an N-terminal portion of a full-length polypeptide followed by a splice donor site and intron and ii) a second AAV vector polynucleotide comprising an inverted terminal repeat at each end, followed by an intron and a splice-acceptor site for the intron, followed by a partial coding sequence that encodes a C-terminal portion of a full-length polypeptide, optionally followed by a polyadenylation (pA) signal sequence. The coding sequence or the intron sequence in the first and second AAV vectors preferably includes a sequence region that overlaps.

11 Claims, 26 Drawing Sheets
(13 of 26 Drawing Sheet(s) Filed in Color)
Specification includes a Sequence Listing.

(56) References Cited

U.S. PATENT DOCUMENTS

| | | | |
|---|---|---|---|
| 2020/0157573 A1 | 5/2020 | Dyka et al. | |
| 2021/0130421 A1 | 5/2021 | Boye et al. | |

FOREIGN PATENT DOCUMENTS

| | | |
|---|---|---|
| WO | WO 2018/039375 A1 | 3/2018 |
| WO | WO 2018/162748 A1 | 9/2018 |
| WO | WO 2018/204734 A1 | 11/2018 |

OTHER PUBLICATIONS

Hashimoto et al. (Lentiviral gene replacement therapy of retinas in a mouse model for Usher syndrome type 1B; Gene Therapy, 14, 584-594, (2007) (Year: 2007).*

Human Myosin VIIA (Human myosin VIIA (USH1B) mRNA, complete cds; GenBank: U39226.1; http://www.ncbi.nlm.nih.gov/nuccore/U39226; pp. 1-5; available Jul. 11, 1996 (Year: 1996).*

Al-Hussaini et al.; Mature retinal pigment epithelium cells are retained in the cell cycle and proliferate in vivo; Molecular Vision 2008; 14:1784-1791 (Year: 2008).*

International Search Report and Written Opinion for International Application No. PCT/US2012/065645 dated Mar. 29, 2013.

International Preliminary Report on Patentability for International Application No. PCT/US2012/065645 dated May 30, 2014.

Allocca et al., Serotype-dependent packaging of large genes in adeno-associated viral vectors results in effective gene delivery in mice. J Clin Invest. May 1, 2008; 118(5): 1955-1964. Published online Apr. 15, 2008. doi: 10.1172/JCI34316.

Dong et al., Characterization of genome integrity for oversized recombinant AAV vector. Mol Ther. Jan. 2010;18(1):87-92. doi: 10.1038/mt.2009.258. Epub Nov. 10, 2009.

Duan et al., Circular intermediates of recombinant adeno-associated virus have defined structural characteristics responsible for long-term episomal persistence in muscle tissue. J Virol. Nov. 1998;72(11):8568-77.

Duan et al., Expanding AAV packaging capacity with trans-splicing or overlapping vectors: a quantitative comparison. Mol Ther. Oct. 2001;4(4):383-91.

GenBank Submission; NIH/NCBI, Accession No. U39226.1. Human myosin VIIA (USH1B) mRNA, complete cds. Jul. 11, 1996. 5 pages.

Hashimoto et al., Lentiviral gene replacement therapy of retinas in a mouse model for Usher syndrome type 1B. Gene Therapy. 2007:14;584-594.

Jacobson et al., Usher syndromes due to MYO7A, PCDH15, USH2A or GPR98 mutations share retinal disease mechanism. Hum Mol Genet. Aug. 1, 2008;17(15):2405-15. doi: 10.1093/hmg/ddn140. Epub May 7, 2008.

Lai et al., Evidence for the Failure of Adeno-associated Virus Serotype 5 to Package a Viral Genome ≥8.2 kb. Mol Ther. 2010; 18 1, 75-79. doi:10.1038/mt.2009.256.

Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.

Wu et al., Effect of genome size on AAV vector packaging. Mol Ther. Jan. 2010;18(1):80-6. doi: 10.1038/mt.2009.255. Epub Nov. 10, 2009.

Yan et al., Inverted terminal repeat sequences are important for intermolecular recombination and circularization of adeno-associated virus genomes. J Virol. Jan. 2005;79(1):364-79.

International Preliminary Report on Patentability dated Nov. 14, 2019 for Application No. PCT/US2018/031009.

International Search Report and Written Opinion dated Jul. 30, 2018 for Application No. PCT/US2018/031009.

International Search Report and Written Opinion dated Feb. 20, 2020 for Application No. PCT/US2019/059549.

Akil et al., Dual AAV-mediated gene therapy restores hearing in a DFNB9 mouse model. Proc Natl Acad Sci U S A. Mar. 5, 2019;116(10):4496-4501. doi: 10.1073/pnas.1817537116. Epub Feb. 19, 2019.

Ghosh et al., A hybrid vector system expands adeno-associated viral vector packaging capacity in a transgene-independent manner, Mol Ther, Jan. 2008;16(1):124-30. doi: 10.1038/sj.mt.6300322. Epub Nov. 6, 2007.

Extended European Search Report for European Application No. EP 18793935.0 dated Feb. 22, 2021.

International Preliminary Report on Patentability for Application No. EP 18793935.0 dated Feb. 22, 2021.

Alemi et al., Progress Report: AOS Research Grant: Restoration of Hearing in the Otoferlin Knockup Mouse using Viral Gene Therapy. 145th Annual Meeting. American Otological Society, Inc. Apr. 21-22, 2012; p. 68. Available online at: https://www.americanontologicalsociety.org/assets/2012.pdf.

Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.

Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.

* cited by examiner

1 - SIZE MARKER
2 - pTR-smCBA-hMyo7a PLASMID TRANSFECTION
3 - "HETEROGENEOUS" Myo7a
4 - DUAL VECTOR SYSTEM 1 AAV2 N´+C´
5 - DUAL VECTOR SYSTEM 1 AAV2 (TRIPLE) N´+C´
6 - DUAL VECTOR SYSTEM 1 AAV2 (TRIPLE) N´ ONLY
7 - DUAL VECTOR SYSTEM 2 INTRON 23 AAV2 (TRIPLE) N´+C´
8 - DUAL VECTOR SYSTEM 2 INTRON 23 AAV2 (TRIPLE) N´ ONLY
9 - DUAL VECTOR SYSTEM 3 SYNTHETIC INTRON AAV2 (TRIPLE) N´+C´
10 - DUAL VECTOR SYSTEM 3 SYNTHETIC INTRON AAV2 (TRIPLE) N´ ONLY

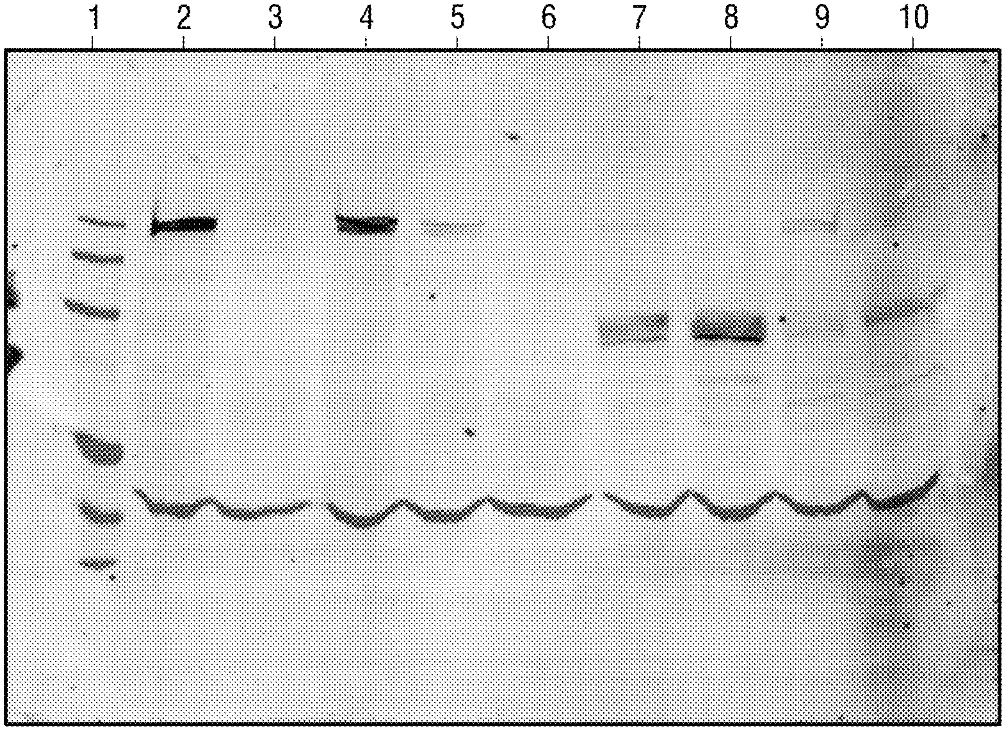

FIG. 5

| | # OF CLONES SEQUENCED | % CORRECT |
|---|---|---|
| AP HYBRID | 10 | 100% |
| TRANS-SPLICING | 10 | 100% |
| SIMPLE OVERLAP | 10 | 100% |

DUAL-AAV VECTOR-BASED SYSTEMS AND METHODS FOR DELIVERING OVERSIZED GENES TO MAMMALIAN CELLS

CROSS-REFERENCE TO RELATED APPLICATIONS

The present application is a divisional of U.S. application Ser. No. 14/279,142, now U.S. Pat. No. 10,214,572, filed May 15, 2014, which is a continuation of PCT Inti. Patent Appl. No. PCT/US2012/065645 filed Nov. 16, 2012, which claimed priority to U.S. Provisional Patent Appl. No. 61/560,437, filed Nov. 16, 2011; the contents of each of which is hereby incorporated in its entirety by express reference thereto. REFERENCE TO A SEOUENCE LISTING SUBMITTED AS A TEXT FILE VIA EFS-WEB RELATED APPLICATIONS The present application contains a Sequence Listing which has been submitted in ASCII format via EFS-Web and is hereby incorporated by reference in its entirety. Said ASCII copy, created on Feb. 1, 2019, is named U119670022US02-SEQ-EPG and is 102,739 bytes in size.

STATEMENT REGARDING FEDERALLY SPONSORED RESEARCH OR DEVELOPMENT

This invention was made with government support under grant number EY021721 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The present invention relates generally to the fields of molecular biology and virology, and in particular, to the development of gene delivery vehicles. Disclosed are improved rAAV dual-vector systems, and compositions useful in delivering a variety of nucleic acid segments, including those encoding therapeutic proteins polypeptides, peptides, antisense oligonucleotides, or ribozyme constructs to selected host cells for use in various gene-therapy regimens. Methods are also provided for preparing and using these modified rAAV-dual-vector based systems in a variety of viral-based gene therapies, and in particular, for the treatment and/or amelioration of symptoms of Myosin VII-deficiency, including, without limitation, the treatment of human Usher syndrome.

Description of Related Art

As has been established by a multitude of successful proof-of-concept studies, and various clinical trials, recombinant AAV has emerged as the most optimal gene delivery vehicle to treat retinal disease. However, one limitation of AAV is its relatively small DNA packaging capacity—approximately 4.7 kilobases (KB). Thus, standard AAV vector systems are unsuitable for addressing diseases in which large genes are mutated or otherwise dysfunctional. An example of such a disease is Usher syndrome.

The most common form of Usher syndrome, USH1B, is a severe autosomal-recessive, deaf-blindness disorder caused by mutations in the myosin VIIa gene. Blindness occurs from a progressive retinal degeneration that begins after deafness, and after development of the retina. MYO7a protein is expressed in photoreceptors and retinal pigment epithelium (RPE), and is involved in opsin transport through photoreceptor cilia and the movement of RPE melanosomes.

The coding region for the human Myosin VII protein (MYO7a), however, is 6534 or 6648 nucleotides in length (depending on the allelic variant), making traditional AAV vector systems unsuitable for gene therapy of USH1B.

Previously, Allocca et al. (2008) published intriguing results suggesting that AAV5 serotype vectors were capable of packaging genomes of up to 8.9 KB in size, and that these vectors expressed full-length proteins when delivered in vivo. In this study, the authors expressed full-length MYO7A protein from an AAV5 vector containing the CMV promoter driving hMyo7a. Subsequent studies, carried out to directly validate the Allocca et al. findings were simultaneously published by three independent groups (Lai et al., 2010; Dong et al., 2010; Wu et al., 2010), and their publication was accompanied by an expert commentary (See, Hirsch et al., 2010). While all three studies confirmed that these 'oversized' AAV5 vectors did indeed drive full-length protein expression, the genetic content of each vector capsid was found to be limited only to ~5 KB of DNA, and not the 8.7 KB originally reported by Allocca et al. (2008). These vector capsids were shown to contain a "heterogeneous mixture" of truncated vector genomes (e.g., the 5'-end of the gene, the 3'-end of the gene, or a mixture of the two, with an internal sequence deletion) (Lai et al., 2010; Dong et al., 2010; Wu et al., 2010). Additionally, these oversized/heterogeneous vectors exhibited poor packaging efficiency (i.e., low-vector titers) and low transduction efficiency when compared to matched reporter vectors of standard size (<5 KB) (Wu et al., 2010).

Using this 'heterogeneous' system, vectors containing portions of the MYO7A transgene were packaged, however, and proof-of-concept results were demonstrated in the shaker-1 mouse model of USH1B. The therapeutic results achieved with the heterogeneous AAV-hMyo7a vectors were comparable to previous gene replacement results using a Lentivirus-based hMyo7a vector (Hashimoto et al., 2007).

This Lentivirus-Myo7a vector is under development by Oxford BioMedica in collaboration with Sanofi-Aventis for a phase I/II clinical trial of USH1B, marketed under the name UshStat® LentiVector®. Lentivirus is regarded as a vector platform that is not well-suited for infecting post-mitotic (i.e., non-dividing) cells. Furthermore, although the vector is suitable for transducing RPE, many studies have shown it to be ineffective at transducing adult photoreceptors. Even though MYO7A is expressed in both cell types, UshStat® may only be effective at rescuing the RPE phenotype. A study showed that PRs are actually the initial site of disease, so not targeting this cell type effectively may result in zero therapy, although it remains to be seen in the human clinical trial.

Because of the excellent safety profile and encouraging reports of efficacy in the AAV gene therapy trials for LCA2/RPE65, there has been continuing interest in creating an AAV-based system for treating USH1B patients. However, the current AAV vector for MYO7A, as previously mentioned, is heterogeneous; it is manufactured and purified as a single-virus preparation containing a mixture of viral payloads. This fact, unfortunately, makes it virtually impossible to characterize the vector fully—a requirement for government regulatory review and approval. In order to address this concern directly (i.e., that the vector genome of any AAV-based vectors for USH1B must be fully characterized before gaining Food and Drug Administration (FDA) approval, the inventors have developed an AAV dual-vector-based system to facilitate gene therapy approaches for treating USH1B.

BRIEF SUMMARY OF THE INVENTION

The subject invention concerns materials and methods for gene therapy of diseases, such as Usher syndrome 1B (USH1B). The inventors have characterized dual vector platforms described herein as to transcript fidelity, and have shown and that mRNA arising from the system is 100% accurate relative to what would be predicted by correct homologous recombination on the front and back vector pairs, making them useful as gene therapy delivery vector systems.

One aspect of the invention concerns a dual AAV vector system that permits expression of full-length proteins, whose coding sequence exceeds the polynucleotide packaging capacity of an individual AAV vector.

In one embodiment, a vector system of the invention comprises:

(i) a first AAV vector polynucleotide comprising an inverted terminal repeat at each end of the polynucleotide, and a suitable promoter followed by a partial coding sequence that encodes an N-terminal part of a selected full-length polypeptide; and (ii) a second AAV vector polynucleotide comprising an inverted terminal repeat at each end of the polynucleotide, and a partial coding sequence that encodes a C-terminal part of the selected full-length polypeptide, optionally followed by a polyadenylation (pA) signal sequence.

The coding sequence in the first and second AAV vectors comprises sequence that overlaps, such that part of the coding sequence present at the 3'-end of the coding sequence of the first vector is identical or substantially identical with part of the coding sequence present at the 5'-end of the coding sequence of the second vector. In an illustrative embodiment, the polypeptide encoded is a wild type or biologically-functional human myosin VIIa polypeptide (hmyo7a).

In another embodiment, a vector system of the invention includes:

(i) a first AAV vector polynucleotide comprising an inverted terminal repeat at each end, a suitable promoter followed by a partial coding sequence that encodes an N-terminal part of a selected full-length polypeptide followed by a splice donor site for an intron and an intron; and (ii) a second AAV vector polynucleotide comprising an inverted terminal repeat at each end, followed by an intron and a splice acceptor site for the intron, followed by a partial coding sequence that encodes a C-terminal part of the selected full-length polypeptide, optionally followed by a polyadenylation (pA) signal sequence.

The intron sequence in the first and second AAV vectors includes a sequence that overlaps, such that all or part of the intron sequence present at the 3'-end of the coding sequence of the first vector is identical, or substantially identical, with all or part of the intron sequence present at the 5'-end of the coding sequence of the second vector. In one embodiment, the intron is intron 23 of the hmyo7a gene. In a specific embodiment, the polypeptide encoded is a wild type (i.e., functional) human myosin VIIa polypeptide, and the intron is the full intron 23 of the hmyo7a gene.

BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The invention may be better understood by reference to the following description taken in conjunction with the accompanying drawings, in which like reference numerals identify like elements, and in which:

FIG. 5 shows an immunoblot to detect the presence of MYO7A in infected or transfected HEK293 cells. Heterogeneous vectors (described in introduction) are compared to all three dual-vector systems. Dual vectors were packaged either in AAV2 or in AAV2 (triple mutant) capsids. The triple mutant contains three tyrosine-to-phenylalanine mutations on the capsid surface. For all three dual-vector systems, infections were performed with either a) the front-half (N-terminal) and back-half (C-terminal) vectors; or b) the front-half vectors alone (to confirm the presence or absence of a truncated protein product expressed from the promoter-containing N-terminal vectors);

FIG. 10A is a diagram of the viral vector encoding human MYO7A cDNA. FIG. 10B is a western blot of WT eyecup (lane 1), primary RPE cultures derived from Myo7a-null mice and infected with AAV2-MYO7A (lane 2) or AAV5-MYO7A (lane 3), or not infected (lane 4), and primary RPE cultures derived from Myo7a$^{+/-}$ mice (lane 5). All lanes were immunolabeled with antibodies against actin (as a loading indicator of relative protein loading) and MYO7A. FIG. 10C, FIG. 10D, FIG. 10E, and FIG. 10F are immunofluorescence images of primary RPE cell cultures. Cells derived from Myo7a-null mice that were not infected (FIG. 10C), from Myo7a$^{+/-}$ mice (FIG. 10D), or from Myo7a-null mice infected with either 1×AAV2-MYO7A (FIG. 10E) or 1×AAV5-MYO7A (FIG. 10F). Scale=10 μm;

FIG. 11A, FIG. 11B, FIG. 11C, FIG. 11D, FIG. 11E, FIG. 11F, FIG. 11F-1, FIG. 11G, FIG. 11G-1, FIG. 11H, FIG. 11I, FIG. 11J, FIG. 11K, FIG. 11L, and FIG. 11M show the expression of MYO7A from single AAV2 and AAV5 vectors in vivo. FIG. 11A, FIG. 11B, FIG. 11C, FIG. 11D, and FIG. 11E show EM images of MYO7A immunogold labelling of the connecting cilium and pericilium from rod photoreceptors in a Myo7a-null retina. FIG. 11A is a longitudinal section from an untreated Myo7a-null retina (background label only). FIG. 11B and FIG. 11C are longitudinal sections from Myo7a-null retinas treated with AAV2-MYO7A (FIG. 11B) or AAV5-MYO7A (FIG. 11C). Scale=50 nm. FIG. 11D and FIG. 11E are transverse sections of connecting cilia from rod photoreceptors in Myo7a-null retinas treated with AAV2-MYO7A (FIG. 11D) or AAV5-MYO7A (FIG. 11E). Scale=50 nm. FIG. 11F and FIG. 11G show EM images of RPE cells from Myo7a-null retinas treated with AAV2-MYO7A (FIG. 11F) or AAV5-MYO7A (FIG. 11G). Scale=500 nm. BM=Bruch's membrane, AP=apical processes. Areas indicated by rectangles are enlarged in FIG. 11F-1 and FIG. 11G-1 to show MYO7A immunogold labeling (indicated by circles). Scale=50 nm. FIG. 11H and FIG. 11I show EM image of a longitudinal section of the connecting cilium and pericilium from a rod (FIG. 11H) and a cone (FIG. 11I) photoreceptor in a Myo7a-null retina, treated with AAV2-MYO7A. The section was double-labeled with MYO7A (12-nm gold) and rod opsin (15-nm gold) antibodies. Rod outer segments were labeled with the opsin antibody, while cones were identified by lack of rod opsin labeling in their outer segments. The sections show just the base of the outer segments. Nearly all the label in the connecting cilium is MYO7A, even in the rod. Scale=50 nm. FIG. 11J, FIG. 11K, FIG. 11L, and FIG. 11M are bar graphs indicating MYO7A immunogold particle density in the rod photoreceptor cilium and pericilium (FIG. 11J and FIG. 11K) and in the RPE (FIG. 11L and FIG. 11M), following treatment with AAV2-MYO7A (FIG. 11J and FIG. 11L) or AAV5-MYO7A (FIG. 11K and FIG. 11M) of different concentrations. n=3 animals per condition. Bars indicate SEM;

FIG. 12E illustrates a region distant from injection site, where all RPE cells lacked melanosomes in their apical processes. Brackets on left side indicate RPE apical processes. Scale=25 μm. FIG. 12F is a diagram of an eyecup, indicating the relative locations of the images shown in FIG. 12A, FIG. 12B, FIG. 12C, FIG. 12D, and FIG. 12E. Arrow indicates the site of injection; ONH indicates the optic nerve head;

FIG. 14A-1, FIG. 14A-2, FIG. 14B, FIG. 14C, FIG. 14D, FIG. 14E, FIG. 14F, and FIG. 14G show the expression of MYO7A from the overlapping AAV2-MYO7A dual vectors. FIG. 14A-1 and FIG. 14A-2 illustrate a diagram of the overlapping AAV2-MYO7A dual vectors. The overlapping region contains 1365 bases. FIG. 14B is a Western blot of proteins from primary RPE cultures derived from Myo7a-null mice and not infected (lane 1), or infected with AAV2-MYO7A(dual) (lane 2); primary RPE cultures derived from Myo7a$^{+/-}$ mice (lane 3); WT eyecup (lane 4); HEK293A cells transfected with pTR-smCBA-MYO7A (lane 5). All lanes were immunolabeled with anti-MYO7A and anti-actin. FIG. 14C, FIG. 14D, FIG. 14E, and FIG. 14F show immunofluorescence of cultured RPE cells transduced with AAV2-MYO7A(dual). FIG. 14C, FIG. 14D, and FIG. 14E show primary RPE cultures derived from Myo7a-null mice and ARPE19 (FIG. 14F) cells. Scale=10 μm. FIG. 14G is a bar graph indicating the distribution of MYO7A immunogold particle density among RPE cells from retinas of Myo7a-null mice, injected with AAV2-MYO7A(dual). n=3 animals;

FIG. 15A is the results of light microscopy of a semi-thin section from a treated Myo7a-null mouse retina. The region shown is near the injection site. Arrows indicate melanosomes in the apical processes. White lines indicate cells that still show the Myo7a-null phenotype, with an absence of melanosomes in the apical processes. Scale=50 μm. FIG. 15B is a low-magnification immunoEM image of RPE from a retina treated with AAV2-MYO7A(dual). As in FIG. 15A, the white line indicated a region that still showed the Myo7a-null phenotype. Rectangle 'c', includes melanosomes in the apical region, indicating a corrected RPE cell. Scale=500 nm. FIG. 15C, FIG. 15D, and FIG. 15E show higher-magnification images of regions outlined by the rectangles shown in FIG. 15B. MYO7A immunogold particles were indicated by circles. Scale=50 nm. FIG. 15F is a bar graph illustrating MYO7A immunogold particle density measured in RPE cells from Myo7a-null retinas, WT retinas, or from Myo7a-null retinas treated with AAV2-MYO7A (dual) and determined to be corrected or not corrected by the location of their apical melanosomes. n=3 animals per condition. Bars indicate SEM. FIG. 15G is an immunoEM image of a rod photoreceptor cilium double-labeled with antibodies against MYO7A (small gold particles) and against rod opsin (large gold particles). MYO7A labeling is associated with the connecting cilium and periciliary membrane, indicating expression and correct localization of MYO7A. While this region is devoid of opsin labeling, which is restricted to the disk membranes, it is consistent with the wild type (WT) phenotype, thus indicating correction of the mutant phenotype. Scale=300 nm;

(FIG. 18A and FIG. 18C) 1:10, (FIG. 18B and FIG. 18D) 1:100. Scale=200 nm;

FIG. 22A is a fragmented vector (fAAV). FIG. 22B shows simple overlap: the 1365-bp shared between the two vectors is shaded gray. FIG. 22C is a trans-splicing vector. FIG. 22D shows an AP hybrid vector: the 270-bp element shared between the two vectors is marked with diagonal gradient shading (1/3 head as described by Ghosh et al., 2011). FIG. 22 shows the native intron hybrid vectors utilizing the natural intron 23 of MYO7A sharing a 250-bp overlapping sequence. 3'MYO7A is the 3'-portion of MYO7A; 5'MYO7A is the 5'-portion of MYO7A; AAV is adeno-associated virus; AP is alkaline phosphatase; intron=intron 23 of MYO7A; pA=polyadenylation signal; SA=splice-acceptor site; SD=splice-donor site; smCBA=cytomegalovirus immediate early/chicken β-actin chimeric promoter;

FIG. 23A shows HEK293 cells infected with AAV2(tripleY-F) at MOIs of 10,000, 2000, and 400 FIG. 23B is a time-course assay of MYO7A expressed in HEK293 cells. Cells were harvested 3-7 days after infection. In FIG. 23C, HEK293 cells were infected with AAV2 dual vectors; MOI=multiplicity of infection; T=HEK293 cells transfected with full-length MYO7A plasmid; U=untreated HEK293 cells;

BRIEF DESCRIPTION OF THE SEQUENCES

Figure 1:
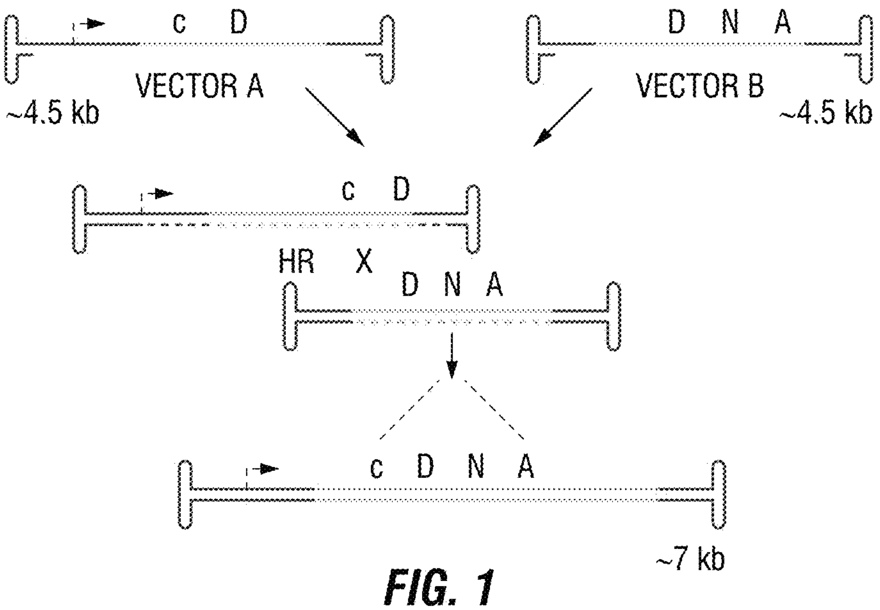
FIG. 1 shows the formation of complete gene cassette from dual AAV vectors via homologous recombination.

SEQ ID NO:1 is the nucleotide sequence of an "hMyo7a coding overlap vector A" of the subject invention;

SEQ ID NO:2 is the nucleotide sequence of an "hMyo7a coding overlap vector B" of the subject invention;

SEQ ID NO:3 is the nucleotide sequence of an "hMyo7a intron 23 splicing vector A" of the subject invention;

SEQ ID NO:4 is the nucleotide sequence of an "hMyo7a intron 23 splicing vector B" of the subject invention;

SEQ ID NO:5 is a nucleotide sequence encoding a human myosin VIIa polypeptide (protein coding sequence is nucleotides 273-6920);

SEQ ID NO:6 is the amino acid sequence of the human myosin VIIa polypeptide encoded by nucleotides 273-6920 of SEQ ID NO:5;

SEQ ID NO:7 is a nucleotide sequence that encodes a human myosin VIIa polypeptide;

SEQ ID NO:8 is an amino acid sequence of a human myosin VIIa polypeptide (isoform 2);

SEQ ID NO:9 is a synthetic oligonucleotide sequence, designated herein as P1, useful in accordance with one aspect of the present invention;

SEQ ID NO:10 is a synthetic oligonucleotide sequence, designated herein as P2, useful in accordance with one aspect of the present invention;

SEQ ID NO:11 is a synthetic oligonucleotide sequence, designated herein as P3, useful in accordance with one aspect of the present invention;

SEQ ID NO:12 is a synthetic oligonucleotide sequence, designated herein as P4, useful in accordance with one aspect of the present invention;

SEQ ID NO:13 is a synthetic oligonucleotide sequence, designated herein as P5, useful in accordance with one aspect of the present invention;

SEQ ID NO:14 is a synthetic oligonucleotide sequence, designated herein as P6, useful in accordance with one aspect of the present invention;

SEQ ID NO:15 is a synthetic oligonucleotide sequence, designated herein as P7, useful in accordance with one aspect of the present invention;

SEQ ID NO:16 is a synthetic oligonucleotide sequence, designated herein as P8, useful in accordance with one aspect of the present invention;

SEQ ID NO:17 is a synthetic oligonucleotide sequence, designated herein as P9, useful in accordance with one aspect of the present invention;

SEQ ID NO:18 is a synthetic oligonucleotide sequence, designated herein as P10, useful in accordance with one aspect of the present invention;

SEQ ID NO:19 is a synthetic oligonucleotide sequence, designated herein as P11, useful in accordance with one aspect of the present invention;

SEQ ID NO:20 is a synthetic oligonucleotide sequence, designated herein as P12, useful in accordance with one aspect of the present invention;

SEQ ID NO:21 is a synthetic oligonucleotide sequence, designated herein as P13, useful in accordance with one aspect of the present invention;

SEQ ID NO:22 is a synthetic oligonucleotide sequence, designated herein as P14, useful in accordance with one aspect of the present invention;

SEQ ID NO:23 is a synthetic oligonucleotide sequence, designated herein as P15, useful in accordance with one aspect of the present invention;

SEQ ID NO:24 is a synthetic oligonucleotide sequence, designated herein as P16, useful in accordance with one aspect of the present invention;

SEQ ID NO:25 is a synthetic oligonucleotide sequence, designated herein as P17, useful in accordance with one aspect of the present invention;

SEQ ID NO:26 is a synthetic oligonucleotide sequence, designated herein as P18, useful in accordance with one aspect of the present invention;

SEQ ID NO:27 is a synthetic oligonucleotide sequence, designated herein as P19, useful in accordance with one aspect of the present invention;

SEQ ID NO:28 is a synthetic oligonucleotide sequence, designated herein as P20, useful in accordance with one aspect of the present invention;

SEQ ID NO:29 is a synthetic oligonucleotide sequence, designated herein as P21, useful in accordance with one aspect of the present invention; and SEQ ID NO:30 is a synthetic oligonucleotide sequence, designated herein as P22, useful in accordance with one aspect of the present invention.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The subject invention concerns materials and methods for genetic therapy of diseases and conditions, such as Usher syndrome 1B (USH1B). One aspect of the invention concerns AAV-based dual-vector systems that provide for expression of full-length proteins whose coding sequence exceeds the polynucleotide packaging capacity of individual AAV vector. In one embodiment, a vector system of the invention includes:

i) a first AAV vector polynucleotide comprising an inverted terminal repeat at each end (5' and 3' end) of the polynucleotide, and between the inverted terminal repeats a suitable promoter followed by (i.e., 3' to the promoter) a partial coding sequence that encodes an N-terminal part of a selected full-length polypeptide, and ii) a second AAV vector polynucleotide comprising an inverted terminal repeat at each end (i.e., the 5'- and 3'-ends) of the polynucleotide, and between the inverted terminal repeats a partial coding sequence that encodes a C-terminal portion of the selected full-length polypeptide, and optionally followed by a polyadenylation (pA) sequence. The coding sequences in the first and second vectors when combined encode the selected full-length polypeptide, or a functional fragment or variant thereof. The polypeptide encoding sequence in the first and second AAV vectors comprises sequence that overlaps.

In other words, a portion of the coding sequence present at the 3'-end of the coding sequence of the first vector is identical or substantially identical with a portion of the coding sequence present at the 5'-end of the coding sequence of the second vector. In one embodiment, the sequence overlap between the first and second AAV vectors is between about 500 and about 3000 nucleotides; between about 1000 and about 2000 nucleotides; between about 1200 and about 1800 nucleotides; or between about 1300 and about 1400 nucleotides.

In a specific embodiment, the sequence overlap is about 1350 nucleotides. In an exemplified embodiment, the sequence overlap is approximately 1365 nucleotides. In one embodiment, the polypeptide encoded is wild type or functional human myosin VIIa (hmyo7a). Amino acid sequences of wild type and functional hmyo7a polypeptides, and polynucleotides encoding them, are known in the art (see, for example, GenBank accession numbers NP_000251 and U39226.1). In one embodiment, an hmyo7a polypeptide comprises the amino acid sequence shown in SEQ ID NO:6 or SEQ ID NO:8, or a functional fragment or a variant thereof. In one embodiment, the hmyo7a polypeptide is encoded by the nucleotide sequence shown in SEQ ID NO:5 or SEQ ID NO:7. Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445). In an exemplified embodiment, the first AAV vector polynucleotide comprises the nucleotide sequence of SEQ ID NO:1, or a functional fragment and/or variant thereof, and the second AAV vector polynucleotide comprises the nucleotide sequence of SEQ ID NO:2, or a functional fragment and/or variant thereof. In one embodiment, a construct or vector of the invention is administered by parenteral administration, such as intravenous, intramuscular, intraocular, intranasal, etc. In a specific embodiment, a construct or vector is administered by subretinal injection. The construct or vector can be administered in vivo or ex vivo.

In another embodiment, a vector system of the invention comprises i) a first AAV vector polynucleotide comprising an inverted terminal repeat at each end (i.e., the 5'-end and the 3'-end) of the polynucleotide, and between the inverted terminal repeats a suitable promoter followed by (i.e., 3' to the promoter) a partial coding sequence that encodes an N-terminal part of a selected full-length polypeptide followed by a splice donor site and an intron, and ii) a second AAV vector polynucleotide comprising an inverted terminal repeat at each end (5'-end and 3'-end) of the polynucleotide, and between the inverted terminal repeats an intron and a splice acceptor site for the intron, followed by a partial coding sequence that encodes a C-terminal part of the selected full-length polypeptide, optionally followed by a polyadenylation (pA) signal sequence.

The coding sequences in the first and second vectors when combined encode the selected full-length polypeptide, or a functional fragment or variant thereof. The intron sequence in the first and second AAV vectors comprises sequence that overlaps. In other words, all or part of the intron sequence present at the 3'-end of the coding sequence of the first vector is identical or substantially identical with all or part of the intron sequence present at the 5'-end of the coding sequence of the second vector. In one embodiment, intron sequence overlap between the first and second AAV vectors is several hundred nucleotides in length. In a specific embodiment, the intron sequence overlap is about 50 to about 500 nucleotides or so in length; alternatively between about 200 and about 300 nucleotides or so in length. In one embodiment, the intron sequence utilized in the vector system of the invention is a sequence of an intron naturally present in the genomic sequence of a gene encoding the selected polypeptide. In one embodiment, the intron is intron 23 of the hmyo7a gene. In a specific embodiment, the polypeptide encoded is hmyo7a and the intron is the full intron 23 of the hmyo7a gene. In an exemplified embodiment, the first AAV vector polynucleotide comprises the nucleotide sequence of SEQ ID NO:3, or a functional fragment and/or variant thereof, and the second AAV vector polynucleotide comprises the nucleotide sequence of SEQ ID NO:4, or a functional fragment and/or variant thereof. In another embodiment, the intron sequence utilized in the vector system of the invention is a sequence of an intron that is not naturally present in the genomic sequence of a gene encoding the selected polypeptide. In a specific embodiment, the intron is a synthetic alkaline phosphatase (AP) intron. The intron sequences utilized in the vector system of the present invention can comprise splice donor and splice acceptor sequences. In one embodiment, a construct or vector of the invention is administered by parenteral administration, such as intravenous, intramuscular, intraocular, intranasal, etc. In a specific embodiment, a construct or vector is administered by subretinal injection. The construct or vector can be administered in vivo or ex vivo.

The inverted terminal repeat (ITR) sequences used in an AAV vector system of the present invention can be any AAV ITR. The ITRs used in an AAV vector can be the same or different. In particular embodiments, the ITR may be obtained from an AAV serotype 2 (AAV2) or an AAV serotype 5 (AAV5). An AAV vector of the invention can comprise different AAV ITRs. For example, a vector may comprise an ITR of AAV2 and an ITR of AAV5. AAV ITR sequences are well known in the art (see, for example, GenBank Accession Nos. AF043303.1; NC_001401.2; J01901.1; JN898962.1; K01624.1; and K01625.1).

The AAV dual-vector systems disclosed herein are able to efficiently express a therapeutic gene that is larger than what may ordinarily be packaged within a single AAV vector.

The subject invention also concerns a virus or virion comprising a polynucleotide, expression construct, or vector construct of the invention. In one embodiment, the virus or virion is an AAV virus. Methods for preparing viruses and virions comprising a heterologous polynucleotide or construct are known in the art. In the case of AAV, cells can be co-infected or transfected with adenovirus or polynucleotide constructs comprising adenovirus genes suitable for AAV helper function. Examples of materials and methods are described, for example, in U.S. Pat. Nos. 8,137,962 and 6,967,018 (each of which is specifically incorporated herein, by express reference thereto).

An AAV virus or AAV vector of the invention can be of any AAV serotype, including, but not limited to, serotype AAV1, AAV2, AAV3, AAV4, AAV5, AAV6, AAV7, AAV8, AAV5, AAV10, AAV11, and AAV12. In exemplary embodiments, AAV2 and AAV5 serotype vectors have been utilized.

In one embodiment, the AAV serotype provides for one or more tyrosine to phenylalanine (Y→F) mutations on the capsid surface. In a specific embodiment, the AAV is an AAV8 serotype having a tyrosine-to-phenylalanine (Tyr→Phe) mutation at position 733 (Y733F). In FIG. 5, a triple-mutant vector is also contemplated. It contains tyrosine-to-phenylalanine (Tyr→Phe) mutations at positions Y733F, Y500F, and Y730F, respectively, corresponding to the amino acid sequence of the wild-type AAV8-capsid protein, or in one or more of the amino acids corresponding to those sequences in one or more related AAV capids, including, for example, AAV2, AAV5, and the like.

The subject invention also concerns methods for treating or ameliorating a disease or condition, such as an eye disease, in a human or animal using gene therapy and an AAV-based dual-vector system of the present invention. In one embodiment, a method of the invention comprises administering a vector system of the invention that encodes a polypeptide that provides for treatment or amelioration of the disease or condition. In one embodiment, the vectors of the invention are provided in an AAV virus or virion. The vector system can be administered in vivo or ex vivo. In one embodiment, a vector system of the invention is administered by parenteral administration, such as intravenous, intramuscular, intraocular, intranasal, etc. Administration can be by injection. In a specific embodiment, a vector system of the invention is administered to the human or animal by intraocular subretinal injection. In one embodiment, the disease or condition to be treated is Usher syndrome and the polypeptide provided is a mammalian myosin VIIa protein. In a specific embodiment, the myosin VIIa is a human myosin VIIa polypeptide. In one embodiment, an hmyo7a polypeptide comprises the amino acid sequence shown in SEQ ID NO:6 or SEQ ID NO:8, or a functional fragment or a variant thereof. In one embodiment, the hmyo7a polypeptide is encoded by the nucleotide sequence shown in SEQ ID NO:5 or SEQ ID NO:7.

Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445). Dosage regimes and effective amounts to be administered can be determined by ordinarily skilled clinicians. Administration may be in the form of a single dose or multiple doses. General methods for performing gene therapy using polynucleotides, expression constructs, and vectors are known in the art (see, for example, *Gene Therapy: Principles and Applications* (1999); and U.S. Pat. Nos. 6,461,606; 6,204,251 and 6,106,826, each of which is specifically incorporated herein in its entirety by express reference thereto).

The subject invention also concerns methods for expressing a selected polypeptide in a cell. In one embodiment, the method comprises incorporating in the cell an AAV-based, dual-vector system as disclosed herein, wherein the vector system includes a polynucleotide sequence that encodes a selected polypeptide and of interest, and expressing the polynucleotide sequences in the cell. In certain embodiments, the selected polypeptide may be a polypeptide that is heterologous to the cell. In one embodiment, the cell is a mammalian cell, and preferably, a human cell. In one embodiment, the cell is human a photoreceptor cell, and preferably a human photoreceptor cone cell or a photoreceptor rod cell. In a specific embodiment, the cell expresses a wild type, functional, and/or biologically-active hmyo7a polypeptide that is encoded by a nucleic acid segment present in a vector system as disclosed herein. In one embodiment, the hmyo7a polypeptide is encoded by the nucleotide sequence shown in SEQ ID NO:5 or SEQ ID NO:7. Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445). The cell can be one that is provided in vivo or in vitro.

The subject invention also concerns one or more mammalian cells that contain one of the AAV-based, dual-vector systems disclosed herein.

In one embodiment, the cell is a photoreceptor cell. In a specific embodiment, the cell is a cone cell; preferably, it is a human cone cell or a human rod cell. Such cells may express one or more nucleotide sequences provided in at least a first AAV-based, dual-vector system of the invention. In a specific embodiment, the cell expresses a wild type, functional, and/or biologically active hmyo7a polypeptide that is encoded by a nucleic acid segment comprised within one or more of the AAV-based vector systems as disclosed herein. In one embodiment, the hmyo7a polypeptide is encoded by the nucleotide sequence of SEQ ID NO:5 or SEQ ID NO:7. Other polypeptides contemplated include, but are not limited to, harmonin (Uniprot Q9Y6N9), cadherin 23 (Uniprot Q9H251), protocadherin 15 (Uniprot Q96QU1), and usherin (USH2A) (Uniprot 075445).

Vector systems of the invention can include regulatory elements that are functional in the intended host cell in which the vector is to be expressed. A person of ordinary skill in the art can select regulatory elements for use in appropriate host cells, for example, mammalian or human host cells. Regulatory elements include, for example, promoters, transcription termination sequences, translation termination sequences, enhancers, and polyadenylation elements.

A vector of the invention can comprise a promoter sequence operably linked to a nucleotide sequence encoding a desired polypeptide. Promoters contemplated for use in the subject invention include, but are not limited to, cytomegalovirus (CMV) promoter, SV40 promoter, Rous sarcoma virus (RSV) promoter, chimeric CMV/chicken β-actin promoter (CBA) and the truncated form of CBA (smCBA) (see, e.g., Haire et al. 2006 and U.S. Pat. No. 8,298,818, which is specifically incorporated herein in its entirety by express reference thereto). Additional photoreceptor-specific, human rhodopsin kinase (hGRK1) promoter, rod specific IRBP promoter, VMD2 (vitelliform macular dystrophy/Best disease) promoter, and EF1 alpha promoter sequences are also contemplated to be useful in the practice of various aspects of the present invention.

In a specific embodiment, the promoter is a chimeric CMV-β-actin promoter. In one embodiment, the promoter is a tissue-specific promoter that shows selective activity in one or a group of tissues but is less active or not active in other tissue. In one embodiment, the promoter is a photoreceptor-specific promoter. In a further embodiment, the promoter is preferably a cone cell-specific promoter or a rod cell-specific promoter, or any combination thereof. In one embodiment, the promoter is the promoter for human myosin 7a gene. In a further embodiment, the promoter comprises a cone transducin α (TαC) gene-derived promoter. In a specific embodiment, the promoter is a human GNAT2-derived promoter. Other promoters contemplated within the scope of the invention include, without limitation, a rhodopsin promoter, a cGMP-phosphodiesterase β-subunit promoter, a retinitis pigmentosa-specific promoter, an RPE cell-specific promoter [such as a vitelliform macular dystrophy-2 (VMD2) promoter (Best1) (Esumi et al., 2004)], or any combination thereof.

Promoters can be incorporated into a vector using standard techniques known to those of ordinary skill in the molecular biology and/or virology arts. Multiple copies of promoters, and/or multiple distinct promoters can be used in the vectors of the present invention. In one such embodiment, a promoter may be positioned about the same distance from the transcription start site as it is from the transcription start site in its natural genetic environment, although some variation in this distance is permitted, of course, without a substantial decrease in promoter activity. In the practice of the invention, one or more transcription start site(s) are typically included within the disclosed vectors.

The vectors of the present invention may further optionally include one or more transcription termination sequences, one or more translation termination sequences, one or more signal peptide sequences, one or more internal ribosome entry sites (IRES), and/or one or more enhancer elements, or any combination thereof. Transcription termination regions can typically be obtained from the 3' untranslated region of a eukaryotic or viral gene sequence. Transcription termination sequences can be positioned downstream of a coding sequence to provide for efficient termination. Signal peptide sequences are amino-terminal peptidic sequences that encode information responsible for the location of an operably-linked polypeptide to one or more post-translational cellular destinations, including, for example, specific organelle compartments, or to the sites of protein synthesis and/or activity, and even to the extracellular environment.

Enhancers—cis-acting regulatory elements that increase gene transcription—may also be included in one of the disclosed AAV-based vector systems. A variety of enhancer elements are known to those of ordinary skill in the relevant arts, and include, without limitation, a CaMV 35S enhancer element, a cytomegalovirus (CMV) early promoter enhancer element, an SV40 enhancer element, as well as combinations and/or derivatives thereof. One or more nucleic acid sequences that direct or regulate polyadenylation of the mRNA encoded by a structural gene of interest, may also be optionally included in one or more of the vectors of the present invention.

The disclosed dual-vector systems may be introduced into one or more selected mammalian cells using any one or more of the methods that are known to those of ordinary skill in the gene therapy and/or viral arts. Such methods include, without limitation, transfection, microinjection, electroporation, lipofection, cell fusion, and calcium phosphate precipitation, as well as biolistic methods. In one embodiment, the vectors of the invention may be introduced in vivo, including, for example, by lipofection (i.e., DNA transfection via liposomes prepared from one or more cationic lipids) (see, for example, Felgner et al., 1987). Synthetic cationic lipids (LIPOFECTIN, Invitrogen Corp., La Jolla, Calif., USA) may be used to prepare liposomes that will encapsulate the vectors to facilitate their introduction into one or more selected cells. A vector system of the invention can also be introduced in vivo as "naked" DNA using methods known to those of ordinary skill in the art.

Polynucleotides described herein can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or greater as compared to a sequence exemplified herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and) XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described (Altschul et al., 1997). When utilizing BLAST and Gapped BLAST programs, the default parameters of the respective programs (NBLAST and XBLAST) can be used in accordance with published methods.

The subject invention also contemplates those polynucleotide molecules having sequences that are sufficiently homologous with the polynucleotide sequences of the invention to permit hybridization with that sequence under standard stringent conditions and standard methods (Maniatis et al., 1982). As used herein, "stringent" conditions for hybridization refers to conditions wherein hybridization is typically carried out overnight at 20-25° C. below the melting temperature ($T_m$) of the DNA hybrid in 6×SSPE, 5×Denhardt's solution, and 0.1% SDS, containing 0.1 mg/mL of a suitable non-specific denatured DNA. Calculation of the melting temperature may be obtained using the standard formula of Beltz et al., (1983):

$T_m$=81.5° C.+16.6 Log[$Na^+$]+0.41(% G+C)−0.61(% formamide)−600/length of duplex in base pairs.

Washes are typically carried out as follows:

(1) Twice at room temperature for 15 min in 1×SSPE, 0.1% SDS (i.e., a low-stringency wash); and (2) Once at $T_m$−20° C. for 15 min in 0.2×SSPE, 0.1% SDS (i.e., a moderate-stringency wash).

As used herein, the terms "nucleic acid" and "polynucleotide sequence" refer to a deoxyribonucleotide or ribonucleotide polymer in either single- or double-stranded form, and unless otherwise limited, encompass known analogs of natural nucleotides that can function in a similar manner as naturally occurring nucleotides. The polynucleotide sequences include both full-length sequences, as well as shorter sequences derived from the full-length sequences. It is understood that a particular polynucleotide sequence includes the degenerate codons of the native sequence or sequences that may be introduced to provide codon preference in a specific host cell. The polynucleotide sequences falling within the scope of the subject invention further include sequences that specifically hybridize with the sequences coding for a peptide of the invention. The polynucleotide includes both the sense and antisense strands, either as individual strands or in the duplex.

Fragments and variants of a polynucleotide or polypeptide of the present invention can be generated as described herein and tested for the presence of function using standard techniques known in the art. Thus, an ordinarily skilled artisan can readily prepare and test fragments and variants of a polynucleotide or polypeptide of the invention and determine whether the fragment or variant retains functional activity that is the same or similar to a full-length or a non-variant polynucleotide or polypeptide, such as a myosin VIIa polynucleotide or polypeptide.

As those skilled in the art can readily appreciate, there can be a number of variant sequences of a protein found in nature, in addition to those variants that can be artificially created by the skilled artisan in the lab. The polynucleotides and polypeptides of the subject invention encompasses those specifically exemplified herein, as well as any natural variants thereof, as well as any variants which can be created artificially, so long as those variants retain the desired functional activity.

Also within the scope of the subject invention are polypeptides which have the same amino acid sequences of a polypeptide exemplified herein except for amino acid substitutions, additions, or deletions within the sequence of the polypeptide, as long as these variant polypeptides retain substantially the same relevant functional activity as the polypeptides specifically exemplified herein. For example, conservative amino acid substitutions within a polypeptide that do not affect the function of the polypeptide would be within the scope of the subject invention. Thus, the polypeptides disclosed herein should be understood to include variants and fragments, as discussed above, of the specifically exemplified sequences.

The subject invention further includes nucleotide sequences that encode the polypeptides disclosed herein. These nucleotide sequences can be readily constructed by those skilled in the art having the knowledge of the protein and amino acid sequences that are presented herein. As would be appreciated by one skilled in the art, the degeneracy of the genetic code enables the artisan to construct a variety of nucleotide sequences that encode a particular polypeptide or protein. The choice of a particular nucleotide sequence could depend, for example, upon the codon usage of a particular expression system or host cell.

Polypeptides having substitution of amino acids other than those specifically exemplified in the subject polypeptides are also contemplated within the scope of the present invention. For example, non-natural amino acids can be substituted for the amino acids of a polypeptide of the invention, so long as the polypeptide having substituted amino acids retains substantially the same activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogs in general. Non-natural amino acids also include amino acids having derivatized side groups. Furthermore, any of the amino acids in the protein can be of the D- (dextrorotary) or the L- (levorotary) form.

Amino acids can be generally categorized in the following classes: non-polar, uncharged polar, basic, and acidic. Conservative substitutions whereby a polypeptide having an amino acid of one class is replaced with another amino acid of the same class fall within the scope of the subject invention so long as the polypeptide having the substitution retains substantially the same biological activity as a polypeptide that does not have the substitution. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Also within the scope of the subject invention are polynucleotides that have the same, or substantially the same, nucleotide sequence of a polynucleotide exemplified herein, except for the presence of one or more nucleotide substitutions, additions, or deletions within the sequence of the polynucleotide, so long as these variant polynucleotides retain substantially the same relevant functional activity as the polynucleotides exemplified herein (i.e., they encode a protein having the same amino acid sequence or the same functional activity as one of the polynucleotides specifically exemplified herein). Thus, the polynucleotides disclosed herein should also be understood to include variants and fragments thereof.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. As used herein, the terms "patient" and "subject" are used interchangeably and are intended to include such human and non-human species. Likewise, in vitro methods of the present invention may also be performed on cells of one or more human or non-human, mammalian species.

As one of ordinary skill in the molecular biological arts can readily appreciate, there can be a number of variant sequences of a gene or polynucleotide found in nature, in addition to those variants that may be artificially prepared or synthesized by an ordinary-skilled artisan in a laboratory environment. The polynucleotides of the subject invention encompasses those specifically exemplified herein, as well as any natural variants thereof, as well as any variants which can be created artificially, so long as those variants retain the desired biological activity.

Also within the scope of the subject invention are polynucleotides which have the same nucleotide sequences of a polynucleotide exemplified herein except for nucleotide substitutions, additions, or deletions within the sequence of the polynucleotide, as long as these variant polynucleotides retain substantially the same relevant biological activity as the polynucleotides specifically exemplified herein. Thus, the polynucleotides disclosed herein should be understood to include variants and fragments, as discussed above, of the specifically exemplified sequences.

Pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

The present invention also concerns pharmaceutical compositions comprising a vector system of the invention in combination with a pharmaceutically acceptable carrier. Pharmaceutical compositions adapted for topical or parenteral administration, comprising an amount of a compound constitute a preferred embodiment of the invention. The dose administered to a patient, particularly a human, in the context of the present invention should be sufficient to achieve a therapeutic response in the patient over a reasonable timeframe, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

The subject invention also concerns kits comprising a vector system of the invention in one or more containers. Kits of the invention can optionally include pharmaceutically acceptable carriers and/or diluents. In one embodiment, a kit of the invention includes one or more other components, adjuncts, or adjuvants as described herein. In one embodiment, a kit of the invention includes instructions or packaging materials that describe how to administer a vector system contained within the kit to a selected mammalian recipient. Containers of the kit can be of any suitable material, e.g., glass, plastic, metal, etc., and of any suitable size, shape, or configuration. In one embodiment, a vector system of the invention is provided in the kit as a solid. In another embodiment, a vector system of the invention is provided in the kit as a liquid or solution. In certain embodiments, the kits may include one or more ampoules or syringes that contain a vector system of the invention in a suitable liquid or solution form.

Multiple distinct AAV-based, dual-vector systems have been created and disclosed herein for use in gene-replacement therapies, including, for example, in the treatment of USH1B in human patients. In a specific embodiment, a vector system of the present invention employs two discrete AAV vectors that each packages a maximal-size DNA molecule (i.e., ~4.5 to 4.8 Kb). The two vectors are co-administered to selected recipient cells to reconstitute the full-length, biologically-active, Myo7a polypeptide. In these constructs, a portion of overlapping nucleic acid sequence is common to each of the vector genomes (see FIG. 1). When co-delivered to suitable cells, the overlapping sequence region facilitates the proper concatamerization of the two partial gene cassettes. These gene cassettes then undergo homologous recombination to produce a full-length gene cassette within the cells (see FIG. 1). Shared components of exemplified embodiments of the dual-vector systems include the use of AAV inverted terminal repeats (TR), the small version of the chimeric CMV/chicken β-actin promoter (smCBA), human Myo7a (hMyo7a) cDNA sequence and the SV40 polyadenylation (pA) signal.

Exemplary Definitions

In accordance with the present invention, polynucleotides, nucleic acid segments, nucleic acid sequences, and the like, include, but are not limited to, DNAs (including, but not limited to, genomic and/or extragenomic DNAs), genes, peptide nucleic acids (PNAs) RNAs (including, but not limited to, rRNAs, mRNAs, and/or tRNAs), nucleosides, as well as one or more nucleic acid segments obtained from natural sources, chemically synthesized, genetically modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

The term "effective amount," as used herein, refers to an amount that is capable of treating or ameliorating a disease or condition or otherwise capable of producing an intended therapeutic effect.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "promoter," as used herein, refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of ordinary skill in the art, such as e.g., the FASTA program analysis described by Pearson and Lipman (1988).

The term "subject," as used herein, describes an organism, including mammals such as primates, to which treatment with the compositions according to the present invention can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "vector," as used herein, refers to a nucleic acid molecule (typically one containing DNA) that is capable of replication in a suitable host cell, or one to which another nucleic acid segment can be operatively linked so as to facilitate replication of the operably-nucleic acid segment. Exemplary vectors include, without limitation, plasmids, cosmids, viruses and the like.

All patents, patent applications, provisional applications, and publications referred to or cited herein are incorporated by reference in their entirety, including all figures and tables, to the extent they are not inconsistent with the explicit teachings of this specification.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Dual-AAV Vector System 1: hMyo7a Coding Overlap

Figure 2:
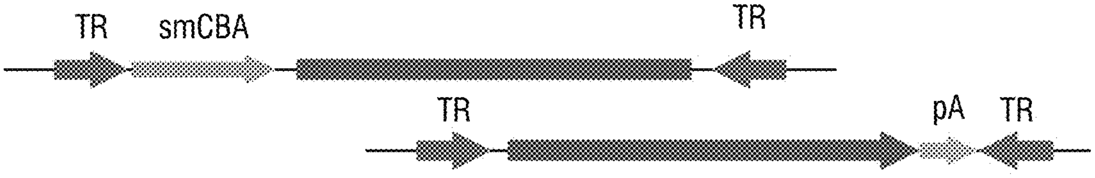
FIG. 2 shows a schematic of the two vector components that make up Dual-Vector System 1 in accordance with one aspect of the present invention.

In the case of Dual-Vector System 1 (FIG. 2) the overlapping DNA sequence shared by both vector A and vector B consists of a 1350-bp coding region for the human Myo7a gene. This is the simplest system of the present invention, and appears to be highly efficient in terms of full-length gene reconstitution, and MYO7A expression. Advantageously, each vector is of standard AAV packaging size, and as such, each packages DNA with a high degree of efficiency, and is readily adaptable to conventional GMP standards. Such vectors are also readily characterized to permit requisite regulatory approval prior to use in humans.

Example 2

Dual-AAV Vector System 2: hMyo7a Intron 23 Splicing

Figure 3:
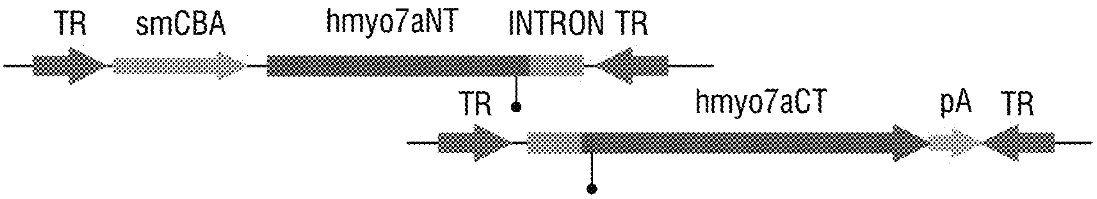
FIG. 3 shows a schematic of the two vector components that make up Dual-Vector System 2 in accordance with one aspect of the present invention. Native hMyo7a intron 23 in shown in light green; splice donor and splice acceptor sequence are shown in dark green.
Figure 4:
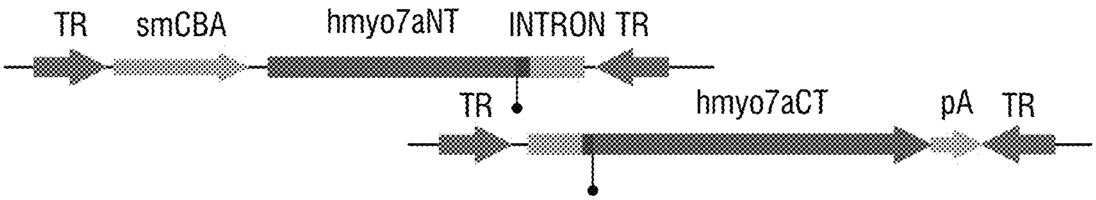
FIG. 4 shows the schematic of the two vector components that make up Dual-Vector System 3 in accordance with one aspect of the present invention. This is an exemplary standard transplicing dual vector pairs with the "intron" in this case referring to the alkaline phosphatase splice donor and acceptor sites. Synthetic alkaline phosphatase (AP) intron is shown in light blue; AP splice donor and splice acceptor sequences are shown in dark blue.

In the case of Dual-Vector System 2 (FIG. 3) the overlapping DNA sequence is composed of the native intron 23 of human Myo7a. Vector A contains the coding sequence corresponding to the amino-terminal portion of the hMyo7a cDNA relative to intron 23 (hMyo7aNT) and the native splice-donor site, followed by the entire intron 23 of hMyo7a (minus the native acceptor site). Vector B contains the carboxy-terminal portion of the hMyo7a cDNA relative to intron 23 (hMyo7aCT), and the full intron 23 of Myo7a (minus the native splice-donor site), followed by the native splice-acceptor site. Upon co-delivery to suitable mammalian host cells, the DNA of vectors A and B recombine to form a reconstituted full-length gene cassette. The resulting RNA transcript will then 'splice out' the native intron. Alternatively, recombination and formation of the gene cassette can occur via the AAV TRs. In this case, the RNA transcript will 'splice out' the native intron23-TR-intron23 motif. In both cases, however, the resulting mRNA is that of the reconstituted full-length hMyo7a gene sequence.

Example 3

In Vitro Performance of System 1: hMyo7a Coding Overlap

Figure 6A:
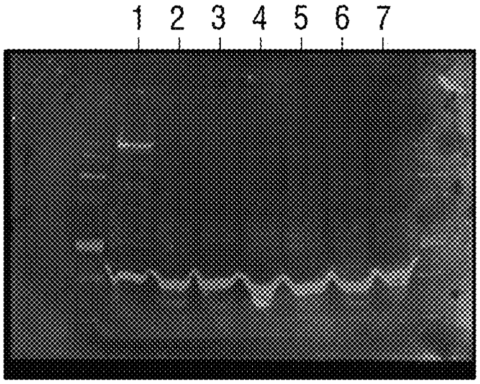
FIG. 6A and FIG. 6B show immunoblot to detect the presence of myo7A in HEK293 cells infected with Dual-Vector System 1. Results are presented as a time course from 3-7 days post infection (lanes 3-7) and are compared to cells transfected with myo7a plasmid (lane 1) and uninfected control (lane 2). The area inside the white box shown in FIG. 6A is magnified and presented at higher contrast in FIG. 6B. Starting at 3-days' post-infection, full-length human MYO7a protein was visible, with peak expression occurring around day 5.
Figure 6B:
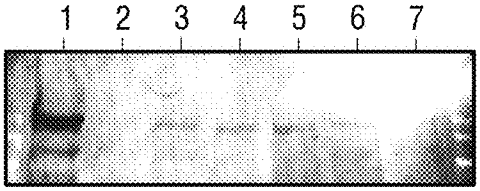

HEK293 cells were infected simultaneously with vector A and vector B of Dual-Vector System 1 (FIG. 2) at a ratio of 10000:1 vg/cell for each vector. The AAV vectors were then packaged in AAV2 virions that contain three Y→F mutations in the capsid protein (see, for example, Zhong et al., 2008). As a positive control, cells were transfected with plasmid containing full-length hMyo7a under the control of smCBA. Protein was recovered from cells at 3-, 4-, 5-, 6- and 7-days' post-infection, and an antibody directed against MYO7A was used to assay for its presence in the infected cells via immunoblotting. The results are shown in FIG. 6A and FIG. 6B. The area inside the white box is magnified, and presented at higher contrast on the right. Starting at 3-days' post-infection, the full-length human MYO7a protein was visible; peak expression of the protein occurred around Day 5.

Example 4

In Vivo Performance of System 1: hMyo7a Coding Overlap

Figure 7A:
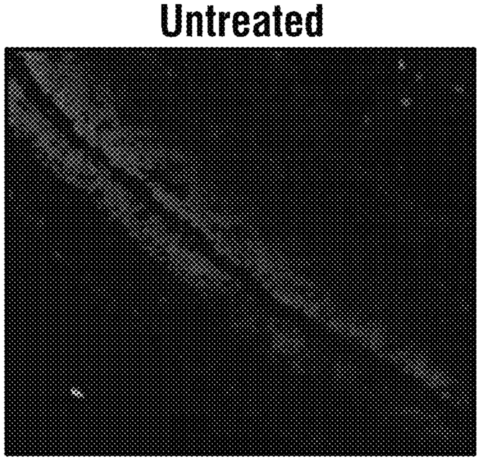
FIG. 7A and FIG. 7B show retinas from untreated mice and mice treated subretinally with Dual-Vector System 1. Immunohistochemistry (IHC) was performed using an antibody directed against MYO7A. The 'green' is the stain of MYO7A and 'blue' corresponds to nuclear, DAPI stain.
Figure 7B:
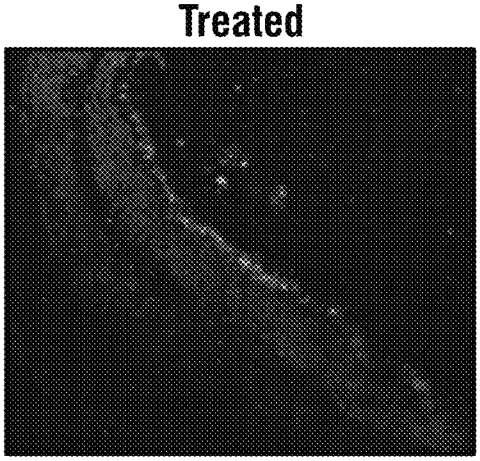
Figure 8A:
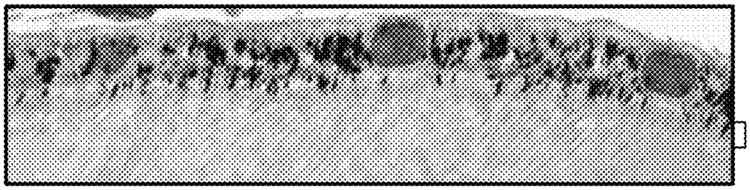
FIG. 8A, FIG. 8B, FIG. 8C, and FIG. 8D show differences in RPE melanosome localization in wild type vs. shaker-1 mice. In wild type mice, RPE melanosome apically migrate towards photoreceptor outer segments (FIG. 8A) whereas this phenomenon fails to occur in mice lacking Myo7a (shaker-1), as seen in (FIG. 8B). To the right is a high magnification image of single RPE cells from either a wild type (FIG. 8C) or shaker-1 (FIG. 8D) mouse showing this phenomenon up close.
Figure 8B:
Figure 8C:
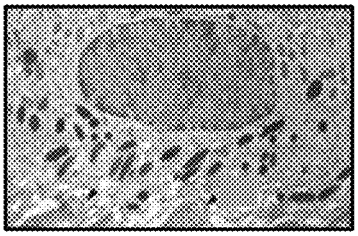
Figure 8D:
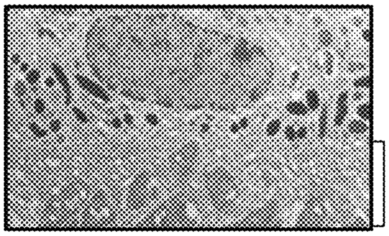
Figure 9A:
FIG. 9A, FIG. 9B, and FIG. 9C show apical migration of RPE melanosomes is restored in shaker-1 mice injected with Dual-Vector System 1. Electron microscopy reveals that melanosomes of untreated shaker-1 mice do not apically migrate (FIG. 9A). In shaker-1 mice injected with Dual-Vector System 1 (packaged in AAV2), RPE melanosomes migrate apically towards photoreceptors, which can be seen here in both low- and high-magnification images (FIG. 9B and FIG. 9C)
Figure 9B:
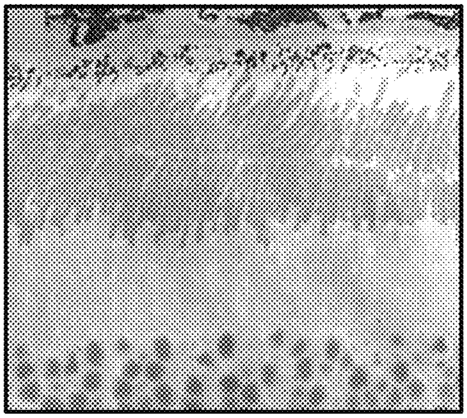
Figure 9C:
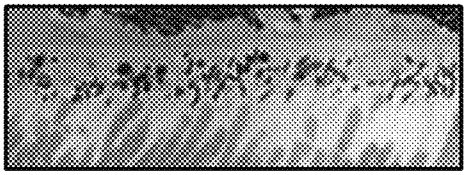

Six week old shaker-1 (Myo7a null) mice were subretinally co-injected with 1 μL of the same preparations of vector A and vector B of Dual-Vector System 1 used in the above in vitro study. Both vectors contained ~$1\times10^{12}$ vg/mL. Four weeks' post-injection, retinas from treated and untreated eyes were collected and immunohistochemistry (IHC) was performed using an antibody directed against MYO7A (see FIG. 7A and FIG. 7B). The area in green showed MYO7A-specific staining, while the areas in blue corresponded to the nuclear-specific, DAPI stain. In the treated eye, MYO7A expression was clearly visible, and it appeared to be restricted to photoreceptors—more precisely to the juncture of the photoreceptor inner and outer segments.

Example 5

AAV Dual Vectors Efficiently Deliver Oversized Genes

Animals.

Shaker-1 mice carrying the 4626SB allele, an effective null mutation (Liu et al., 1999; Hasson et al., 1997), were used on the C57BL6 genetic background, and maintained and genotyped as described (Liu et al., 1999; Gibbs et al., 2003a). They were maintained on a 12-hr light/12-hr dark cycle, with exposure to 10-50 lux of fluorescent lighting during the light phase, and were treated according to federal and institutional animal care guidelines. Homozygous mutants were distinguished from the heterozygous controls by their hyperactivity, head-tossing and circling behavior (Gibson et al., 1995), and/or by a PCR/restriction digest assay.

Construction of AAV Vectors.

Single-vector platform: AAV vector plasmid, containing the truncated chimeric CMV/chicken β-actin promoter (smCBA) (Haire et al., 2006) and MYO7A cDNA was constructed by removing the full MYO7A cDNA from pEGFP-C2 by EagI and SalI digest, and then ligating into pTR-smCBA-GFP that had been digested with NotI and SalI to remove GFP. The MYO7A cDNA (~6.7 kb) corresponded to isoform 2 of human MYO7A, and was the same as that described previously by Hashimoto et al. (2007), which was based on the sequence published by Chen et al. (1996) (see, SEQ ID NO:8). MYO7A isoform 2 is 114-kb shorter than isoform 1 (Chen et al., 1996; Weil et al., 1996). Both the MYO7A cDNA, and the resulting junctions were fully sequenced prior to packaging. All vectors intended for in vitro analyses were separately packaged in wild type AAV2, or alternatively in the AAV2(tripleY→F) capsid mutant vector (Petrs-Silva et al., 2011). As noted above, AAV2-based vectors were chosen for the in vitro experiments due to their increased transduction efficiency relative to other serotypes (Ryals et al., 2011). All vectors were packaged, purified, and titered using standard methods as previously described (Zolotukhin et al., 2002; Jacobson et al., 2006). Human embryonic kidney (HEK293) cells were transfected by the calcium phosphate method with vector plasmid carrying the full-length MYO7A coding sequence of variant 2 (the plasmid used to package fAAV). These transfected cells were then used as a positive control throughout immunoblot analyses to indicate the appropriate size of full-length MYO7A protein. Vector infections were carried out in HEK293 cells with titer-matched AAV vectors. In brief, cells were grown to 60-70% confluency. All vectors were diluted in a balanced salt solution to achieve the desired multiplicity of infection (MOI). If not specifically mentioned, cells were infected at 10,000 genome-containing particles/cell of each vector, resulting in an MOI of 20,000 total for each vector pair. Cells were incubated in medium containing 10% serum for 3 days post-infection at 37° C. under 7% $CO_2$, and then analyzed via immunoblot. Titers of $10^{12}$ to $10^{13}$ particles/mL were obtained for different lots of AAV2-MYO7A and AAV5-MYO7A.

Oligonucleotide Sequences.

For in vivo studies, a human influenza hemagglutinin (HA) tag was added to the 3' termini of the full-length, simple overlap, trans-splicing, and hybrid 3' vectors by utilizing a unique BamHI site (P19), and replacing the non-tagged 3'-end with an HA-tagged (P20) version. All constructs were sequence verified by Sanger sequencing.

AAV Vector Plasmid Design and Cloning.

Figure 22A:
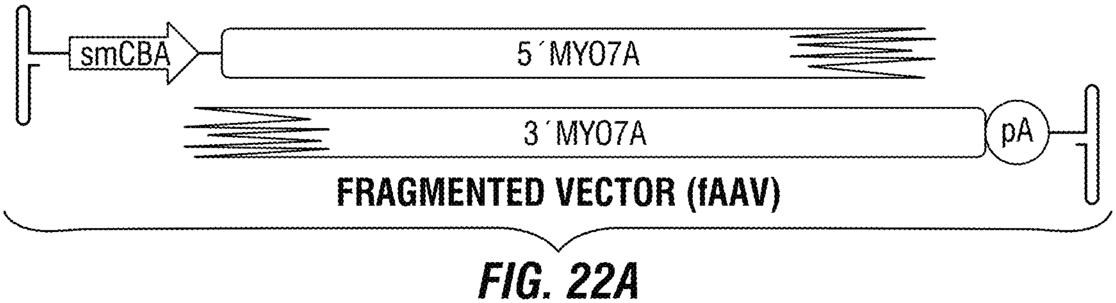
FIG. 22A, FIG. 22B, FIG. 22C, FIG. 22D, and FIG. 22E show a schematic representation of the dual-AAV-vector pairs created for this study.
Figure 22B:
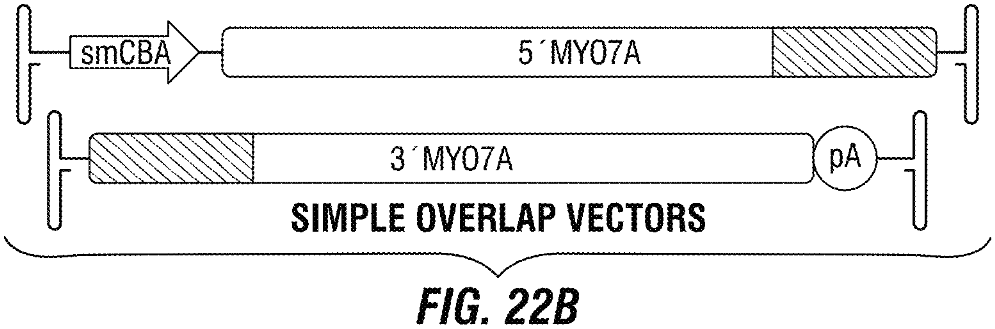
Figure 22C:
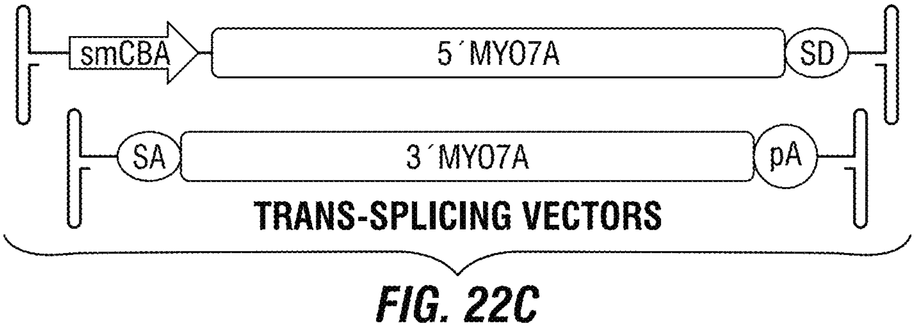
Figure 22D:
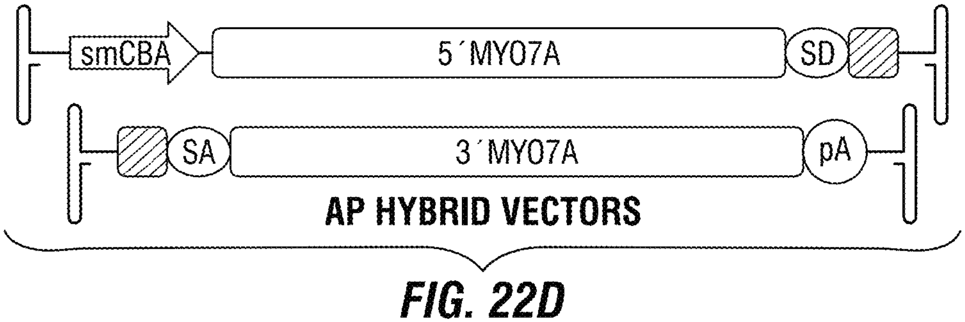
Figure 22E:
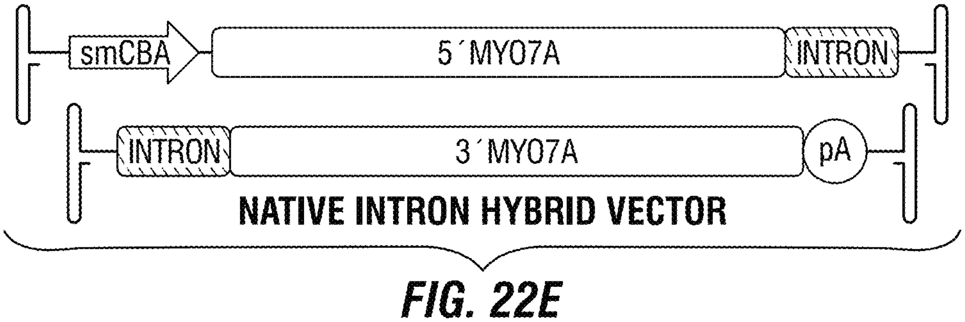

The full-length coding sequence of MYO7A (human isoform 2; GenBank Accession No. NM_001127180) was cloned into a vector plasmid containing the strong, ubiquitous CMV/chicken β-actin (smCBA) promoter (Haire et al., 2006), a polyadenylation signal, and the AAV2 ITRs. Packaging of this plasmid generated the fAAV vector (FIG. 22A). In all systems, the 5' vectors shared the smCBA promoter and a 5' portion of MYO7A, whereas the 3' vectors contained a 3'-portion of MYO7A, and a bovine growth hormone (bGH) polyadenylation signal. Oligonucleotides used for vector construction are listed in Table 2. The simple overlap contained nucleotides 1 through 3644 of MYO7A cDNA from the ATG in the 5' vector, and nucleotides 2279 through 6534 in the 3' vector. The fragments were amplified with oligonucleotides P1 and P3 by polymerase chain reaction (PCR) and cloned into the 5' vector via NotI and NheI, and the 3' vector with P3 (AflII) and P4 (KpnI), respectively. The resulting two vector plasmids share 1365 bp of overlapping MYO7A sequence (FIG. 22B). The trans-splicing and hybrid vectors utilize splice junctions composed of either ideal splice donor and acceptor sites derived from AP coding sequence or native MYO7A splice junctions from exons 23 and 24 (Yan et al., 2002). To create the 5' trans-splicing vector, the splice-acceptor site was amplified using oligonucleotides P5 and P6 (NheI), and the amplicon was then used in a second reaction with oligonucleotide P7 (NsiI) to add a part of the MYO7A coding sequence for cloning. The corresponding 3' vector was similarly created by amplifying the splice-acceptor site with oligonucleotides P8 (AflII) and P9 in a first PCR, and adding part of the 3' MYO7A coding sequence with oligonucleotide P10 (AgeI) in a second PCR (see FIG. 22C). The AP hybrid vectors were created by adding 270 bp of AP overlap sequence to the respective trans-splicing vectors (Ghosh et al., 2011). The sequence was amplified by PCR and, in so doing, appropriate restriction endonuclease sites were added. For the 5' vector oligonucleotides P11 (NheI) and P12 (SalI) were used, while oligonucleotides P13 (NotI) and P14 (AflII) were used for the 3' vector (FIG. 22D). A fourth vector pair, "native intron hybrid" vector, was also created to exploit the natural sequence in and around intron 23 of MYO7A as a recombination locus, and subsequent splicing signal. The 5'-portion was created by amplifying intron 23 with oligonucleotides P15 and P16 (NheI) first, and then using the resulting amplicon in a second reaction with oligonucleotide P7 (NsiI) to facilitate cloning. The corresponding 3'-vector was constructed by amplifying the intron 23 with oligonucleotides P17 and P18 (AflII), and the resulting amplicon, with oligonucleotide P10 (AgeI) in a second reaction (see FIG. 22E).

TABLE 2

OLIGONUCLEOTIDES USED IN THIS STUDY

| OliGo | 5'-3' sequence (restriction sites underlined) | Restriction site | (SEQ ID NO:) |
|---|---|---|---|
| P1 | GCGGCGGCCGCCACCATGGTGATTCTTCAGCAGGGGGAC | NotI | (SEQ ID NO: 9) |
| P2 | GCGGCTAGCGAAGTTCCGCAGGTACTTGAC | NheI | (SEQ ID NO: 10) |
| P3 | GCGCTTAAGCAGGTCTAACTTTCTGAAGCTG | AflII | (SEQ ID NO: 11) |
| P4 | GCGGGTACCTCACTTGCCGCTCCTGGAGCC | KpnI | (SEQ ID NO: 12) |
| P5 | GGCACCTAGTGGCTTTGAGGTAAGTATCAAGGTTACAAGAC | | (SEQ ID NO: 13) |
| P6 | GCGGCTAGCTCAGAAACGCAAGAGTCTTC | NheI | (SEQ ID NO: 14) |
| P7 | CTTCTTTGTGCGATGCATCAAG | Nsii | (SEQ ID NO: 15) |
| P8 | GCGCTTAAGCGACGCATGCTCGCGATAG | AflII | (SEQ ID NO: 16) |
| P9 | CGCCCTCGCTCCAGGTCCTGTGGAGAGAAAGGCAAAG | | (SEQ ID NO: 17) |
| P10 | GAACCCGAACCGGTCCTTG | AgeI | (SEQ ID NO: 18) |
| P11 | GCGGCTAGCCCCCGGGTGCGCGGC | NheI | (SEQ ID NO: 19) |
| P12 | GCGGTCGACGAAACGGTCCAGGCTATGTG | SalI | (SEQ ID NO: 20) |
| P13 | GCGGCGGCCGCCCCCGGGTGCGCGGCG | NotI | (SEQ ID NO: 21) |
| P14 | GCGCTTAAGGAAACGGTCCAGGCTATGTG | AflII | (SEQ ID NO: 22) |
| P15 | CAGGCACCTAGTGGCTTTGAGGTACCAGGCTAGGGACAGG | | (SEQ ID NO: 23) |
| P16 | GCGGCTAGCCGCCTGAGCCCAGAAGTTC | NheI | (SEQ ID NO: 24) |
| P17 | CGCCCTCGCTCCAGGTCCTGAAGGAGACAAGAGGTATG | | (SEQ ID NO: 25) |
| P18 | GCGCTTAAGCACCGCTTGTGTTGATCCTC | AflII | (SEQ ID NO: 26) |
| P19 | GCCAGGGAAGGATCCCATG | BamHI | (SEQ ID NO: 27) |
| P20 | GCGGGTACC*TCATGCGTAATCCGGTACATCGTAAGGGTAC*TTGCCGCTCCT GGAGCC | KpnI | (SEQ ID NO: 28) |
| P21 | AGCTTCGTAGAGTTTGTGGAGCGG | | (SEQ ID NO: 29) |
| P22 | GAGGGGCAAACAACAGATG | | (SEQ ID NO: 30) |

Oligonucleotides were used to make 5' and 3' vectors of the dual-vector platforms (P1-P20). Oligonucleotides were used to characterize the fidelity of the overlap in simple overlap, trans-splicing and AP hybrid vector platforms (P21-P22). Restriction sites used for cloning are underlined and the introduced HA tag is noted in italics (P19).

Dual-Vector Platform.

Two separate vector plasmids were constructed: Vector A contains the strong, ubiquitous "smCBA" promoter and MYO7A cDNA encoding the N-terminal portion. Vector B contains MYO7A cDNA encoding the C-terminal portion and a poly-A signal sequence. Each vector plasmid contained both inverted terminal repeats (ITRs). Using PCR with full-length MYO7A cDNA as a template, the MYO7A cDNA was divided roughly in half with amplicons encompassing nucleotide positions 1 through 3644 (Vector A) and 2279 through 6647 (Vector B) relative to ATG start position 1. The resulting two-vector plasmids shared 1365 bp of overlapping MYO7A sequence, and were 5.0- and 4.9-Kb in length, respectively. This was well within the size limitation of standard AAV vectors. Both vector plasmids were sequence verified and separately packaged by standard AAV production methods (Zolotukhin et al., 2002; Jacobson et al., 2006). The titer of the first lot contained $2.5\times10^{12}$ particles/mL of each vector, and the second lot contained $4\times10^{12}$ particles/mL of each vector.

Reverse Transcription and Characterization of Overlap Region.

HEK293 cells were infected with dual vectors, and total RNA was extracted with the RNeasy® kit (Qiagen, Hilden, Germany) according to the manufacturer's recommended protocol. Two micrograms of RNA was then subjected to DNaseI (NEB) digestion for 30 min at 37° C., followed by heat inactivation at 75° C. for 10 min. Reverse transcription to cDNA was achieved with the SuperscriptIII® kit (Life Technologies, Grand Island, N.Y., USA) according to the standard protocol utilizing the oligo dT primer. Two microliters of cDNA was used as template in a PCR (95° C. for 3 min initial denature, 35 cycles of 95° C. for 45 sec, 55° C. for 45 sec, 72° C. for 12 min, and a final 72° C. for 15 min) using oligonucleotide primers P21 and P22 (see Table 2). Annealing sites for these primers are located 5' and 3', respectively, of the area of cDNA overlap (in other words, outside the region of overlap) in the simple overlap and hybrid vector pairs. The 3'-primer annealed to sequence that was complimentary to the bGH polyA. Resulting products were digested with either PpuMI or BglII, separated on a 1.5% agarose gel, and subsequently analyzed on a UV screen. Separately, products were digested with KpnI and AgeI, and subsequently cloned into a pUC vector for sequencing of the entire overlap region. M13 forward and reverse primers that were specific for the vector were used to obtain sense and antisense reads resulting in an ~140 bp overlap of the sense and antisense reads. To demonstrate that these methods were capable of detecting aberrant sequence (i.e., quality control), a MYO7A sequence was generated using either an artificial insertion (HindIII fill-in at position 2635) or a point mutation (T→C) at position 2381, and the the analyses were repeated.

Viral Delivery in Vitro.

HEK293A cells (Invitrogen), grown in DMEM with 10% FBS and 1×NEAA and Pen/Strep (Invitrogen) were plated in 6 well-plates. The next day cells were incubated, at 37° C. and 5% $CO_2$, with AAV2- and AAV5-MYO7A at an MOI of 10,000 viral particles/cell in 500 μL of complete medium, containing also 40 μM of calpain inhibitor (Roche, Pleasanton, Calif., USA). Two hours later complete medium was added. The next day, the medium was changed and cells were incubated for an additional 48 hrs. Alternatively, some cells were transfected with 1 μg of vector pTR-smCBA-MYO7A, complexed with Lipofectamine 2000 (ratio 1:3), according to the manufacturer's instructions (Invitrogen).

Primary mouse RPE cells were derived from P14-P16 Myo7a-null animals and cultured in 24-well dishes, as described (Gibbs et al., 2003a; Gibbs and Williams, 2003b). After 48 hrs in culture, cells were transduced with viruses. Cells were incubated in 100 μL of complete medium containing 40 μM of calpain inhibitor, and 10,000 viral particles/cell from full-strength AAV stocks. After 2 hrs, 400 μL of complete medium was added to each well, and incubated overnight. The medium was changed the following day, and cells were incubated for an additional 48 hrs.

ARPE19 cells (American Type Culture Collection, Manassas, Va., USA) were cultivated in DMEM/F-12 with 10% FBS and split into 24-well plates with glass coverslips. Cells were grown to confluency and then transduced in the same manner, as were the primary RPE cells.

MYO7A Expression Analysis by Western Blot and Immunofluorescence.

HEK293A and primary mouse RPE cells that were transduced with AAV-MYO7A were collected 3 days post-transduction. For western blot analyses, cells were collected and lysed in 20 mM TRIS, pH 7.4, 5 mM $MgCl_2$, 10 mM NaCl, 1 mM DTT and 1× protease inhibitor cocktail (Sigma-Aldrich Chemical Co., St. Louis, Mo., USA). Equivalent amounts of total protein were separated on a 7.5% SDS-PAGE gel. After transfer, blots were blocked with 5% non-fat milk, and probed with mouse anti-MYO7A antibody, generated against residues 927-1203 of human MYO7A (Developmental Studies Hybridoma Bank, Iowa City, Iowa USA) (Soni et al., 2005), and mouse anti-actin antibody (Sigma-Aldrich) as a loading control.

Immunofluorescence was performed with ARPE19 and mouse RPE primary cells, 3 days after infection. Cells were fixed in 4% formaldehyde, blocked with blocking solution (0.5% BSA/0.05% saponin in PBS), incubated with the mouse anti-MYO7A followed by goat anti-mouse Alexa-568 (Molecular Probes, Carlsbad, Calif., USA). Coverslips were mounted with mounting medium containing DAPI (Fluorogel II, Electron Microscopy Sciences, Hatfield, Pa., USA) and visualized on a Leica confocal system.

Protein Extraction and Immunoblotting.

Transfected and infected HEK293 cells were harvested and washed twice in PBS and processed as previously reported with minor modifications (Boye et al., 2012). The cells were lysed by 3×30 sec pulses of sonication in 200 μL of sucrose buffer (0.23 M sucrose, 2 mM EDTA, 5 mM Tris-HCl, pH 7.5) containing protease inhibitors (Roche, Mannheim, Germany). Unlysed cells and cell debris were removed by centrifugation at 14,000 rpm for 10 min. The protein concentration of the supernatant was measured with BCA (Thermo Fisher Scientific, Rockland, Ill., USA). Equal amounts of protein were then loaded on 7.5% sodium dodecyl sulfate polyacrylamide gel electrophoresis gels (BioRad, Hercules, Calif., USA) and transferred in CAPS buffer (pH 11) onto PVDF membranes (Millipore, Billerica, Mass.). Blots were then labeled with antibodies against MYO7A (monoclonal antibody raised against amino acids 11-70 of human MYO7A; Santa Cruz, Dallas, Tex., USA; 1:1000) or HA (MMS-101P; Covance, Gaithersburg, Md., USA; 1:500) and β-actin (ab 34731; Abcam, Cambridge, Mass., USA; 1:5000). For visualization with the Odyssey system (Li-Cor, Lincoln, Nebr., USA), an antimouse and an anti-rabbit secondary antibody conjugated with CW800 and IR680 dyes (Li-Cor), respectively, were used. Semiquatitative densitometric measurements were performed with Odyssey acquisition and analysis software (Li-Cor). The dual-color images were separated in their respective channels and converted to gray scale for presentation purposes. Size markers present in one channel of each blot were added to both channels for visualization of protein sizes.

Viral Delivery In Vivo.

Mice were anesthetized with 2.0-3.0% isoflurane inhalation. The pupils of the animals were dilated with 1% (wt./vol.) atropine sulfate and 2.5% phenylephrine. A local anesthetic (0.5% proparacaine hydrochloride) was also administered. A sclerotomy in the temporal limbus was performed with a 27-Ga needle. A 32-Ga blunt needle, attached to a microsyringe pump (WPI, Sarasota Fla., USA) was inserted and 1 μL of viral solution was injected into the ventral subretinal space of P14-P16 animals. Retinal detachment was visualized under a dissecting microscope, and registered as indication of a positive subretinal injection. One microliter of the following AAV8(Y733F)-based vectors was injected subretinally in one eye of C57BL/6 mice: single fAAV ($1\times10^{13}$ vg/mL), front and back half "hybrid" vectors combined equally (each vector=$1\times10^{13}$ vg/mL), or front and back half "simple overlap" vectors combined equally (each vector=$1\times10^{13}$ vg/mL). Subretinal injections were performed as previously described (Timmers et al., 2001). Further analysis was carried out only on animals that received comparable, successful injections (>60% retinal detachment with minimal surgical complications).

Light Microscopy and Immunoelectron Microscopy of Retinas.

Eyecups were processed for embedment in either LR White or Epon, and semithin and ultrathin sections were prepared. Semithin sections were stained with toluidine blue and visualized on a Leica confocal system. Ultrathin sections were labeled with purified MYO7A pAb 2.2 (Liu et al., 1997) and monoclonal anti-opsin (1D4, R. Molday), followed by gold-conjugated secondary antibodies (Electron Microscopy Sciences), as described previously (Lopes et al., 2011). Negative control sections processed at the same time included those from Myo7a-null retinas, and, as positive control, WT animals were used.

MYO7A immunogold density was determined on sections of age-matched WT, Myo7a-null retinas and retinas of Myo7a-null animals that had been injected with AAV-MYO7A at P14-16 and dissected three weeks later. For quantification of the immunolabel, all of the gold particles in a complete section of each RPE cell were counted. The area of each cell's profile was determined using ImageJ software. For background labeling, the concentration of label in sections of untreated Myo7a-null animals was measured. Data were expressed with this background labeling subtracted.

The concentration of MYO7A and opsin immunogold labeling in the connecting cilia of photoreceptor cells was determined by counting gold particles along longitudinal profiles of connecting cilia and measuring the length of each profile.

Analysis and quantifications were performed in a minimum of three different retinas, from three different animals. Statistical analysis was performed using one-tail Student's t-test.

Six weeks postinjection, C57BL/6 mice were enucleated and their eyes processed and immunostained as previously described (Boye et al., 2011) with minor modifications. Retinas were immunostained with an antibody specific for HA (monoclonal Ab clone 12CA5; Roche), counterstained with DAPI, and imaged with a spinning disk confocal microscope (Nikon Eclipse TE2000 microscope equipped with Perkin Elmer Ultraview Modular Laser System and Hamamatsu O-RCA-R2 camera). Images were obtained sequentially using a 20× (air) objective lens. All settings (exposure, gain, laser power) were identical across images. All image analysis was performed using Volocity 5.5 software (Perkin Elmer, Waltham, Ma., USA).

Results

AAV-MYO7A Single Vector Preparations.

Figure 10A:
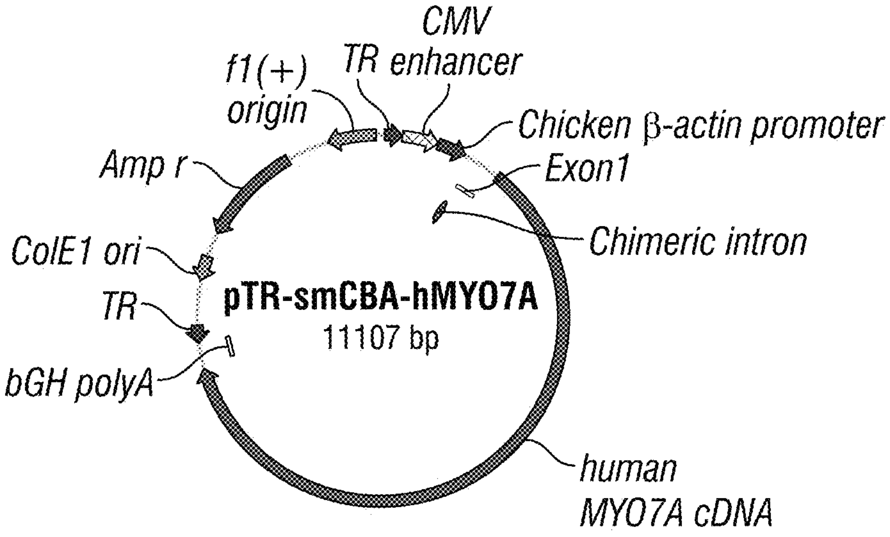
FIG. 10A, FIG. 10B, FIG. 10C, FIG. 10D, FIG. 10E, and FIG. 10F illustrate the expression of MYO7A from single AAV2 and AAV5 vectors in cultured cells.

AAV vector plasmid was engineered to contain a truncated chimeric CMV/chicken β-actin promoter, smCBA (Haire et al., 2006) and the 6.7-kb cDNA encoding the full-length isoform 2 of human MYO7A (NCBI # NM_001127180) (FIG. 10A). The smCBA promoter exhibits the same tropism and activity in mouse retinas as that of the full-length CBA promoter (Haire et al., 2006; Pang et al., 2008). Titers of $10^{12}$ to $10^{13}$ particles/mL were obtained for different lots of AAV2-MYO7A and AAV5-MYO7A. A concentration of $10^{12}$ particles/mL was regarded as the standard concentration (1×), from which dilutions were made. The experiments were performed with virus obtained from three separate preparations. No differences in expression or phenotype correction, as described below, were observed among the different lots for AAV2-MYO7A or AAV5-MYO7A at a given concentration.

MYO7A Expression in Cell Culture.

Figure 10B:
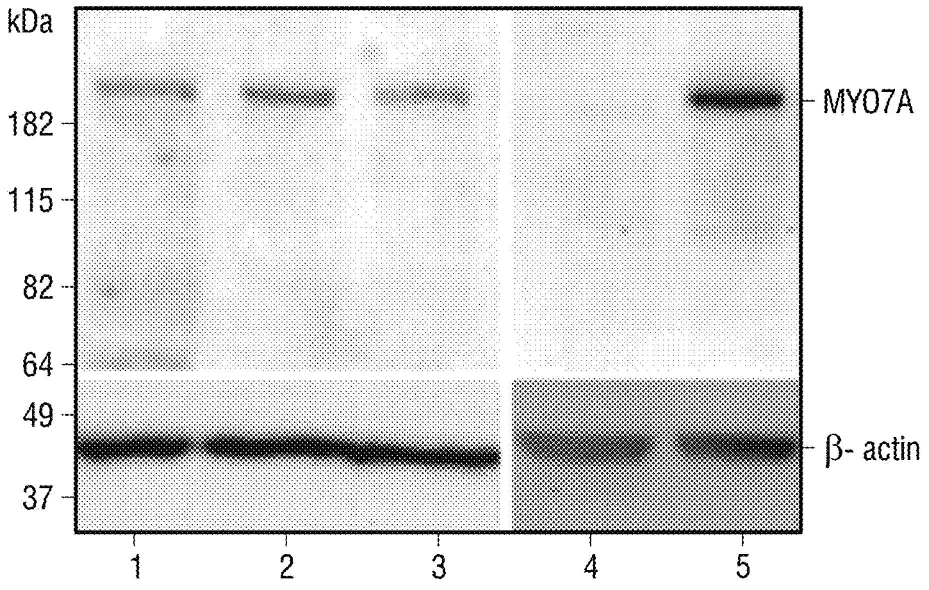
Figure 10C:
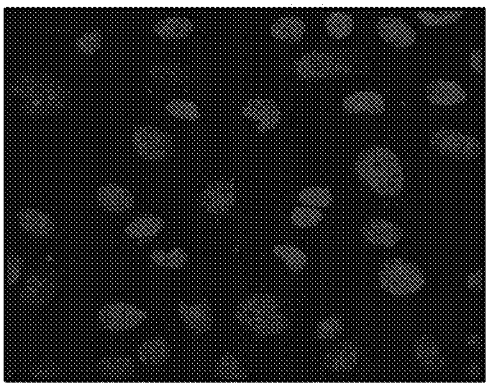
Figure 10D:
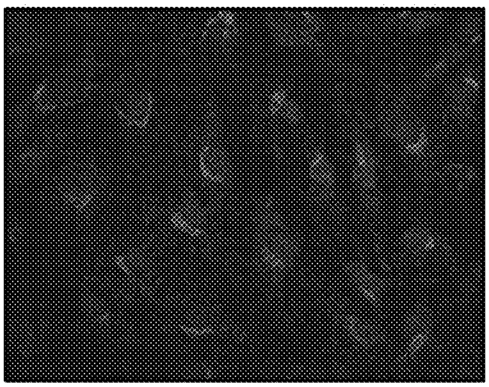
Figure 10E:
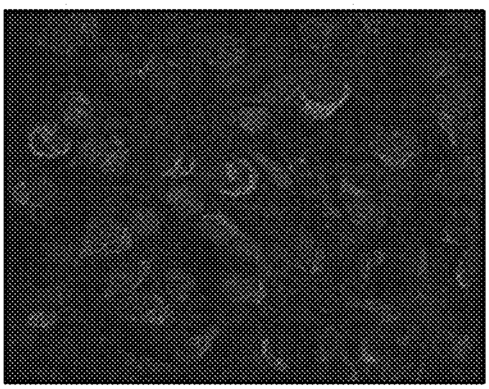
Figure 10F:
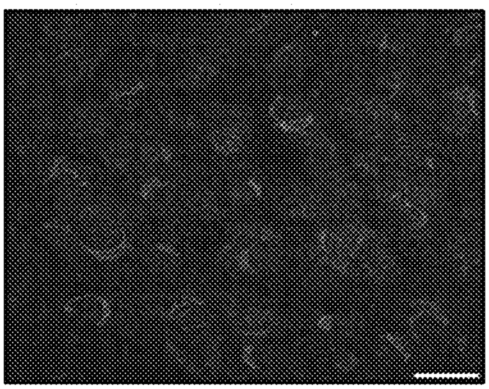

Transduction of primary cultures of Myo7a-null RPE cells with 1× single AAV2-MYO7A or AAV5-MYO7A resulted in the expression of a polypeptide that, by western blot analysis, had an apparent mass that was comparable to that of WT MYO7A protein, and was present at similar levels to that found in primary cultures of $Myo7a^{-/-}$ RPE cells (FIG. 10B). Likewise, a single band of appropriate size was detected on western blots of HEK293A cells. Immunofluorescence of the primary RPE cells showed that the MYO7A protein, resulting from 1× single AAV-MYO7A treatment of MYO7A-null cells, had a subcellular localization pattern that was comparable to that of endogenous MYO7A in control cells, indicating the generation of appropriately targeted protein (FIG. 10C, FIG. 10D, FIG. 10E, and FIG. 10F). ARPE19 cells were also infected with 1× or diluted (1:100) AAV2-MYO7A or AAV5-MYO7A, and compared with non-treated cells. An increase in MYO7A immunofluorescence was detected in the treated cells, and the intracellular localization of the label was comparable to that in untreated cells (FIG. 17A, FIG. 17B, FIG. 17C, FIG. 17D, FIG. 17E, and FIG. 17F).

Localization of MYO7A in Vivo.

Most retinal MYO7A is found in the RPE (Hasson et al., 1995), however, the protein is also present in the connecting cilium and pericilium of the photoreceptor cells (Liu et al., 1997; Williams, 2008). A diagram illustrating this distribution and the retinal functions of MYO7A has been published in a recent review (Williams and Lopes, 2011).

Three weeks following injection of 1×AAV2-MYO7A or AAV5-MYO7A into the subretinal space of Myo7a-null mice, retinal tissue was examined by immunoelectron microscopy to test for MYO7A expression. Immunogold label was evident in the photoreceptor cells, where it was localized in the connecting cilium and pericilium, comparable to that in WT retinas (FIG. 11A, FIG. 11B, FIG. 11C, FIG. 11D, and FIG. 11E). Label was also present throughout the RPE cells, particularly in the apical cell body region (FIG. 11F, FIG. 11F-1, FIG. 11G, and FIG. 11G-1; see FIG. 18A, FIG. 18B, FIG. 18C, and FIG. 18D for controls), as found in WT retinas (Gibbs et al., 2004; Liu et al., 1997).

Figure 11A:
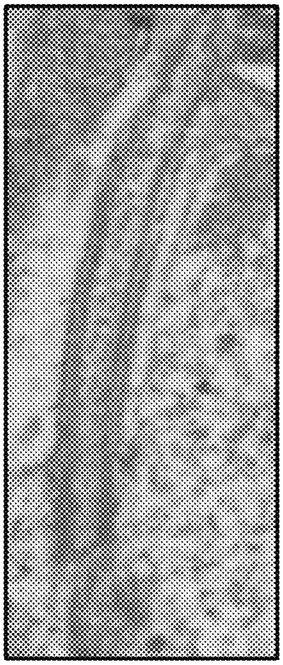
Figure 11B:
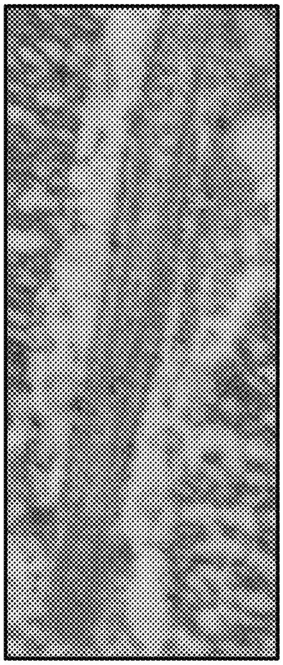
Figure 11C:
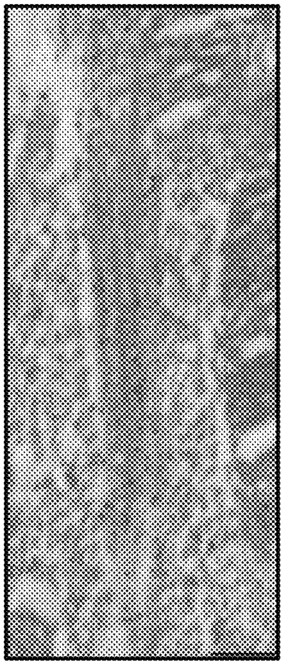
Figure 11D:
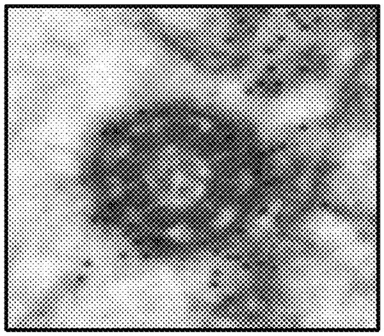
Figure 11E:
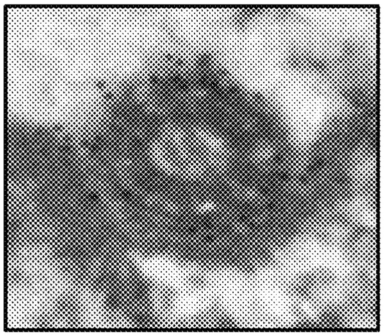
Figure 11I:
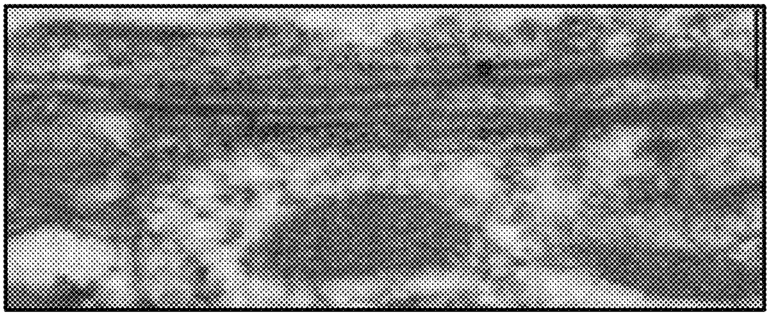
Figure 11H:
Figure 11G:
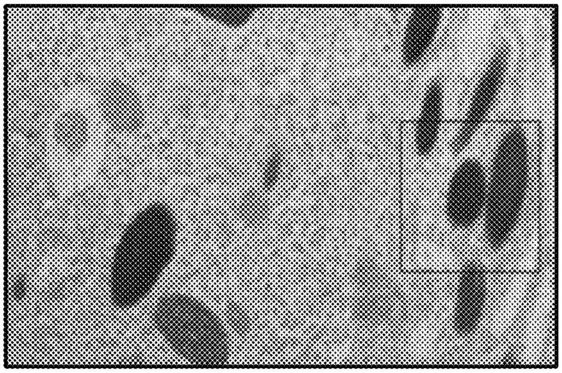
Figures 1, 11G:
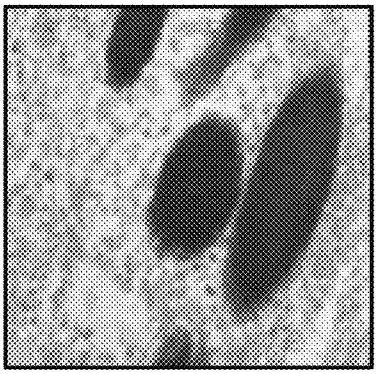
Figure 11F:
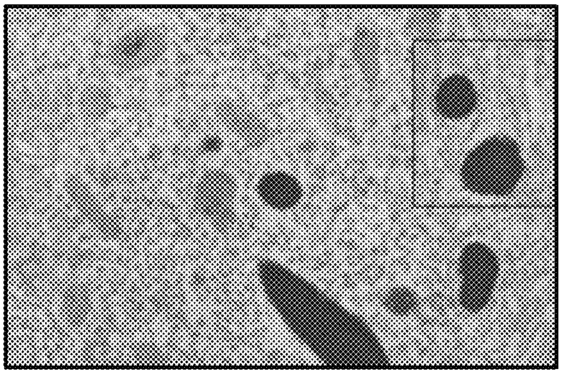
Figures 1, 11F:
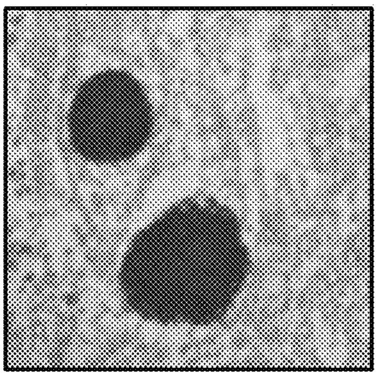

MYO7A has a similar distribution in both rod and cone photoreceptor cells (Liu et al., 1999). To test whether treatment with AAV-MYO7A also affected cone photoreceptor cells, it was determined whether MYO7A was also present in the ciliary region of cone photoreceptors. Double immunoEM of treated retinas was performed, using a MYO7A antibody together with an antibody specific for rod opsin. Although there are only a small number of cones with aligned connecting cilia found in each ultrathin section, MYO7A immunogold label was evident in the connecting cilium and periciliary region of these cones, which were identified by lack of rod opsin labeling in their outer segments (in contrast to the surrounding rod outer segments) (FIG. 11H and FIG. 11I). Hence, AAV2-MYO7A and AAV5-MYO7A can transduce cone as well as rod photoreceptor cells.

Dose-Dependent MYO7A Expression in Photoreceptor and RPE Cells.

To determine the levels of MYO7A expression following treatment with different concentrations of AAV2-MYO7A and AAV5-MYO7A (1×, 1:10 or 1:100 dilutions), MYO7A immunogold labeling was quantified in EM images, taken within 1.4 mm of the injection site. Reliable detection of MYO7A in the photoreceptor cells, where its distribution is limited to the connecting cilium and pericilium, requires the higher resolution provided by electron microscopy (Liu et al., 1997). Immunogold particle density was measured in images of the photoreceptor connecting cilium and pericilium, shown in complete longitudinal section (from the basal bodies to the base of the outer segment), and in images showing the RPE cells in apical to basal section. Particle density was expressed as particles per length of cilium for the photoreceptor cells (each connecting cilium is ~1.2 μm long), and as particles per area for the RPE cells (the entire area between the apical and basal surfaces was included). Particle density is dependent on exposure of epitopes on the surface of the section, and, as such, provides a relative linear measure of antigen density under the conditions used here (i.e., grids were etched and labeled in an identical manner, and the labeling was not so dense as to be affected by steric hindrance).

Figure 11J:
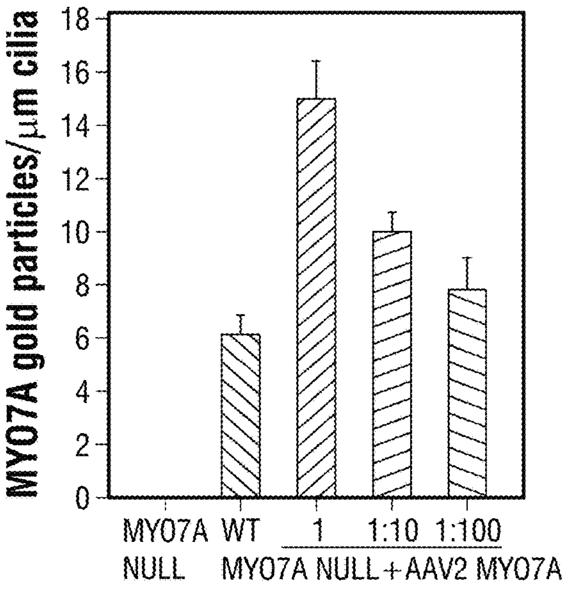
Figure 11K:
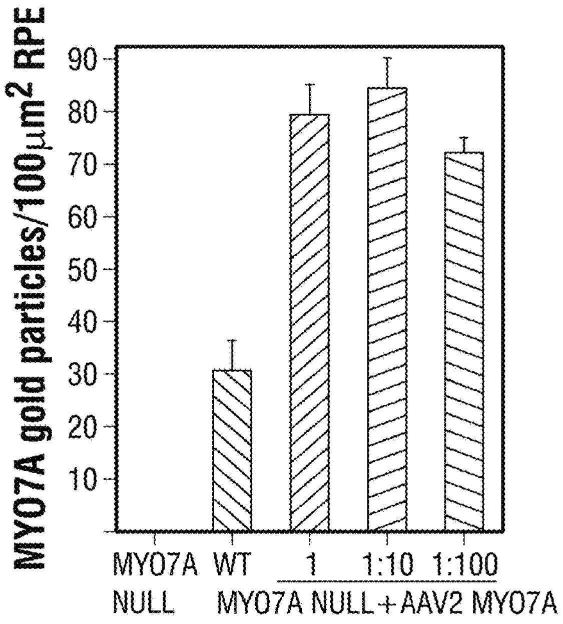
Figure 11L:
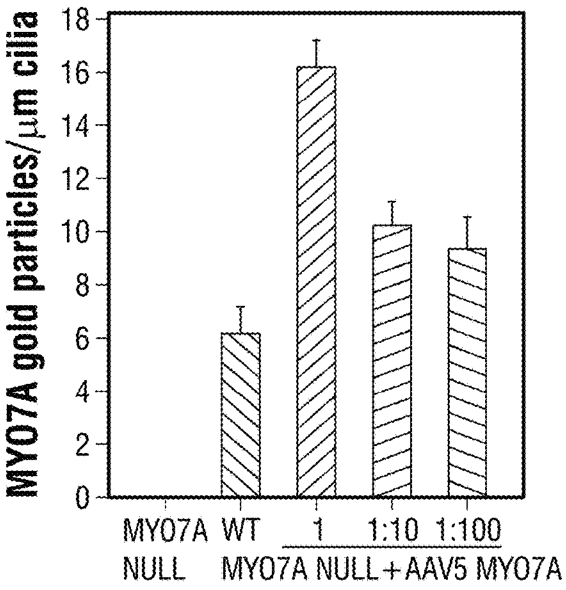
Figure 11M:
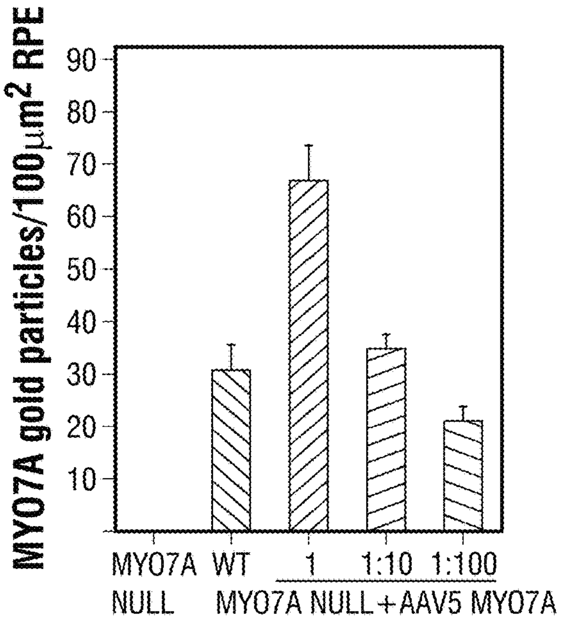
Figure 19:
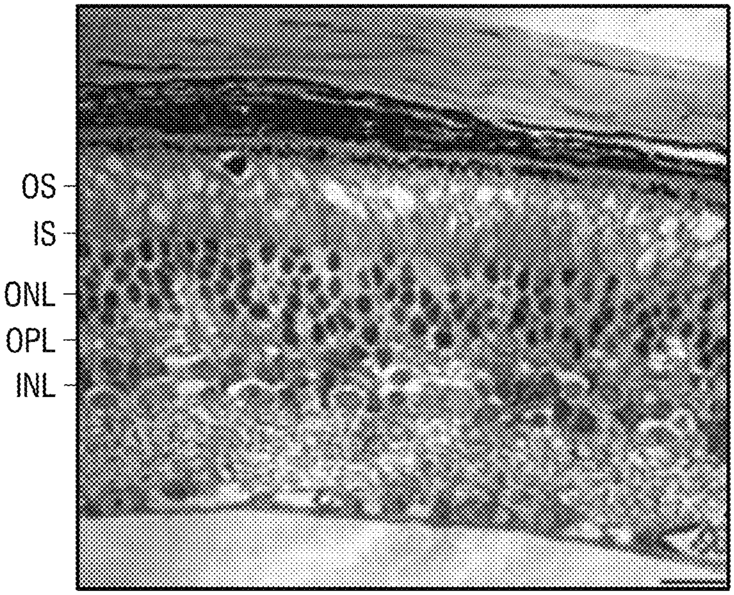
FIG. 19 shows the structural preservation of injected Myo7a-null retinas. Light microscopy of the photoreceptor layer 3 weeks after injection with 10×AAV5-MYO7A. Scale=15 μm.

Treatment with 1×AAV2-MYO7A or AAV5-MYO7A resulted in 2.5-2.7 times the density of immunolabel in the photoreceptor cilium, compared with that found in WT retinas, while the 1:10 and 1:100 dilutions resulted in a density of immunolabel that was more comparable to WT levels (FIG. 11J, FIG. 11L, and FIG. 19). Quantification of immunogold label in the RPE showed that injection of AAV2-MYO7A resulted in 2.7 times more label than in WT, with the 1:10 and 1:100 dilutions showing no significant difference (FIG. 11K). In contrast, the level of MYO7A immunolabel in the RPE of retinas injected with AAV5-MYO7A varied in relation to virus titer, with the full dose virus effecting 2.2-fold more MYO7A than that found in WT RPE, the 1:10 dilution effecting WT levels, and the 1:100 dilution resulting, on average, ~60% of WT levels (FIG. 11M).

These counts of labeling density indicate that 1×AAV-MYO7A resulted in more than double the normal level of MYO7A expression in both the photoreceptor and RPE cells. The distribution of MYO7A was not affected by this overexpression in the photoreceptor cells. In the RPE cells, the overall distribution of MYO7A was comparable to WT, with a higher concentration in the apical cell body region. However, with 1×AAV2-MYO7A or 1×AAV5-MYO7A, the proportion of MYO7A that was associated with melanosomes was only 55% of that in WT RPE: This difference is possibly because the proteins that link MYO7A to the melanosomes, MYRIP and RAB27A (Klomp et al., 2007; Lopes et al., 2007), may have remained near WT levels, and thus limited the absolute amount of MYO7A that could associate with the melanosomes.

Despite the overexpression of MYO7A, no pathology was evident in retinas, up to 3 months after injection of 1× (or 1:10) AAV2-MYO7A. However, two out of six retinas injected with $10^{13}$ particles/mL of AAV5-MYO7A (i.e., 10×) showed evidence of photoreceptor cell loss across the retina after 3 weeks (AAV2-MYO7A was not tested at this titer) (FIG. 19).

Correction of Melanosome Localization in the RPE.

Figure 12A:
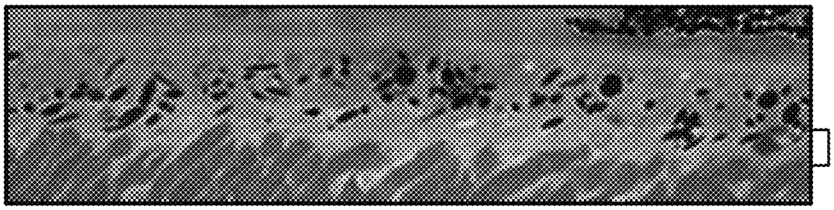
FIG. 12A, FIG. 12B, FIG. 12C, FIG. 12D, FIG. 12E, and FIG. 12F show correction of melanosome localization, following subretinal injections with AAV2-MYO7A or AAV5-MYO7A. Light micrographs showing the presence of melanosomes in the apical processes of the RPE in a WT retina (FIG. 12A) and retinas injected with AAV2-MYO7A (FIG. 12B) or AAV5-MYO7A (FIG. 12C). Further away from the injection site (FIG. 12D), melanosomes are present in the apical processes of some RPE cells, but not in others (arrows indicate apical melanosomes; white lines indicate regions where melanosomes are absent from the apical processes).
Figure 12B:
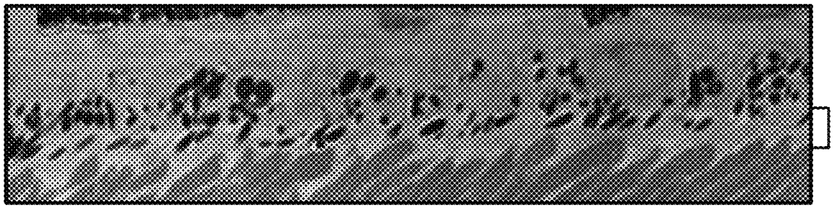
Figure 12C:
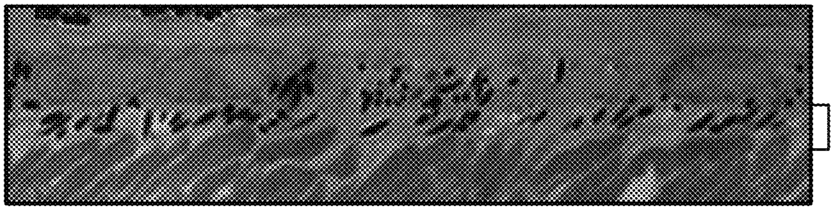
Figure 12D:
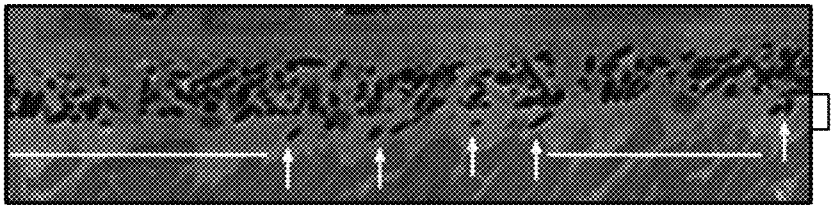
Figure 12E:
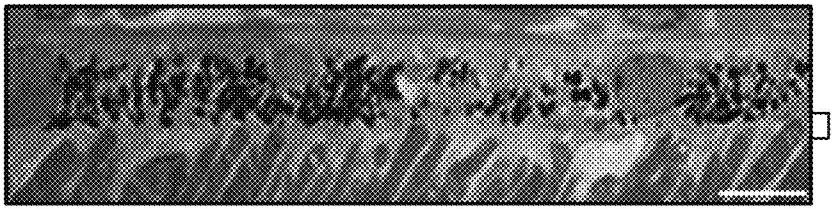
Figure 12F:
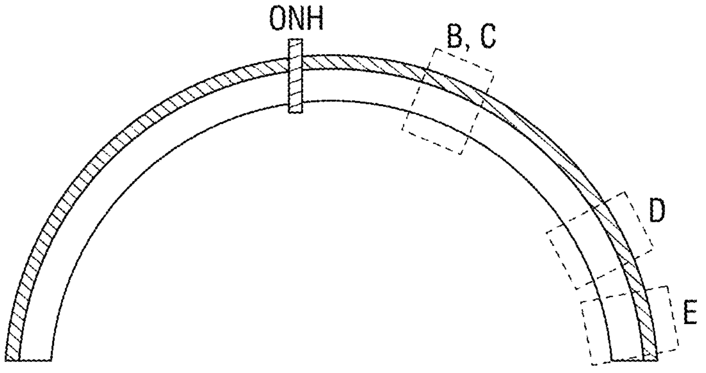
Figure 20:
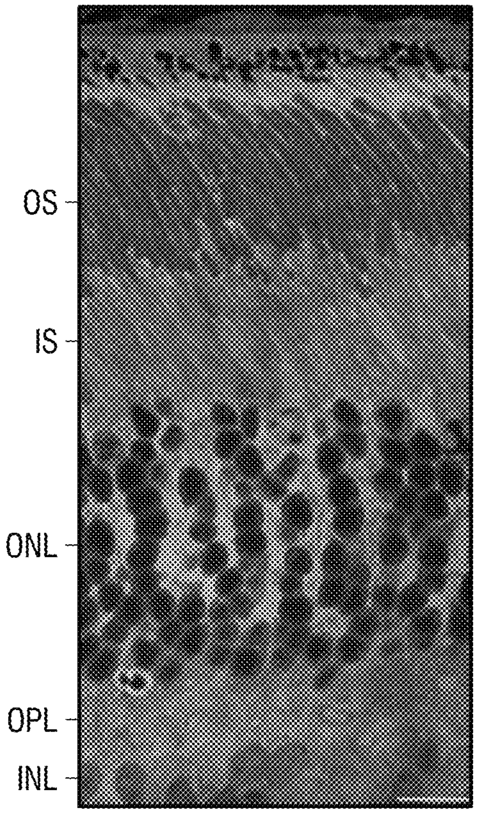
FIG. 20 shows structural preservation of injected Myo7a-null retinas. Light microscopy of photoreceptor layer 3 months after injection with 1×AAV2-MYO7A. Scale=10 μm.
Figures 21A, 21B, 21C, 21D:
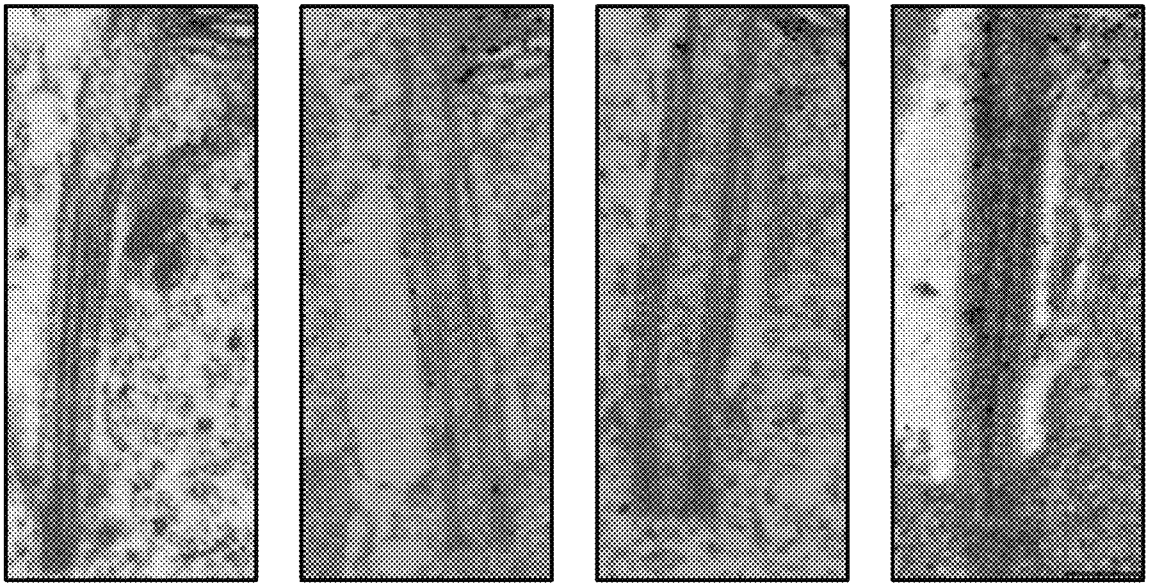
FIG. 21A, FIG. 21B, FIG. 21C, and FIG. 21D show correction of abnormal levels of opsin in the connecting cilium and pericilium of rod photoreceptors following subretinal injections with AAV2-MYO7A or AAV5-MYO7A. ImmunoEMs from WT retina (FIG. 21A), Myo7a-null retinas treated with 1×AAV2-MYO7A (FIG. 21B) or 1×AAV5-MYO7A (FIG. 21C), and from an untreated Myo7a-null retina (FIG. 21D) labeled with anti-rod opsin and 12-nm gold-conjugated secondary antibody. Scale=200 nm.

In Myo7a-mutant mice, melanosomes are absent from the apical processes of the RPE cells (Liu et al., 1998). This mutant phenotype is evident at all neonatal ages, and is due to loss of actin-based transport of the melanosomes by the myosin 7a motor (Gibbs et al., 2004). Three weeks following injection of 1×AAV2-MYO7A or AAV5-MYO7A into the subretinal space of Myo7a-null mice, melanosomes were observed to have a normal distribution in all RPE cells near the site of injection (within 1.4 mm) (n=10 each for AAV2-MYO7A and AAV5-MYO7A) (FIG. 12A, FIG. 12B, and FIG. 12C). Well away from the injection site, a mixture of corrected and uncorrected RPE cells was evident, while, at the periphery of the retina, the cells all exhibited the Myo7a-mutant phenotype, indicating lack of correction in this region (FIG. 12D, FIG. 12E, and FIG. 12F). The correction of melanosomes was still evident in retinas that were fixed 3 months after injection (FIG. 20). Correction was also observed in all eyes injected with 1:10 dilution AAV2-MYO7A (n=6) or AAV5-MYO7A (n=6), as well as in all eyes injected with 1:100 dilution AAV2-MYO7A (n=6) or AAV5-MYO7A (n=6), although with the 1:100 dilution some of the RPE cells near the site of injection were not corrected.

Correction of Opsin Distribution.

Figure 13:
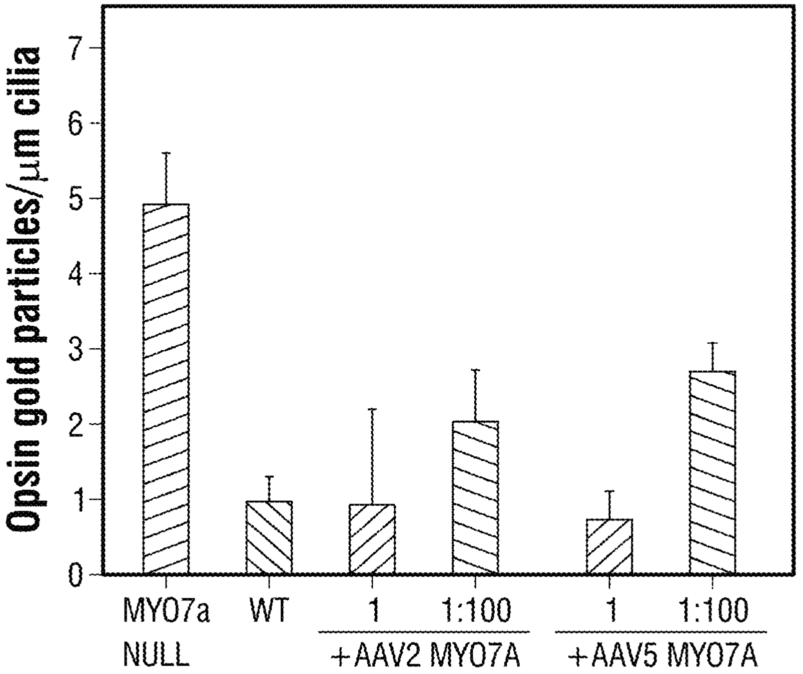
FIG. 13 shows the correction of abnormal levels of opsin in the connecting cilium and pericilium of rod photoreceptors, following subretinal injections with AAV2-MYO7A or AAV5-MYO7A. The bar graph shows opsin immunogold gold particle density along the length of the connecting cilium. Ultrathin sections of retinas from Myo7a-null and WT mice were stained with rod opsin antibody. The Myo7a-null retinas had been untreated, or treated with either 1× or 1:100 AAV2-MYO7A or AAV5-MYO7A. n=3 animals per condition. Bars indicate SEM.

Myo7a-mutant mice have an abnormal accumulation of opsin in the connecting cilia of the photoreceptor cells, a phenotype that is evident by immunoEM with opsin antibodies (Liu et al., 1999). This mutant phenotype suggested that myosin 7a functions in the vectorial delivery of opsin to the outer segment (Liu et al., 1999). Quantification of immunogold opsin labeling in the connecting cilia, demonstrated that this phenotype was corrected with 1×AAV2-MYO7A or AAV5-MYO7A (FIG. 13; FIG. 21A, FIG. 21B, FIG. 21C, and FIG. 21D). This analysis also showed phenotype correction with 1:100 dilutions, although the data indicated that a full WT phenotype was not achieved (FIG. 13), despite WT levels of MYO7A (FIG. 11J and FIG. 11L), suggesting that some of the MYO7A may not be fully functional.

AAV2-MYO7A Dual-Vector Preparations.

Figures 1, 14A:
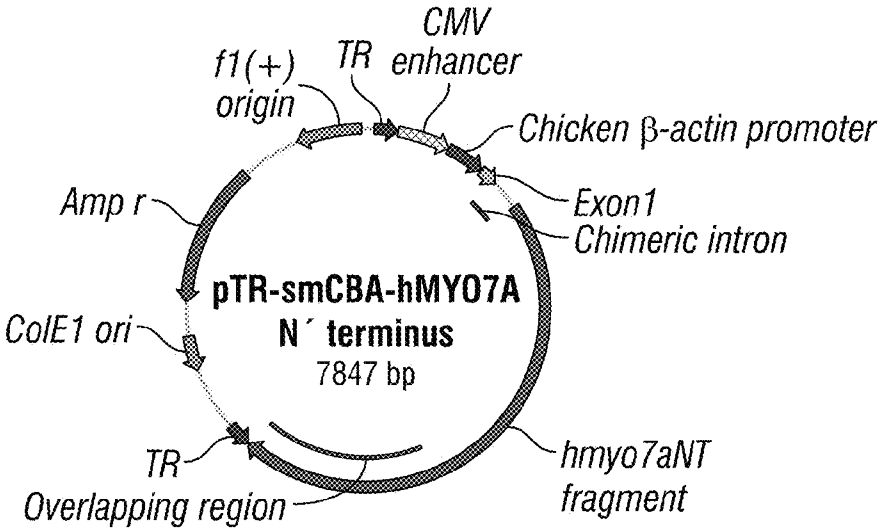
Figures 2, 14A:
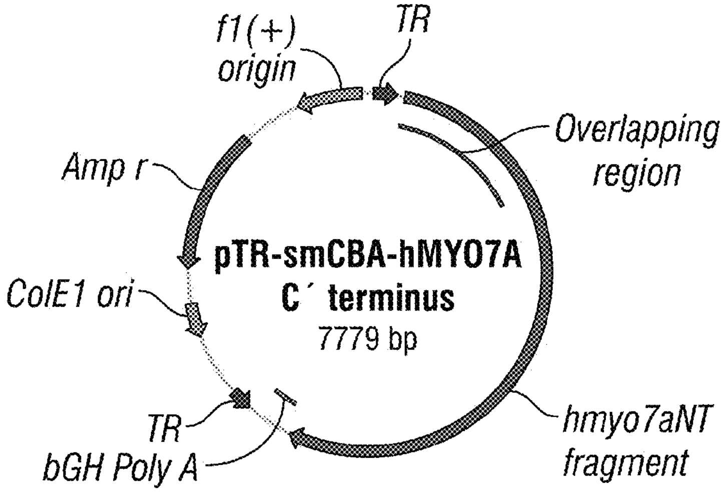

The preceding results demonstrate that a single AAV vector is capable of delivering functional MYO7A to the RPE and photoreceptor cells in vivo. Because the size of smCBA-MYO7A is ~2 kb larger than the nominal carrying capacity of an AAV (Grieger and Samulski, 2005), this transduction may involve undefined fragmentation of the smCBA-MYO7A cDNA followed by reassembly of plus and minus cDNA strands after delivery to the cell as shown for other large genes (Dong et al., 2010; Lai et al., 2010; Wu et al., 2010). To evaluate whether two AAV vectors containing defined, overlapping fragments of MYO7A cDNA (1365 bases) were also capable of mediating full-length MYO7A expression, an AAV2-based dual-vector system (FIG. 14A-1 and FIG. 14A-2) was developed. Two separate lots of the AAV2-MYO7A(dual vector) were prepared, each containing equal concentrations of AAV2-smCBA-MYO7A(5'-half) and AAV2-MYO7A(3'-half). The titer of the first lot contained $2.5\times10^{12}$ particles/mL of each vector, and the second lot contained $4\times10^{12}$ particles/mL.

MYO7A Expression with AAV2 Dual Vectors.

Figure 14B:
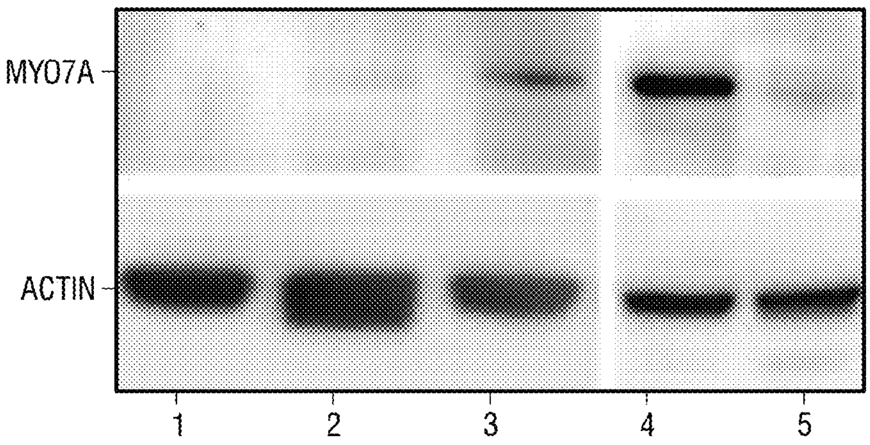

Western blot analysis of primary cultures of Myo7a-null RPE cells, infected with AAV2-MYO7A(dual vector) of either lot, showed that the cells expressed a MYO7A-immunolabeled polypeptide of comparable mass to that of WT MYO7A (FIG. 14B). However, the expression level of MYO7A in the Myo7a-null RPE cells was significantly less than that found in primary cultures of Myo7a$^{+/-}$ RPE cells (cf. lanes 2 and 3 in FIG. 14B), unlike that found for the single AAV2 or AAV5 vectors (FIG. 10B). Quantitative analysis of western blots showed that Myo7a-null RPE cells, transduced with the single vectors (1×), AAV2-MYO7A or AAV5-MYO7A, or with AAV2-MYO7A(dual vector), expressed MYO7A at levels that were 82%, 111%, and 10%, respectively, of the level of MYO7A in Myo7a$^{+/-}$ RPE cells.

Figure 16:
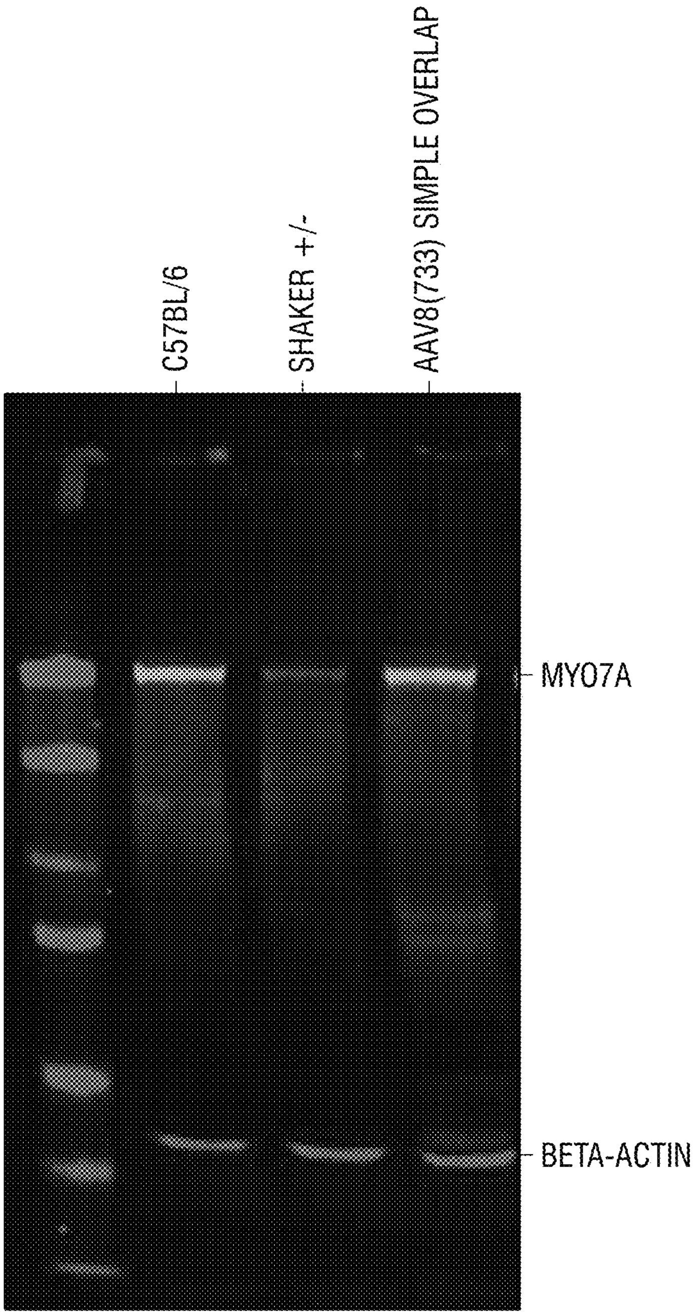
FIG. 16 shows the validation of dual AAV vectors for delivery of full-length MYO7A in vivo. Immunoblot showing expression of MYO7A (green) in retinas of wild type (C57BL/6) mice (lane 1), heterozygous shaker-$1^{+/}$ mice (lane 2) and shaker-$1^{-/-}$ mice injected with 'simple overlap' Myo7a vectors packaged in AAV8(733) vectors. Both N-terminal and C-terminal vectors of the 'simple overlap' system were injected at a concentration of $3\times10^{10}$ vector genomes/μL. Dual AAV vectors mediated expression of a MYO7A that was identical in size to that found in WT and shaker-$1^{+/-}$ mice. β-actin (visualized here in red) was used as a loading control to validate that equal amounts of protein were loaded in each well.

FIG. 16 is a Western blot using the same dual-vector system as above except in an AAV8 serotype. FIG. 16 shows expression level of myo7A using the dual-vector system that was nearly equivalent to the wild type myo7A expression level. While the reasons for the discrepancy are unclear, much better results were obtained by the inventors using the dual-vector systems than were obtained by several outside collaborators. Wild type like levels of MYO7A expression was observed in shaker-1 retinas following injection with dual-AAV8(Y733F) vectors. Thus, very good expression of MYO7A with the dual AAV platform has been achieved.

Figure 14C:
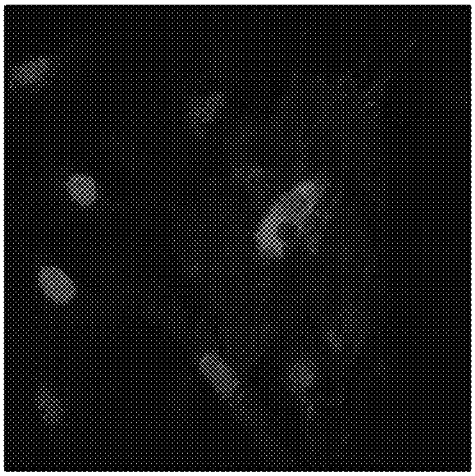
Figure 14D:
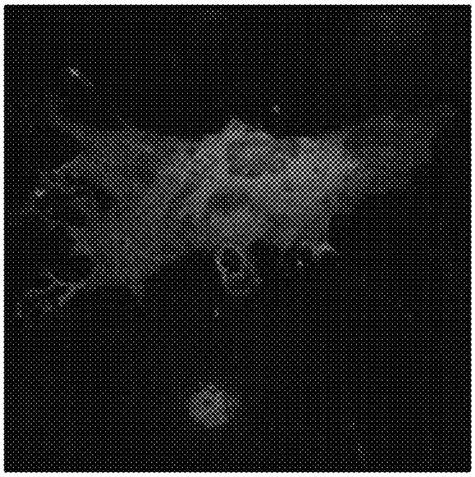
Figure 14E:
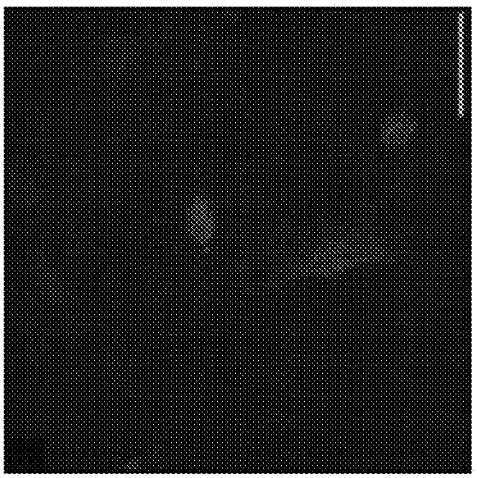
Figure 14F:
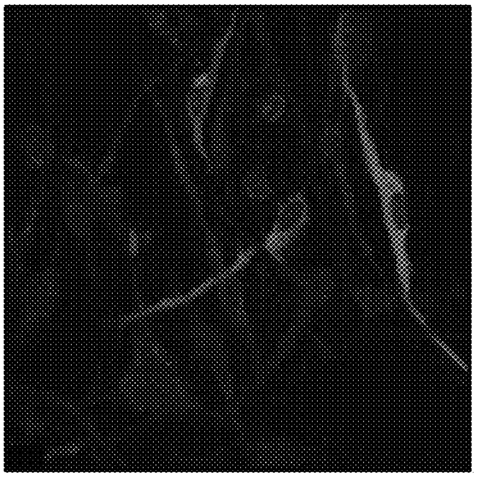
Figure 17A:
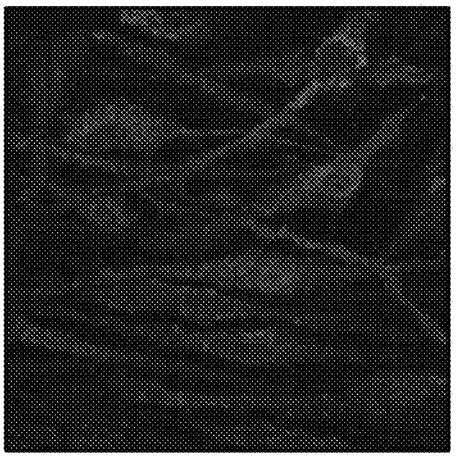
FIG. 17A, FIG. 17B, FIG. 17C, FIG. 17D, FIG. 17E, and FIG. 17F show AAV-mediated MYO7A expression in ARPE-19. Cells were transduced with 1×AAV2-MYO7A (FIG. 17A), AAV5-MYO7A (FIG. 17B), 1/100 dilutions thereof (FIG. 17C and FIG. 17D) and AAV2-MYO7A (dual) (FIG. 17F). Non-transduced cells were used as a control (FIG. 17E); Red, MYO7A; Blue, DAPI. Scale=10 μm.
Figure 17B:
Figure 17C:
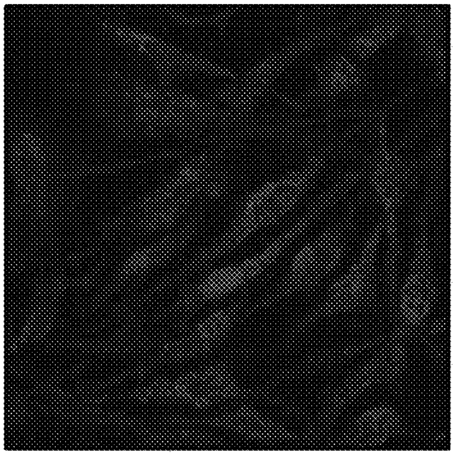
Figure 17D:
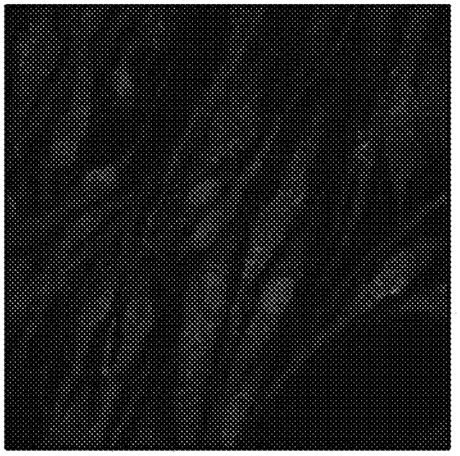
Figure 17E:
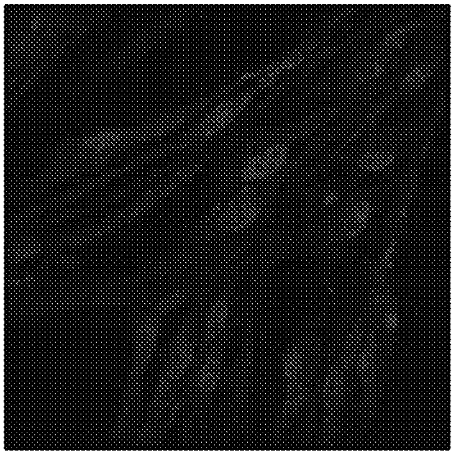
Figure 17F:
Figures 18A, 18B, 18C, 18D:
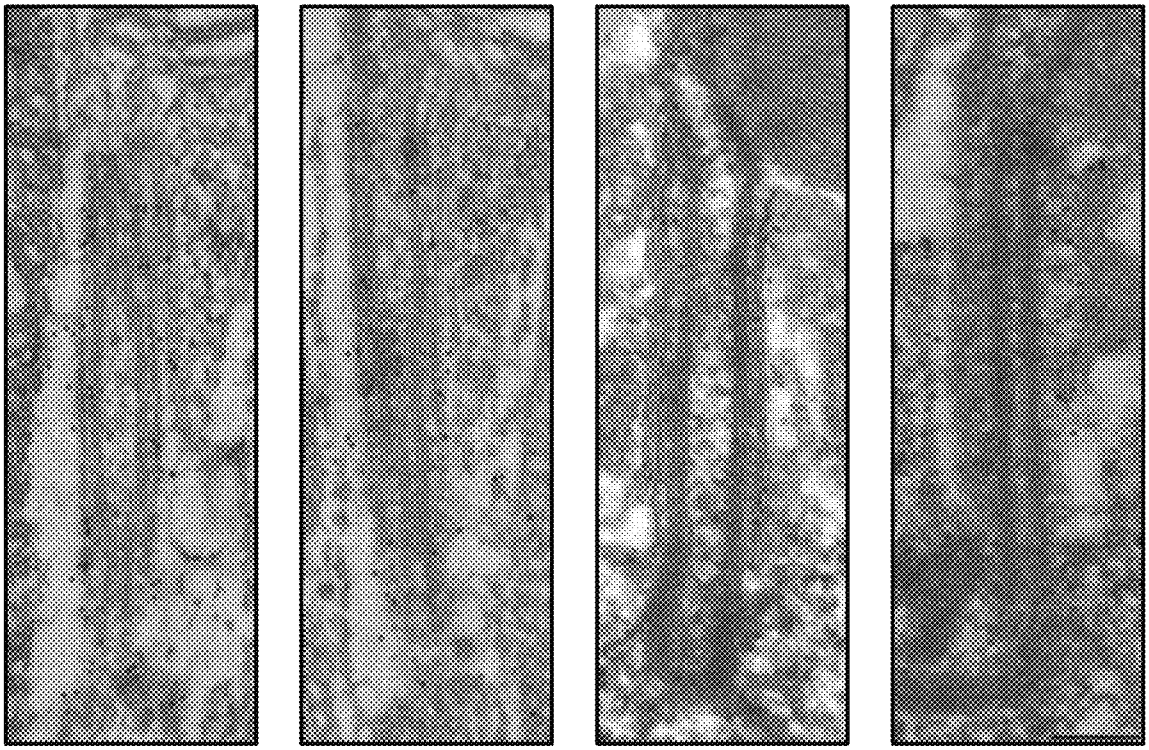
FIG. 18A, FIG. 18B, FIG. 18C, and FIG. 18D show MYO7A expression in the connecting cilium and pericilium of rod photoreceptors from Myo7a-null retinas injected with diluted AAV2-MYO7A (FIG. 18*a* and FIG. 18B) or AAV5-MYO7A (FIG. 18C and FIG. 18D)

Immunofluorescence of primary Myo7a-null RPE cells, infected with AAV2-MYO7A(dual vector), showed that a few cells scattered throughout the culture exhibited very high levels of MYO7A, but all other cells contained insignificant levels (FIG. 14C, FIG. 14D, and FIG. 14E). The cells overexpressing MYO7A typically had altered morphology, suggesting that the high levels of MYO7A may be toxic. Similarly, immunofluorescence of ARPE19 cells, infected with AAV2-MYO7A(dual vector), resulted in a minority of cells that were labeled intensely with MYO7A antibody, with most of the cells appearing to express only endogenous levels of MYO7A (FIG. 14F and FIG. 17F).

Immunolabeling of retinas, prepared 3 weeks after subretinal injection with AAV2-MYO7A(dual vector) of either lot, also showed only a few RPE cells and photoreceptor cells with clear MYO7A expression, although significant overexpression was not evident in this in vivo experiment.

Figure 14G:
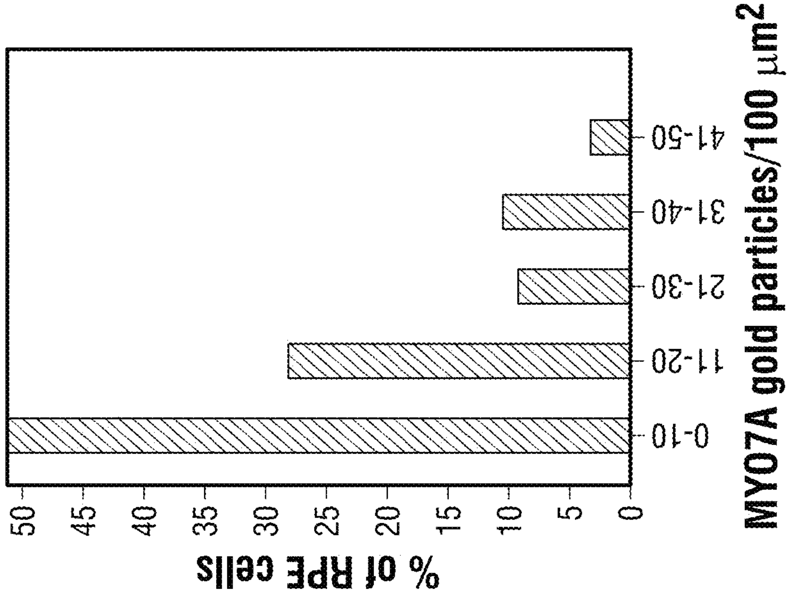

Immunogold particle counts from images of ultrathin sections were used to quantify the level of MYO7A expression in Myo7a-null retinas that were treated with the second lot of AAV2-MYO7A(dual vector). Within 1.4 mm of the injection site, MYO7A immunolabeling of the connecting cilium and pericilium of the photoreceptor cells was a mean of 48% of that in WT retinas: 2.8 particles/μm (n=3 retinas) compared with 6.5 particles/μm for WT (n=3 retinas). The mean label density in apical-basal sections of the RPE was 35% of that in WT retinas: 11 particles/100 $\mu m^2$ compared with 31 particles/100 $\mu m^2$ for WT. However, it was clear that these lower means were achieved by some cells expressing near normal amounts of MYO7A and the majority expressing very little; over half the cells had fewer than 10 particles/100 $\mu m^2$ (FIG. 14G).

Correction of Myo7a-Mutant Phenotypes with AAV2 Dual Vectors.

Figure 15A:
FIG. 15A, FIG. 15B, FIG. 15C, FIG. 15D, FIG. 15E, FIG. 15F, and FIG. 15G illustrate correction of mutant phenotypes, following subretinal injections with AAV2-MYO7A (dual).
Figure 15B:
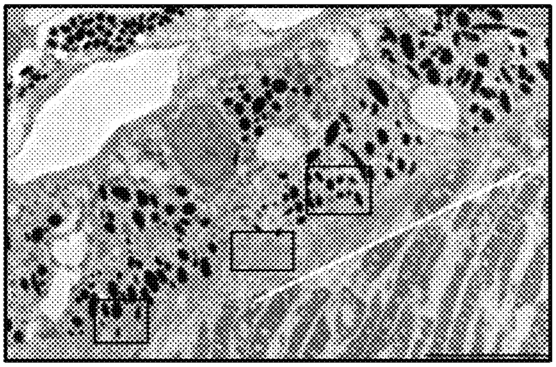
Figure 15C:
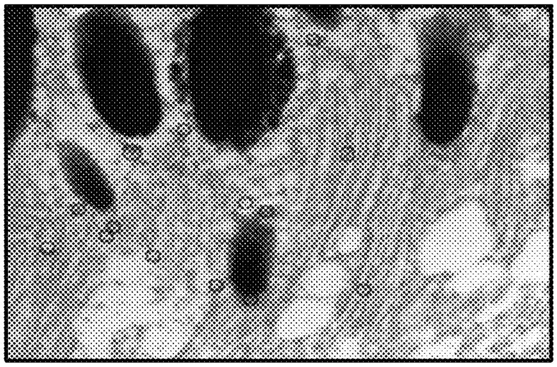
Figure 15D:
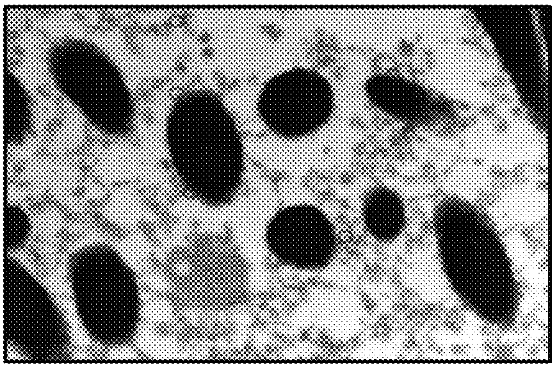
Figure 15E:
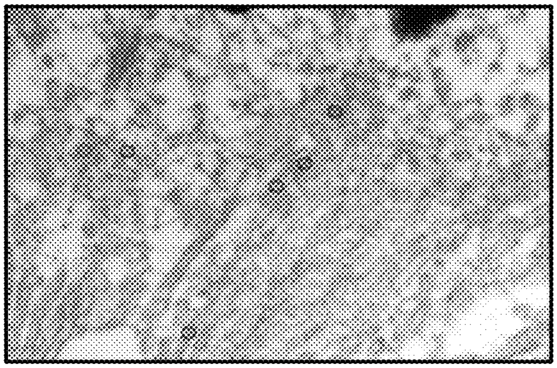

Eyes were analyzed for correction of melanosome localization and ciliary opsin distribution within 1.4 mm of the injection site. With either lot of AAV2-MYO7A(dual vector), some RPE cells (29% for lot 1 treatment [n=6 retinas], 35% for lot 2 treatment [n=9 retinas]) were observed to have a normal apical melanosome distribution, but most of the cells in this region retained the Myo7a-mutant phenotype, resulting in a mosaic effect (FIG. 15A) that contained a much lower proportion of corrected cells than that observed with a 1:100 dilution of either of the single vectors. The only correction observed in 3 eyes injected with a 1:10 dilution of AAV2-MYO7A(dual vector) (first lot), was in 18% of the RPE cells in one of the retinas. With full-strength of AAV2-MYO7A(dual vector) (second lot), opsin immunogold density averaged 3.2±0.4 particles/μm of cilium length, which was reduced from untreated retinas (4.2±0.8 particles/μm; p=0.003), but still greater than WT levels (1.1±0.2 particles/μm), suggesting that most cells were not corrected.

Figure 15F:
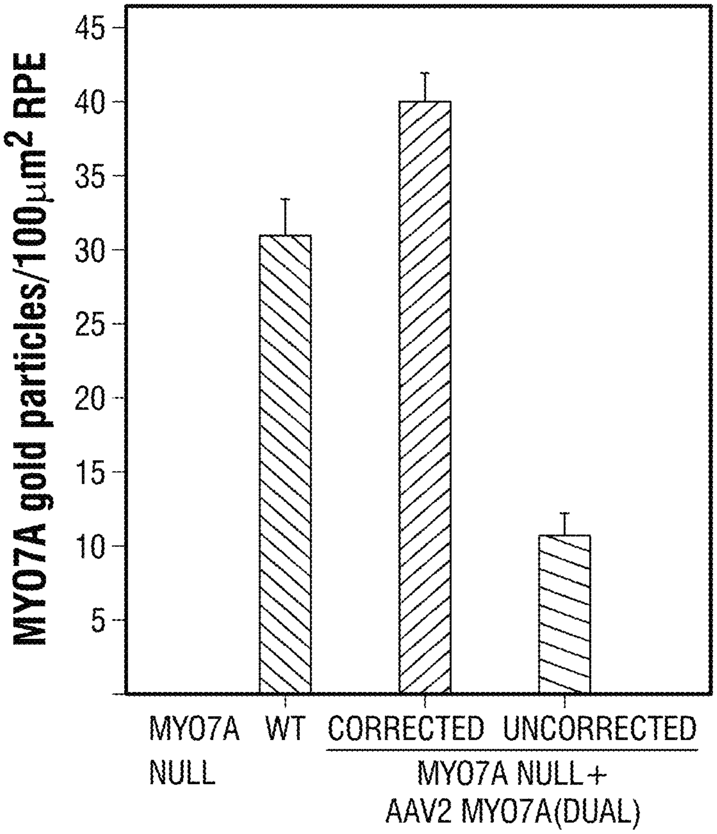
Figure 15G:
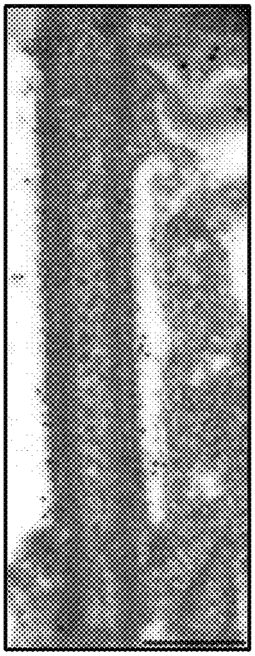

Using immunoelectron microscopy, a correlation between phenotype correction and the expression level of MYO7A was identified (determined by the mean concentration of immunogold particles in an apical-basal section of each RPE cell) (FIG. 15B, FIG. 15C, FIG. 15D, and FIG. 15E). From the eyes injected with AAV2-MYO7A(dual vector) (second lot), it was shown that the corrected RPE cells contained a mean of 108% of the WT level of MYO7A (the minimum level was 82%). RPE cells that were not corrected contained a mean of 26% of the WT level of MYO7A (the maximum level was 92%). While these data showed that higher expression of MYO7A is correlated with phenotype correction (FIG. 15F), it also indicated that some of the labeled MYO7A protein was not functional, given that melanosomes are localized normally in mice that are heterozygous for the Myo7a-null allele and have only ~50% of the WT level of MYO7A.

Expression of MYO7A with Simple Overlap Vectors.

Figure 23A:
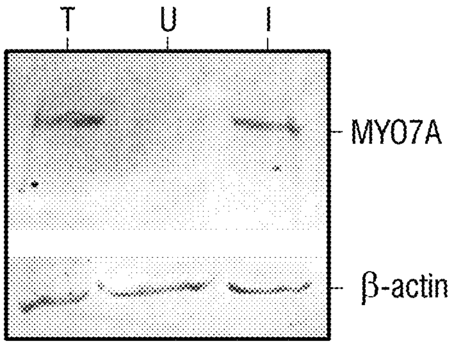
FIG. 23A, FIG. 23B, and FIG. 23C show human embryonic kidney (HEK293) cells express human MYO7A after infection with simple overlap vectors (MOI of 10,000 for both vectors) packaged in AAV2(tripleY-F). Equal amounts of protein were separated on 7.5% sodium dodecyl sulfate (SDS) polyacrylamide gel electrophoresis (PAGE) and stained for MYO7A.
Figure 23B:
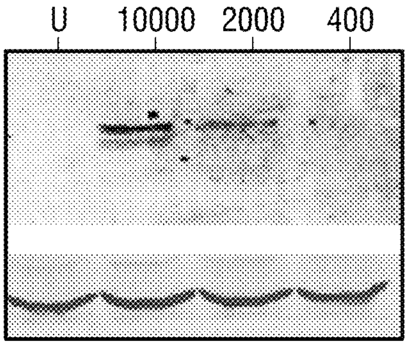
Figure 23C:
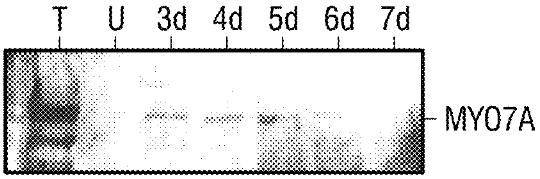

AAV2-based simple overlap vectors were evaluated in vitro at a variety of MOIs to evaluate how the concentration of vector pairs related to MYO7A expression. How levels of MYO7A changed over time was also evaluated in infected cells. HEK293 cells were infected with simple overlap vector pairs packaged in AAV2(tripleY-F) vector (FIG. 23A). A preliminary co-infection with AAV2(tripleY-F) simple overlap vectors (MOI of 10,000 for each vector) indicated that MYO7A is expressed, and that migration of the protein on gel is identical to a full-length transfection control (FIG. 23A). Coinfection at MOIs of 400, 2000, and 10,000 of each vector shows that the efficiency of the simple overlap system is proportional to the amount of 5' and 3' vectors used (FIG. 23B). MYO7A expression increased as a function of incubation time up to 5 days postinjection in HEK293 cells (FIG. 23C). The visible expression decline was because of a reduction of viable cells in the culture vessel at the later times.

Comparison of fAAV-MYO7A to Dual-AAV-MYO7A Expression and Evaluation of AAV Serotype Efficiency.

Figure 24:
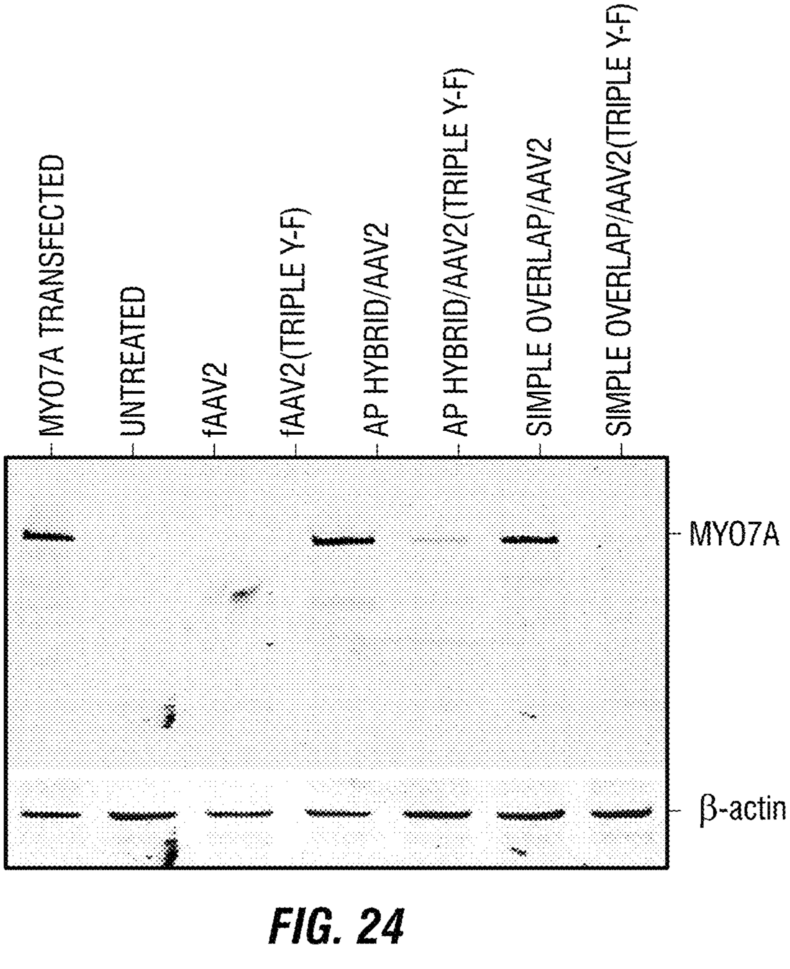
FIG. 24 shows the comparison of AAV2 and AAV2 (tripleY→F mutant capsid)-based vectors in HEK293 cells. Cells were infected with single fAAV, AP hybrid, and simple overlap MYO7A dual-vector platforms packaged in AAV2 or AAV2(tripleY→F mutant capsid) at an MOI of 10,000. HEK293 cells transfected with MYO7A plasmid were used as a positive control.

Previously, it was shown that fAAV-MYO7A was able to ameliorate the retinal phenotype of the shaker1 mouse (Colella et al., 2013; Lopes et al., 2013; Trapani et al., 2013). To provide a basis for comparison dual-AAV-vector expression was evaluated relative to fAAV in vitro. After infection in HEK293 cells, all dual-vector systems expressed MYO7A more efficiently than fAAV (FIG. 24). The AP hybrid platform showed the strongest expression, followed by the simple overlap system.

Other studies have shown, in the context of a conventionally sized DNA payload, that the transduction efficiency and kinetics of AAV2(tripleY-F) vectors are increased relative to standard AAV2 both in vitro and in vivo (Li et al., 2010; Markusic et al., 2010; Ryals et al., 2011). The efficiency of AAV2 versus AAV2(tripleY-F) dual vectors was directly compared in HEK293 cells. Surprisingly, standard AAV2-mediated MYO7A expression was higher than that seen with titer-matched AAV2(tripleY-F) (FIG. 24). Identical results were obtained when comparing different AAV2 and AAV2(tripleY-F) dual-vector preparation packaged with identical vector plasmid.

Comparison of Relative Efficiencies and Specificity of Full-Length MYO7A Expression.

Figure 25A:
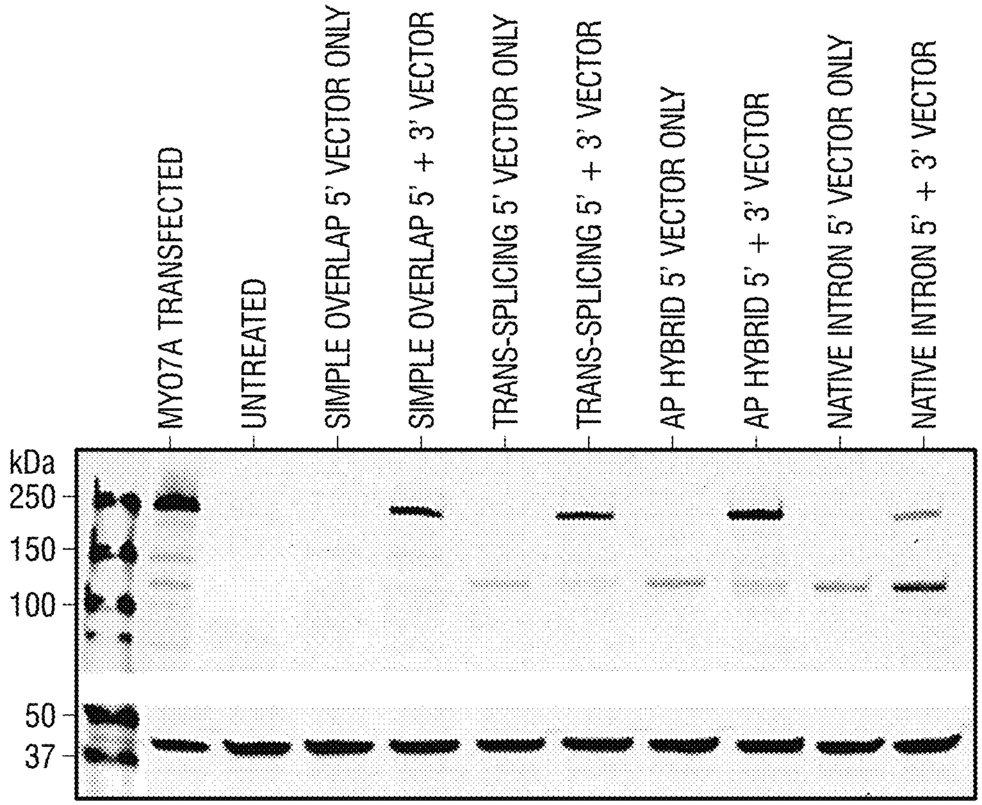
FIG. 25A, FIG. 25B, and FIG. 25C show human MYO7A expressed in HEK293 cells. Cells were infected with AAV2-based vector platforms. For each of the dual-vector systems, the corresponding 5' and 3' vectors (or the 5' vector alone) were used for infection. HEK293 cells transfected with MYO7A plasmid were used as a positive control. Cells were infected with the MYO7A dual-vector pairs at an MOI of 10,000 for each vector. Protein samples were analyzed on Western blot with an antibody against MYO7A (FIG. 25A). Each platform's relative ability to promote reconstitution was compared by quantifying the amount of 5' vector-mediated truncated protein product in the presence or absence of the respective 3' vector (FIG. 25B). Full-length MYO7A expression mediated by dual vectors was quantified relative to transfection control (FIG. 25C)
Figure 25B:
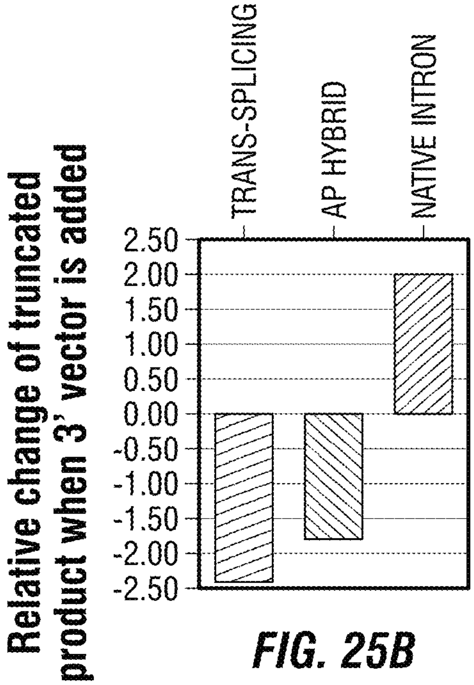
Figure 25C:
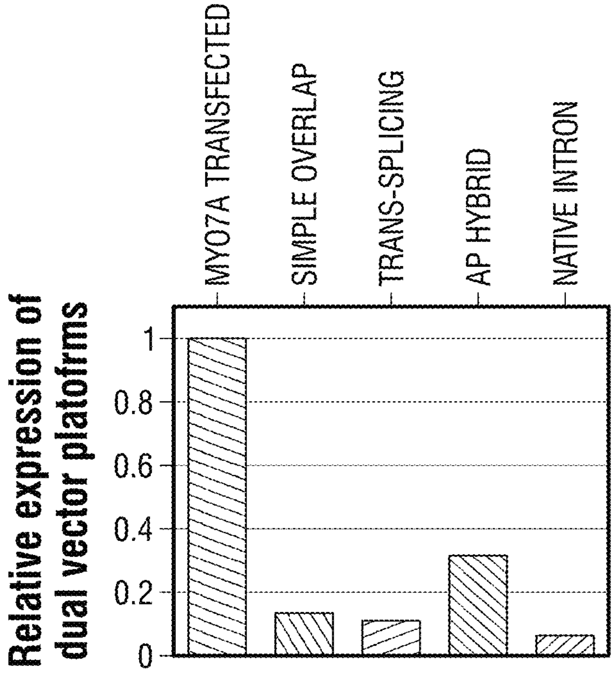

To quantitatively evaluate the relative expression efficiencies of the dual-vector platforms and to assess specificity of full-length protein, HEK293 cells were infected with either the 5' and 3' AAV2-based vector pairs combined or the corresponding 5' vector alone. An additional hybrid vector pair was included that incorporated native MYO7A intronic sequence (intron 23) that served as overlapping sequence and provided appropriate splicing signals. All 5' vectors produced low amounts of a defined, less than full-length peptide detectable on Western blot with the exception of the simple overlap vector (FIG. 25A). However, the trans-splicing and the AP hybrid platforms revealed a distinct decrease of this undesired product when the 3' vector was added to the sample (FIG. 25A). The native intron hybrid platform also showed this secondary band on Western blots, again suggestive of a truncated protein originating from the 5' vector alone. In contrast to all other platforms tested, this band intensity increased with the addition of the 3' vector. Each platform's relative ability to promote reconstitution was compared by quantifying the amount of 5' vector-mediated truncated protein product in the presence or absence of the respective 3' vector (FIG. 25B). Full-length MYO7A expression on Western blot was then quantified relative to transfection control (FIG. 25C). AP hybrid-mediated MYO7A was the strongest followed by simple overlap, trans-splicing, and native intron hybrid (FIG. 25C).

Characterization of the Overlap/Splice Region of the Expressed MYO7A.

Figure 26A:
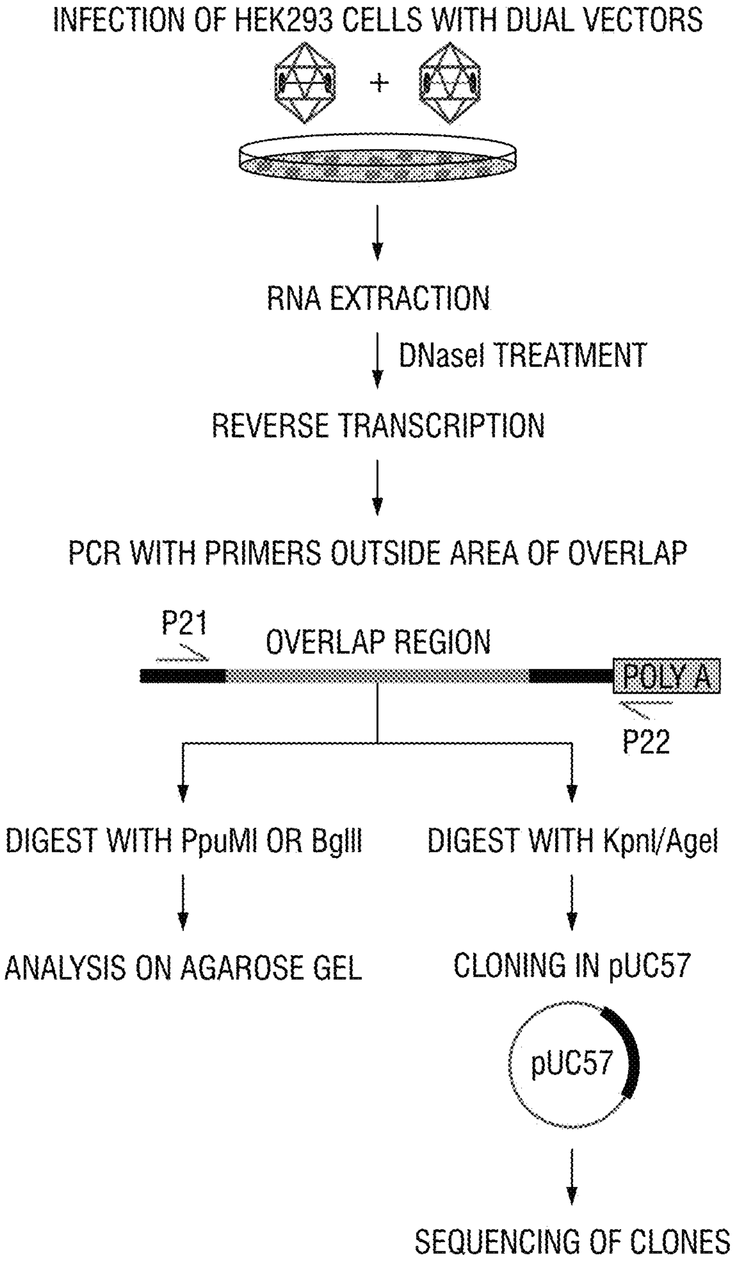
FIG. 26A, FIG. 26B, and FIG. 26C show the characterization of MYO7A dual-vectors' restoration of coding sequence. The experimental plan is shown in FIG. 26A. HEK293 cells were infected with AAV2-based dual-vector platforms, RNA was extracted, and gene-specific primers amplified the sequences using PCT. Control digests with BglII (B) and PpuMI (P) revealed the predicted banding pattern shown in FIG. 26B. Undigested (U) PCR product is shown as control and a DNA size marker for reference (M). Separately, products were digested with KpnI and AgeI, and then cloned into pUC57 for sequencing of the entire overlap region FIG. 26C. Ten clones per vector platform were analyzed. M13 forward- and reverse-primers specific for the subclone vector were used to obtain sense and antisense reads (each ~1000 bp) resulting in ~140 bp for which the sense and antisense reads overlapped. PCR=polymerase chain reaction
Figure 26B:
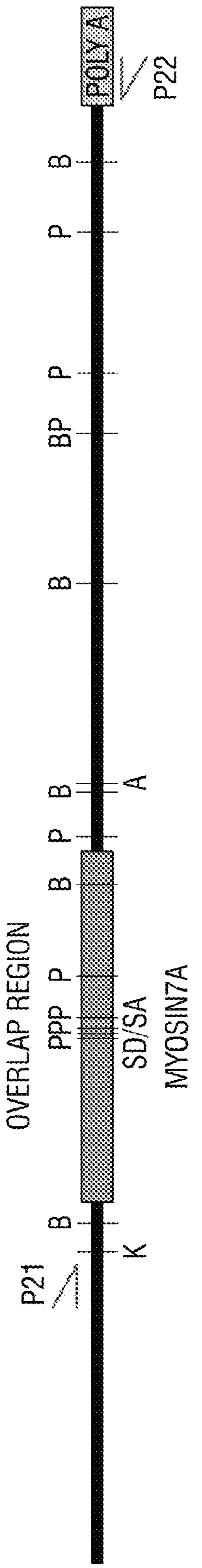
Figure 26C:
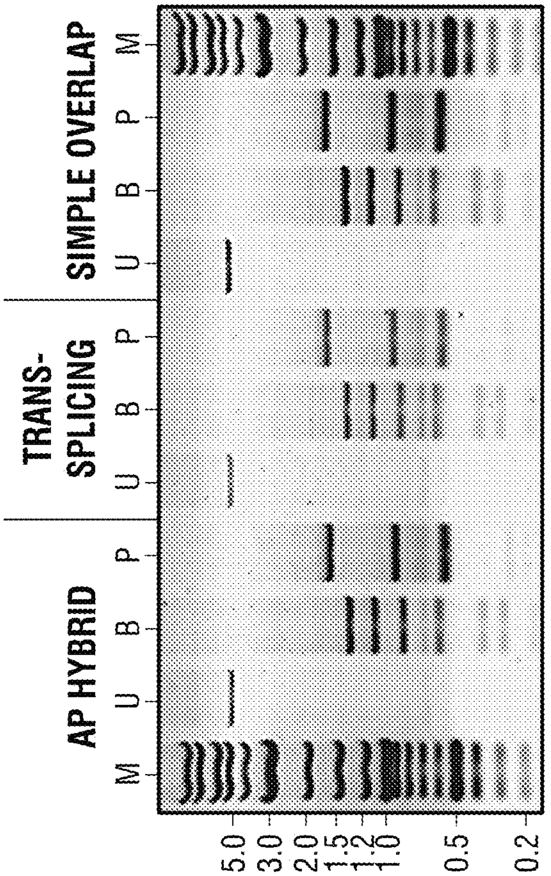
Figure 27A:
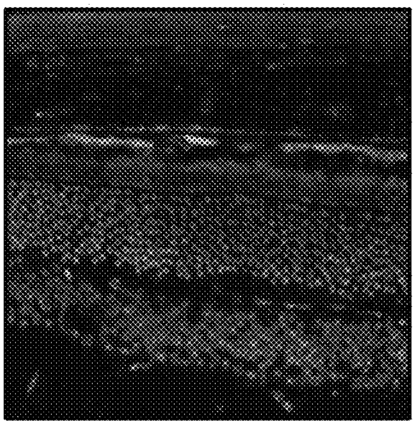
FIG. 27A, FIG. 27B, FIG. 27C, FIG. 27D, FIG. 27E, FIG. 27F, FIG. 27G, and FIG. 27H show the dual vector-mediated MYO7A(HA) expression in vivo. C57BL/6J mice were injected subretinally with AAV2-based dual vectors containing a C' terminal HA tag. Retinal protein expression was analyzed four weeks later by immunohistochemistry and western blot. Ten-micron frozen retinal cross sections were imaged at 10× (FIG. 27A, FIG. 27C, and FIG. 27E) and 60× (FIG. 27B, FIG. 27D, and FIG. 27F). Equal amounts of protein were separated on a 4-15% polyacrylamide gel and stained with an HA antibody (FIG. 27H). For comparison, endogenous MYO7A from C57BL/6J retina (FIG. 27G) was probed with an antibody against MYO7A to confirm that HA-tagged MYO7A migrated at the appropriate size. RPE—retinal pigment epithelium, IS—inner segments, OS—outer segments, ONL—outer nuclear layer, INL—inner nuclear layer, GCL—ganglion cell layer, PR—photoreceptors.
Figure 27B:
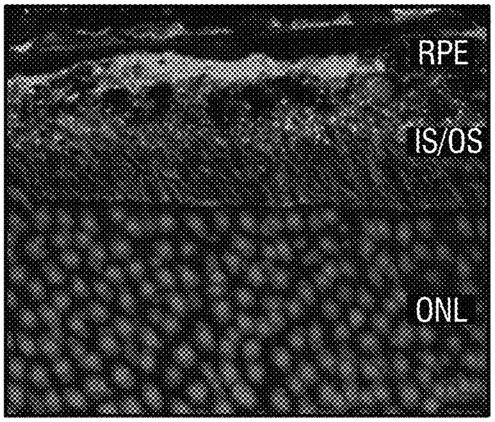
Figure 27C:
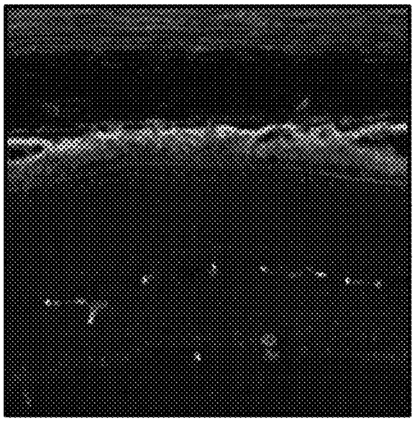
Figure 27D:
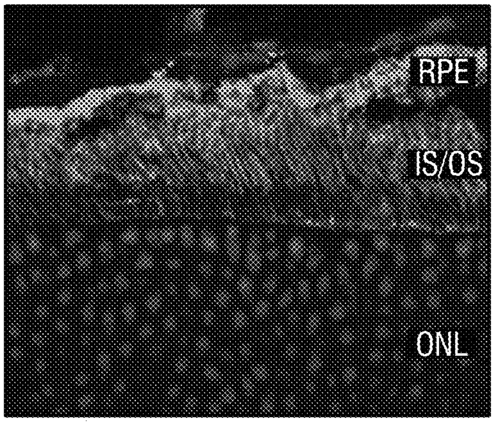
Figure 27E:
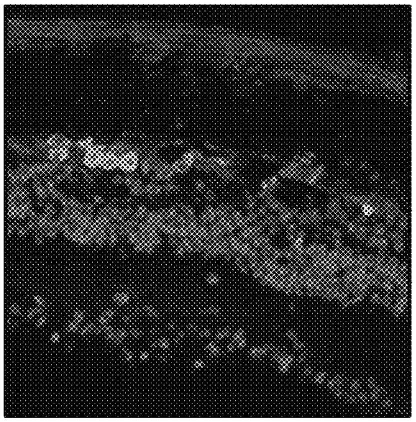
Figure 27F:
Figure 27G:
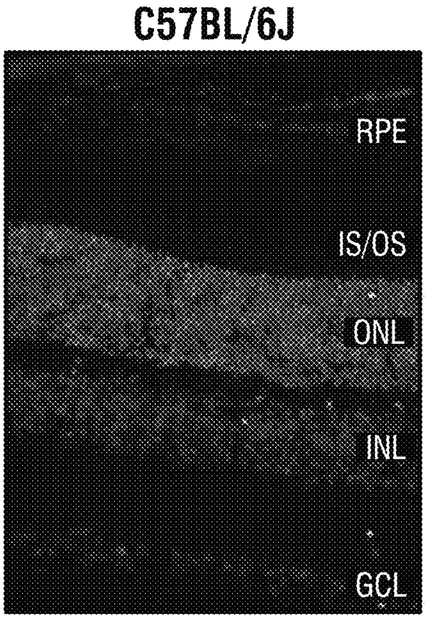
Figure 27H:
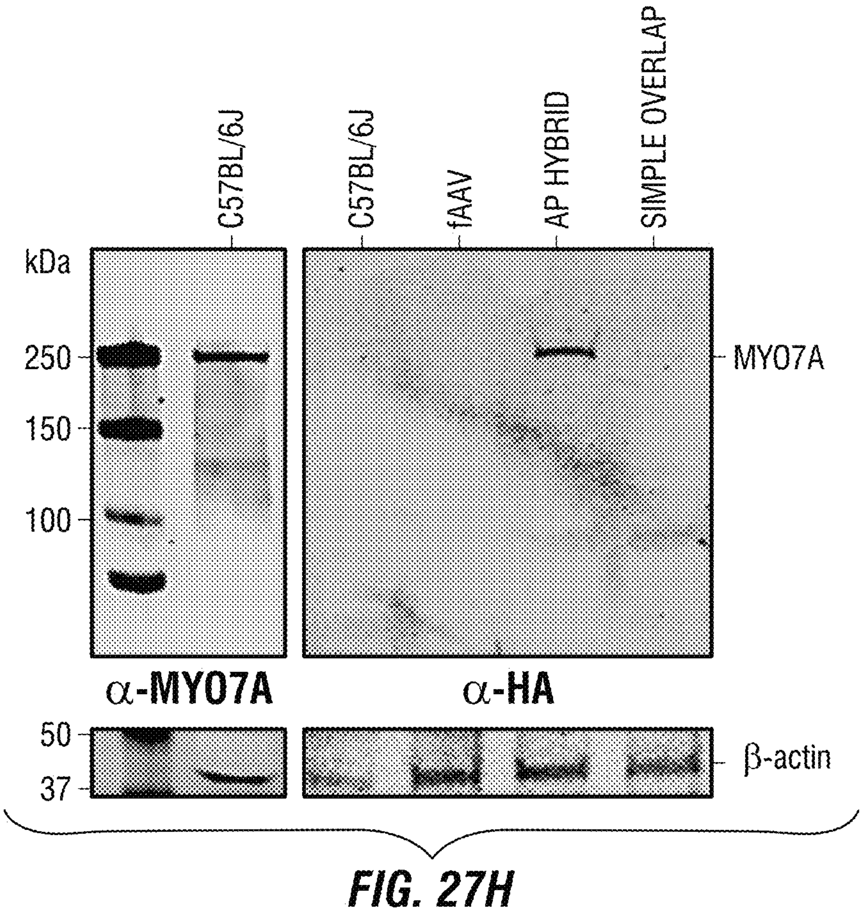

To characterize the fidelity of the mRNA arising from dual vectors, HEK293 cells were infected with dual vectors and RNA extracted, reverse transcribed, and subjected to PCR utilizing primers binding upstream of the overlap region and in the bGH polyA signal region producing a 4.5 kb PCR fragment (FIG. 26A). An identically treated sample not containing reverse transcriptase was used as control for chromosomal DNA contamination. Plasmid containing the full-length MYO7A coding sequence was used as positive control for PCR. A preliminary screen of AAV-mediated MYO7A mRNA was performed by analyzing the pattern of fragment migration on agarose gel following restriction endonuclease digests with PpuMI and BglII (FIG. 26A). Identical banding patterns, consistent with the predicted pattern (PpuMI: 1591, 876, 556, 548, 541, 238, 168, 42, and 36 bp; BglII: 1335, 1074, 827, 583, 360, 272, and 146 bp), were observed following digests of amplicons from each dual-vector platform tested, indicating that no gross alterations (deletions/insertions) occurred as a consequence of either homologous recombination of vector pairs and/or RNA splicing (FIG. 26B). To further characterize the fidelity of the overlap region, a fragment containing the complete overlap area (1829 bp) was restricted and cloned into pUC57 (FIG. 26A). Sequencing results of 10 clones picked at random per vector platform revealed that the overlap region was 100% identical to the consensus/predicted MYO7A sequence (FIG. 26C). This indicated that, in the context of the simple overlap platform, homologous recombination was accurate. Additionally, in the context of trans-splicing vectors, accurate splicing occurred. Finally, for the AP hybrid vectors, a combination of accurate homologous recombination and/or splicing took place. To determine whether this protocol was capable of detecting aberrant sequence in reconstituted MYO7A, a sequence that contained either an insertion of a HindIII recognition site (TAGC) at position 2635 or a point mutation (T-C) at position 2381 was also generated.

MYO7A Expression Mediated by Dual Vectors in Mouse Retina.

To investigate the expression of MYO7A from the two best performing dual-vector platforms in vivo, C57BL/6J mice were subretinally injected with $1\times10^{10}$ vector genomes per eye of simple overlap and AP hybrid systems packaged in AAV8(733) and analyzed 4 weeks later by Western blot and immunohistochemistry. AAV8(733)-fAAV-MYO7A vector was also injected to provide a basis for comparison. To distinguish between endogenous MYO7A and exogenous expression mediated by vectors, sequence coding for an HA tag was added to the C' terminus of the MYO7A cDNA in all constructs. Resulting retinas were immunostained for HA to reveal that fAAV vector along with both dual-vector platforms mediated expression of MYO7A in photoreceptors and RPE. A recent report concluded that simple overlap vectors were more efficient for gene transfer to the RPE than photoreceptors (Trapani et al., 2013). Simple overlap-mediated MYO7A expression was observed in both RPE and photoreceptors. In contrast to previous results showing “spotty” MYO7A expression mediated by AAV2-based simple overlap vectors (Lopes et al., 2013), it was found, when packaged in AAV8(733), that simple overlap vectors mediated MYO7A expression in the majority of RPE and photoreceptor cells. Photoreceptor degeneration/outer nuclear layer thinning was apparent in eyes injected with the AP hybrid vector system. Despite the observed degeneration, AP hybrid-mediated MYO7A was clearly detected in residual PR cell bodies and RPE and was sufficient to be detected by immunoblot. By Western blot analysis using HA antibody, simple overlap-mediated MYO7A was present in just detectable amounts. In contrast, fAAV-mediated protein levels were insufficient to be detected in this assay. Using an antibody against MYO7A, immunoblot of WT mouse retina revealed that both endogenous MYO7A and dual-vector-mediated, HA-tagged MYO7A migrated similarly.

Discussion

In this example, it was shown that dual AAV vectors with defined genetic payloads can be used to deliver a large transgene in vitro and in vivo. The initial experiments using the simplest of all dual-vector platforms revealed that efficiency of AAV2-based simple overlap vectors is proportional to the amount of 5' and 3' vectors used and that MYO7A expression mediated by this system increased as a function of incubation time in HEK293 cells. Next, three distinct dual-vector platforms were evaluated and compared to single, fragmented fAAV vector in vitro. All dual vectors analyzed drove higher levels of MYO7A expression than fAAV. Of all platforms tested, a hybrid vector system containing overlapping, recombinogenic sequence and splice donor/acceptor sites from the AP gene (AP hybrid) was the most efficient.

Regarding the specificity with which the dual-vector platforms express the correct-sized gene product, it was noted in vitro that trans-splicing and hybrid dual-vector platforms generated an additional band of lower molecular weight as detected by immunoblot (monoclonal antibody used was raised against the amino terminus MYO7A). The expression of this truncated product was much more pronounced for infections with 5' vectors alone. What might account for this additional band? After entry into the host cell, the virus capsid is removed and the single-stranded DNA payload is released. The ITRs carried by the single strand serve as primer for DNA polymerases to produce a double strand. The resulting circular intermediates consist mainly of monomers that, over time, convert into multimeric concatemers through intermolecular recombination (Duan et al., 1998; Yang et al., 1999). The dual-vector systems created in this study utilize this strategy to achieve full-length protein expression. A limiting factor lies in the fact that the highly recombinogenic ITRs flanking the expression cassettes are identical in nature leading to a random recombination and consequently a random orientation of the vector parts relative to each other. This random recombination inevitably results in reduced efficiency because only concatemers that have the two vector parts in 5'-3' orientation are able to express the full-length protein. This concatemerization over time is consistent with the observation that the amount of single-vector product is reduced in favor of the full-length protein when both 5' and 3' vectors are combined. Interestingly, the simple overlap system does not generate truncated product, even when only the 5' vector is used for infections. In contrast to the trans-splicing and hybrid vectors, there is virtually no intervening sequence between the end of the MYO7A coding sequence and the right-hand ITR. It may be that splice donor sequences enhance the likelihood of truncated product through some as-yet-to-be-determined mechanism.

A number of strategies have been devised to overcome the issue of random concatemerization and thereby increase specificity as well as efficiency of these dual-vector platforms. First, the addition of a highly-recombinogenic sequence such as that used in the AP hybrid vector here has resulted in significantly increased protein expression compared with the trans-splicing system. Ghosh et al. (2011) provide a detailed analysis of the 270-bp AP sequence used in this study as well as other sequences derived from AP that direct recombination and lead to significant improvement over trans-splicing vectors. The finding that AP hybrid vectors are more efficient than trans-splicing vectors supports that the AP sequence directs at least some of the concatemerization events toward the proper orientation with recombination then occurring via this sequence or via the ITRs. Regardless, with more concatemers properly aligned, the AP hybrid system mediates a more-efficient expression of MYO7A. Another approach for directing concatemerization is the use of single-strand oligonucleotides that are capable of tethering the back end of the 5' vector and the front end of the 3' vector together (Hirsch et al., 2009). However, this strategy requires efficient delivery of the oligonucleotide to the nucleus of the target cells timed with the dual vectors. Finally, dual vectors utilizing mismatched ITRs can be used to direct concatemerization in a head-to-tail orientation (Yan et al., 2005), although the process may require further optimization of the AAV packaging machinery.

Notably, in this study, it was found that the sequence in the overlap region of all dual vectors tested in vitro was 100% identical to the consensus/predicted MYO7A sequence. This indicates that homologous recombination and/or splicing was accurate in each dual-vector platform.

Similar to the in vitro results, the highest levels of MYO7A expression was found in retinas of mice subretinally injected with AAV8-based AP hybrid vectors (as assessed by probing for HA on Western blot). Notably, no truncated proteins were evident in retinas expressing either simple overlap or AP-hybrid mediated MYO7A. The reason for this observed difference remains to be elucidated but may involve differences in the DNA repair machinery that mediate recombination in actively dividing cells versus post-mitotic photoreceptors/RPE (Hirsch et al., 2013). Dual-vector-mediated MYO7A-HA expression was observed in the photoreceptors and RPE of WT mice, locations where MYO7A is thought to have a functional role (Williams and Lopes, 2011). In eyes injected with AP hybrid vectors, marked thinning of the outer nuclear layer was observed. It has previously been shown that vector-mediated overexpression of MYO7A leads to retinal toxicity (Hashimoto et al. 2007). Taken together with the high efficiency of transduction observed in vitro for the AP hybrid platform, the most likely explanation for the observed pathology is excessive production of MYO7A. Despite the marked degeneration, significant amounts of AP hybrid-mediated, full-length MYO7A-HA were detected on Western blot. As high concentrations of vectors were used in these experiments, a simple solution to circumvent toxicity could be to reduce vector genomes injected or replace the strong, ubiquitous smCBA promoter with an endogenous or homologous promoter, and/or a promoter with attenuated strength. An alternative explanation for toxicity of the strong AP hybrid platform is expression of undesired products, like the observed protein expressed from the 5' vectors alone in vitro. However, it was noted that only full-size MYO7A-HA was apparent on Western blot of the AP hybrid-treated retina.

With the goal of developing an AAV-based treatment for USH1B, animal models of this disease have provided an abundance of useful information. Similar to previous observations that fAAV-MYO7A and simple-overlap, dual-vectors were capable of restoring melanosome migration and opsin localization in the shaker1 mouse (Lopes et al., 2013), a recent study by an independent lab confirmed the usefulness of the vectors disclosed herein, when it was reported that they were capable of restoring the ultrastructural retinal phenotypes in the animal model. Notably, shaker1 mice lack retinal degeneration, and the severe functional abnormalities seen in USH1B patients (Liu et al., 1997). This fact renders in vivo analysis of therapeutic outcomes in the shaker1 retina problematic. Alternative animal models for evaluating a treatment for this devastating disease may be useful in adaptation of the present methods to human clinical use.

These results presented here also demonstrated that MYO7A can be efficiently expressed using dual-AAV-vector systems. The platforms containing overlapping elements, namely, the simple overlap system, and the AP hybrid system were both highly efficient. AP hybrid vectors showed the strongest expression of all systems tested, with little observable truncated protein in vitro and none observed in vivo. Simple overlap vectors showed good expression and were the most specific (no truncated protein products were observed) even when the 5'-only vector was used to infect cells. AAV has emerged as the preferred clinical vector and it efficiently transduces both photoreceptors and RPE. Because it has now been demonstrated that MYO7A sequence fidelity is preserved following recombination and/or splicing of dual-AAV-vector platforms and because only full-length MYO7A was detectable in mouse retinas injected with dual vectors, the dual-AAV-vector strategy presented herein represents a valid option for the treatment of retinal disorders associated with mutations in large genes such as USH1B.

REFERENCES

The following references, to the extent that they provide exemplary procedural or other details supplementary to those set forth herein, are specifically incorporated herein by reference:

U.S. Pat. No. 6,204,251.
U.S. Pat. No. 6,461,606.
U.S. Pat. No. 6,106,826.
U.S. Pat. No. 8,137,962.
U.S. Pat. No. 6,967,018.
U.S. Pat. No. 8,298,818.
Allocca, M et al., "Serotype-dependent packaging of large genes in adeno-associated viral vectors results in effective gene delivery in mice," *J. Clin. Invest.,* 118(5):1955-1964 (2008).
Altschul, S F et al., "Basic local alignment search tool," *J. Mol. Biol.,* 215:403-410 (1990).
Altschul, S F et al., "Gapped BLAST and PSI-BLAST: A new generation of protein database search programs," *Nucl. Acids Res.,* 25:3389-3402 (1997).
Astuto, L M et al, "Genetic heterogeneity of Usher syndrome: analysis of 151 families with Usher type 1," *Am. J. Hum. Genet.,* 67:1569-1574 (2000).
Bainbridge, J W et al., "Effect of gene therapy on visual function in Leber's congenital amaurosis," *N. Engl. J. Med.,* 358:2231-2239 (2008).
Beltz, G A et al., "Isolation of multigene families and determination of homologies by filter hybridization methods," *Meth. Enzymol.,* 100:266-285 (1983).
Bharadwaj, A K et al., "Evaluation of the myosin VIIA gene and visual function in patients with Usher syndrome type 1," *Exp. Eye Res.,* 71:173-181 (2000).
Bowles, D E et al., "Phase I gene therapy for Duchenne muscular dystrophy using a translational optimized AAV vector," *Mol. Ther.,* 20:443-455 (2012).
Boye, S E et al., "A comprehensive review of retinal gene therapy." *Mol. Ther.,* 21:509-519 (2013).
Boye, S L et al., "AAV-mediated gene therapy in the guanylate cyclase (RetGC1/RetGC2) double knockout mouse model of Leber congenital amaurosis," *Hum. Gene Ther.,* 24:189-202 (2012).
Boye, S L et al., "Long-term preservation of cone photoreceptors and restoration of cone function by gene therapy in the guanylate cyclase-1 knockout (GC1KO) mouse," *Invest. Ophthalmol. Vis. Sci.* 52:7098-7108 (2011).
Chen, Z Y et al., "Molecular cloning and domain structure of human myosin-VIIa, the gene product defective in Usher syndrome 1B," *Genomics,* 36:440-448 (1996).

Cideciyan, A V et al., "Human RPE65 gene therapy for Leber congenital amaurosis: persistence of early visual improvements and safety at 1 year," *Hum. Gene Ther.,* 20:999-1004 (2009).

Dong, B et al., "Characterization of genome integrity for oversized recombinant AAV vector," *Mol. Ther.,* 18(1): 87-92 (2010).

Duan, D et al., "Circular intermediates of recombinant adeno-associated virus have defined structural characteristics responsible for long-term episomal persistence in muscle tissue," *J. Virol.,* 72:8568-8577 (1998).

Duan, D et al., "Expanding AAV packaging capacity with trans-splicing or overlapping vectors: a quantitative comparison," *Mol. Ther.,* 4:383-391 (2001).

Duan, D et al., "Trans-splicing vectors expand the packaging limits of adeno-associated virus for gene therapy applications," *Methods Mol. Med.,* 76:287-307 (2003).

Dyka, F M et al., "Dual adeno-associated virus vectors result in efficient in vitro and in vivo expression of an oversized gene, MYO7A," *Hum. Gene Ther. Methods,* 25(2): 166-177 (2014).

Esumi, N et al., "Analysis of the VMD2 promoter and implication of E-box binding factors in its regulation," *J. Biol. Chem.,* 279:19064-19073 (2004).

Felgner, P L et al., "Lipofection: a highly efficient, lipid-mediated DNA-transfection procedure," *Proc. Nat'l. Acad. Sci. USA,* 84(21):7413-7417 (1987).

Flotte, T R et al., "Phase 2 clinical trial of a recombinant adeno-associated viral vector expressing alpha1-antitrypsin: interim results," *Hum. Gene Ther.,* 22:1239-1247 (2011).

*Gene Therapy: Principles and Applications*, Blankenstein, T. (Ed.), Birkhauser-Verlag, Basel, Switzerland (1999).

Ghosh, A et al., "A hybrid vector system expands adeno-associated viral vector packaging capacity in a transgene-independent manner," *Mol. Ther.,* 16:124-130 (2008).

Ghosh, A et al., "Efficient transgene reconstitution with hybrid dual AAV vectors carrying the minimized bridging sequences," *Hum. Gene Ther.,* 22:77-83 (2011).

Gibbs, D and Williams, D S, "Isolation and culture of primary mouse retinal pigmented epithlelial cells," *Adv. Exp. Med. Biol.,* 533:347-352 (2003b).

Gibbs, D et al., "Abnormal phagocytosis by retinal pigmented epithelium that lacks myosin VIIa, the Usher syndrome 1B protein," *Proc. Nat'l. Acad. Sci. USA,* 100:6481-6486 (2003a).

Gibbs, D et al., "Role of myosin VIIa and Rab27a in the motility and localization of RPE melanosomes," *J. Cell Sci.,* 117:6473-6483 (2004).

Gibson, F et al., "A type VII myosin encoded by mouse deafness gene shaker-1," *Nature,* 374:62-64 (1995).

Grieger, J C and Samulski, R J, "Packaging capacity of adeno-associated virus serotypes: impact of larger genomes on infectivity and postentry steps," *J. Virol.,* 79:9933-9944 (2005).

Haire, S E et al., "Light-driven cone arrestin translocation in cones of postnatal guanylate cyclase-1 knockout mouse retina treated with AAV-GC1," *Invest. Ophthalmol. Vis. Sci.,* 47:3745-3753 (2006).

Halbert, C L et al., "Efficient mouse airway transduction following recombination between AAV vectors carrying parts of a larger gene," *Nat. Biotechnol.,* 20:697-701 (2002).

Hashimoto, T et al., "Lentiviral gene replacement therapy of retinas in a mouse model for Usher syndrome type 1B," *Gene Ther.,* 14(7):584-594 (2007).

Hasson, T et al., "Effects of shaker-1 mutations on myosin-VIIa protein and mRNA expression," *Cell Motil. Cytoskeleton,* 37:127-138 (1997).

Hasson, T et al., "Expression in cochlea and retina of myosin VIIa, the gene product defective in Usher syndrome type 1B," *Proc. Nat'l. Acad. Sci. USA,* 92:9815-9819 (1995).

Hauswirth, W W et al., "Treatment of leber congenital amaurosis due to RPE65 mutations by ocular subretinal injection of adeno-associated virus gene vector: short-term results of a phase I trial," *Hum. Gene Ther.,* 19:979-990 (2008).

Hirsch, M L et al., "AAV recombineering with single strand oligonucleotides," *PLoS One* 4:e7705 (2009).

Hirsch, M L et al., "Little vector, big gene transduction: fragmented genome reassembly of adeno-associated virus," *Mol. Ther.,* 18(1):6-8 (2010).

Hirsch, M L et al., "Oversized AAV transduction is mediated via a DNA-PKcs-independent, Rad51C-dependent repair pathway," *Mol. Ther.,* 21:2205-2216 (2013).

Jacobson, S G et al., "Retinal disease course in Usher syndrome 1B due to MYO7A mutations," *Invest. Ophthalmol. Vis. Sci.,* 52:7924-7936 (2011).

Jacobson, S G et al., "Safety of recombinant adeno-associated virus type 2-RPE65 vector delivered by ocular subretinal injection," *Molec. Ther.,* 13:1074-1084 (2006).

Jacobson, S G et al., "Usher syndromes due to MYO7A, PCDH15, USH2A or GPR98 mutations share retinal disease mechanism," *Hum. Mol. Genet.,* 17:2405-2415 (2008).

Kapranov, P et al., "Native molecular state of adeno-associated viral vectors revealed by single-molecule sequencing," *Hum. Gene Ther.,* 23:46-55 (2012).

Karlin, S and Altschul, S F "Applications and statistics for multiple high-scoring segments in molecular sequences," *Proc. Nat'l. Acad. Sci. USA,* 90:5873-5877 (1993).

Karlin, S and Altschul, S F, "Methods for assessing the statistical significance of molecular sequence features by using general scoring schemes," *Proc. Nat'l. Acad. Sci. USA,* 87:2264-2268 (1990).

Keats, B J and Corey, D P "The usher syndromes," *Am. J. Med. Genet.,* 89:158-166 (1999).

Klomp, A E et al., "Analysis of the linkage of MYRIP and MYO7A to melanosomes by RAB27A in retinal pigment epithelial cells," *Cell Motil. Cytoskeleton,* 64:474-487 (2007).

Lai, Y et al., "Design of trans-splicing adeno-associated viral vectors for Duchenne muscular dystrophy gene therapy," *Methods Mol. Biol.,* 433:259-275 (2008).

Lai, Y et al., "Efficient in vivo gene expression by trans-splicing adeno-associated viral vectors," *Nat. Biotechnol.,* 23:1435-1439 (2005).

Lai, Y et al., "Evidence for the failure of adeno-associated virus serotype 5 to package a viral genome≥8.2 kb," *Mol. Ther.,* 18(1):75-79 (2010).

Lai, Y et al., "Synthetic intron improves transduction efficiency of trans-splicing, adeno-associated viral vectors," *Hum. Gene Ther.,* 17:1036-1042 (2006).

Li, M et al., "High-efficiency transduction of fibroblasts and mesenchymal stem cells by tyrosine-mutant AAV2 vectors for their potential use in cellular therapy," *Hum. Gene Ther.,* 21:1527-1543 (2010).

Liu, X et al., "Mutant myosin VIIa causes defective melanosome distribution in the RPE of shaker-1 mice," *Nat. Genet.,* 19:117-118 (1998).

Liu, X et al., "Myosin VIIa participates in opsin transport through the photoreceptor cilium," *J. Neurosci.,* 19:6267-6274 (1999).

Liu, X et al., "Myosin VIIa, the product of the Usher 1B syndrome gene, is concentrated in the connecting cilia of photoreceptor cells," *Cell Motil. Cytoskel.,* 37:240-252 (1997).

Liu, X Z et al., "Mutations in the myosin VIIA gene cause non-syndromic recessive deafness," *Nat. Genet.,* 16:188-190 (1997).

Lopes, V S et al., "Retinal gene therapy with a large MYO7A cDNA using adeno-associated virus," *Gene Ther.,* 20:824-833 (2013).

Lopes, V S et al., "The ternary Rab27a-Myrip-Myosin VIIa complex regulates melanosome motility in the retinal pigment epithelium," *Traffic,* 8:486-499 (2007).

Lopes, V S et al., "The Usher 1B protein, MYO7A, is required for normal localization and function of the visual retinoid cycle enzyme, RPE65," *Hum. Mol. Genet.,* 20(13):2560-2570 (2011).

Lostal, W et al., "Efficient recovery of dysferlin deficiency by dual adeno-associated vector-mediated gene transfer," *Hum. Mol. Genet.,* 19:1897-1907 (2010).

Maguire, A M et al., "Age-dependent effects of RPE65 gene therapy for Leber's congenital amaurosis: a phase I dose-escalation trial," *Lancet,* 374:1597-1605 (2009).

Markusic, D M et al., "High-efficiency transduction and correction of murine hemophilia B using AAV2 vectors devoid of multiple surface-exposed tyrosines," *Mol. Ther.,* 18:2048-2056 (2010).

*Molecular Cloning: A Laboratory Manual*, (Maniatis, T, Fritsch, E F, and Sambrook, J), Cold Spring Harbor Laboratory, Cold Spring Harbor, N.Y. (1982).

Nathwani, A C et al., "Adenovirus-associated virus vector-mediated gene transfer in hemophilia B," *N. Engl. J. Med.,* 365:2357-2365 (2011).

Ouyang, X M et al., "Characterization of Usher syndrome type 1 gene mutations in an Usher syndrome patient population," *Hum. Genet.,* 116:292-299 (2005).

Pang, J J et al., "Comparative analysis of in vivo and in vitro AAV vector transduction in the neonatal mouse retina: effects of serotype and site of administration," *Vision Res.,* 48:377-385 (2008).

Petrs-Silva, H et al., "High-efficiency transduction of the mouse retina by tyrosine-mutant AAV serotype vectors." *Mol. Ther.* 17:463-471 (2009).

Petrs-Silva, H et al., "Novel properties of tyrosine-mutant AAV2 vectors in the mouse retina," *Mol. Ther.,* 19:293-301 (2011).

Ryals, R C et al., "Quantifying transduction efficiencies of unmodified and tyrosine capsid mutant AAV vectors in vitro using two ocular cell lines," *Mol. Vis.,* 17:1090-1102 (2011).

Sahly, I et al., "Localization of Usher 1 proteins to the photoreceptor calyceal processes, which are absent from mice," *J. Cell Biol.,* 199:381-399 (2012).

Saihan, Z et al., "Update on Usher syndrome," *Curr. Opin. Neurol.,* 22:19-27 (2009).

Simonelli, F et al., "Gene therapy for Leber's congenital amaurosis is safe and effective through 1.5 years after vector administration," *Mol. Ther.,* 18:643-650 (2010).

Smith, R J et al., "Clinical diagnosis of the Usher syndromes," *Usher Syndrome Consortium. Am. J. Med. Genet.,* 50:32-38 (1994).

Soni, L E et al., "The unconventional myosin-VIIa associates with lysosomes," *Cell Motil. Cytoskeleton,* 62:13-26 (2005).

Timmers, A M et al., "Subretinal injections in rodent eyes: effects on electrophysiology and histology of rat retina," *Mol. Vis.,* 7:131-137 (2001).

Trapani, I et al., "Effective delivery of large genes to the retina by dual AAV vectors," *EMBO Mol. Med.,* 6:194-211 (2013).

Weil, D et al., "Defective myosin VIIA gene responsible for Usher syndrome type 1B," *Nature,* 374:60-61 (1995).

Weil, D et al., "Human myosin VIIA responsible for the Usher 1B syndrome: a predicted membrane-associated motor protein expressed in developing sensory epithelia," *Proc. Nat'l. Acad. Sci. USA,* 93:3232-3237 (1996).

Williams, D S and Lopes, V S "The many different cellular functions of MYO7A in the retina," *Biochem. Soc. Trans.,* 39:1207-1210 (2011).

Williams, D S, "Usher syndrome: Animal models, retinal function of Usher proteins, and prospects for gene therapy," *Vision Res.,* 48:433-441 (2008).

Wolfrum, U et al., "Myosin VIIa as a common component of cilia and microvilli," *Cell Motil. Cytoskeleton,* 40:261-271 (1998).

Wu, Z et al., "Effect of genome size on AAV vector packaging," *Mol. Ther.,* 18(1):80-86 (2010).

Yan, Z et al., "inverted terminal repeat sequences are important for intermolecular recombination and circularization of adeno-associated virus genomes," *J. Virol.,* 79:364-379 (2005).

Yan, Z et al., "Recombinant AAV-mediated gene delivery using dual vector heterodimerization," *Methods Enzymol.,* 346:334-357 (2002).

Yan, Z et al., "Trans-splicing vectors expand the utility of adeno-associated virus for gene therapy," *Proc. Nat'l. Acad. Sci. USA,* 97:6716-6721 (2000).

Yang, J et al., "Concatamerization of adeno-associated virus circular genomes occurs through intermolecular recombination," *J. Virol.,* 73:9468-9477 (1999).

Zhang, Y and Duan, D "Novel mini-dystrophin gene dual adeno-associated virus vectors restore neuronal nitric oxide synthase expression at the sarcolemma," *Hum. Gene Ther.,* 23:98-103 (2012).

Zhong, L et al., "Next generation of adeno-associated virus 2 vectors: point mutations in tyrosines lead to high-efficiency transduction at lower doses," *Proc. Nat'l. Acad. Sci. USA,* 105(22):7827-7832 (2008).

Zolotukhin, S et al., "Production and purification of serotype 1, 2, and 5 recombinant adeno-associated viral vectors," *Methods,* 28:158-167 (2002).

It should be understood that the examples and embodiments described herein are for illustrative purposes only and that various modifications or changes in light thereof will be suggested to persons skilled in the art and are to be included within the spirit and purview of this application and the scope of the appended claims.

All references cited herein (including publications, patent applications and patents) are incorporated by reference to the same extent as if each reference was individually and specifically incorporated by reference, and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order, unless otherwise indicated herein, or unless otherwise clearly contradicted by context.

The use of any examples, or exemplary language (e.g., "such as") provided herein, is intended merely to better illustrate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as “comprising”, “having”, “including” or “containing” with reference to an element or elements is intended to provide support for a similar aspect or embodiment of the invention that “consists of”, “consists essentially of”, or “substantially comprises” that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of ordinary skill in the art that variations may be applied to the compositions and/or methods disclosed herein, and/or to the steps or the sequence of steps of the methods described herein without departing from the concept, spirit and/or scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A hybrid polynucleotide vector system comprising i) a first AAV vector polynucleotide comprising an inverted terminal repeat at each end of the polynucleotide, and between the inverted terminal repeats a promoter followed by a partial coding sequence that encodes an N-terminal part of a selected full-length polypeptide followed by a splice donor site and an intron, and ii) a second AAV vector polynucleotide comprising an inverted terminal repeat at each end of the polynucleotide, and between the inverted terminal repeats an intron and a splice acceptor site for the intron, and optionally followed by a partial coding sequence that encodes a C-terminal part of the selected full-length polypeptide, followed by a polyadenylation (pA) signal sequence, wherein the selected full-length polypeptide is expressed in a photoreceptor cell or a retinal pigment epithelium cell, wherein the intron sequence in the first and second AAV vectors comprises a polynucleotide sequence that overlaps.

2. The polynucleotide vector system of claim 1, wherein the polynucleotide sequence overlap in the intron sequence in the first and second AAV vectors is about 50 to about 500 nucleotides in length.

3. The polynucleotide vector system of claim 1, wherein the promoter is selected from the group consisting of a chimeric CMV β actin (smcBA) promoter, a human myosin 7a gene-derived promoter, a cone transducin a (TαC) gene-derived promoter, a rhodopsin promoter, a cGMP-phosphodiesterase β-subunit promoter, a human rhodopsin kinase (hGRK1) promoter, a rod specific IRBP promoter, a RPE-specific vitelliform macular dystrophy-2 [VMD2] promoter, and combinations thereof.

4. The polynucleotide vector system of claim 1, wherein the selected full-length polypeptide is encoded by a gene of about 5 Kb to about 10 Kb in length.

5. The polynucleotide vector system of claim 1, wherein the first AAV vector polynucleotide comprises the nucleotide sequence of SEQ ID NO:3, and the second AAV vector polynucleotide comprises the nucleotide sequence of SEQ ID NO:4.

6. The polynucleotide vector system of claim 1, wherein the selected full-length polypeptide is a human myosin VIIA polypeptide.

7. The polynucleotide vector system of claim 6, wherein the human myosin VIIa polypeptide comprises the amino acid sequence of SEQ ID NO:6 or SEQ ID NO:8.

8. The polynucleotide vector system of claim 1, wherein the photoreceptor cell comprises a rod cell, a cone cell, or any combination thereof.

9. An isolated host cell comprising the polynucleotide vector system of claim 1.

10. The isolated host cell of claim 9, wherein the cell is a photoreceptor cell, a cone cell, a rod cell, a retinal cell, or any combination thereof.

11. A virus or an infectious viral particle comprising the first AAV vector polynucleotide or the second AAV vector polynucleotide of claim 1.

* * * * *

SEQUENCE LISTING

```
<160> NUMBER OF SEQ ID NOS: 30

<210> SEQ ID NO 1
<211> LENGTH: 7847
<212> TYPE: DNA
<213> ORGANISM: Artificial sequence
<220> FEATURE:
<223> OTHER INFORMATION: the nucleotide of an "hMyo7a coding overlap
      vector A" of the subject invention
<220> FEATURE:
<221> NAME/KEY: exon
<222> LOCATION: (1164)..(1178)

<400> SEQUENCE: 1

cgccaggctg caggggggggg ggggggggg ttggccactc cctctctgcg cgctcgctcg     60

ctcactgagg ccgggcgacc aaaggtcgcc cgacgcccgg gctttgcccg ggcggcctca    120

gtgagcgagc gagcgcgcag agagggagtg gccaactcca tcactagggg ttcctcagat    180

ctggcgcgcc caattcggta ccctagttat taatagtaat caattacggg gtcattagtt    240

catagcccat atatggagtt ccgcgttaca taacttacgg taaatggccc gcctggctga    300

ccgcccaacg acccccgccc attgacgtca ataatgacgt atgttcccat agtaacgcca    360

atagggactt tccattgacg tcaatgggtg gactatttac ggtaaactgc ccacttggca    420

gtacatcaag tgtatcatat gccaagtacg ccccctattg acgtcaatga cggtaaatgg    480

cccgcctggc attatgccca gtacatgacc ttatgggact ttcctacttg gcagtacatc    540

tacgtattag tcatcgctat taccatggtc gaggtgagcc ccacgttctg cttcactctc    600

cccatctccc ccccctcccc acccccaatt ttgtatttat ttatttttta attattttgt    660

gcagcgatgg gggcgggggg gggggggggg cgcgcgccag gcggggcggg gcggggcgag    720

gggcggggcg gggcgaggcg gagaggtgcg gcggcagcca atcagagcgg cgcgctccga    780

aagtttcctt ttatggcgag gcggcggcgg cggcggccct ataaaaagcg aagcgcgcgg    840

cgggcgggag tcgctgcgac gctgccttcg ccccgtgccc cgctccgccg ccgcctcgcg    900

ccgcccgccc cggctctgac tgaccgcgtt actcccacag gtgagcgggc gggacggccc    960

ttctcctccg ggctgtaatt agcgcttggt ttaatgacgg cttgtttctt ttctgtggct   1020

gcgtgaaagc cttgaggggc tccgggagct agagcctctg ctaaccatgt tcatgccttc   1080

ttcttttcc tacagctcct gggcaacgtg ctggttattg tgctgtctca tcattttggc   1140

aaagaattct agcggccgcc acc atg gtg att ctt cag caggggggacc          1188
                          Met Val Ile Leu Gln
                          1               5
```

-continued

```
atgtgtggat ggacctgaga ttggggcagg agttcgacgt gcccatcggg gcggtggtga   1248
agctctgcga ctctgggcag gtccaggtgg tggatgatga agacaatgaa cactggatct   1308
ctccgcagaa cgcaacgcac atcaagccta tgcaccccac gtcggtccac ggcgtggagg   1368
acatgatccg cctgggggac ctcaacgagg cgggcatctt gcgcaacctg cttatccgct   1428
accgggacca cctcatctac acgtatacgg gctccatcct ggtggctgtg aacccctacc   1488
agctgctctc catctactcg ccagagcaca tccgccagta taccaacaag aagattgggg   1548
agatgccccc ccacatcttt gccattgctg acaactgcta cttcaacatg aaacgcaaca   1608
gccgagacca gtgctgcatc atcagtgggg aatctggggc cgggaagacg gagagcacaa   1668
agctgatcct gcagttcctg gcagccatca gtgggcagca ctcgtggatt gagcagcagg   1728
tcttggaggc caccccccatt ctggaagcat ttgggaatgc caagaccatc cgcaatgaca   1788
actcaagccg tttcggaaag tacatcgaca tccacttcaa caagcggggc gccatcgagg   1848
gcgcgaagat tgagcagtac ctgctggaaa agtcacgtgt ctgtcgccag gccctggatg   1908
aaaggaacta ccacgtgttc tactgcatgc tggagggtat gagtgaggat cagaagaaga   1968
agctgggctt gggccaggcc tctgactaca actacttggc catgggtaac tgcataacct   2028
gtgagggccg ggtggacagc caggagtacg ccaacatccg ctccgccatg aaggtgctca   2088
tgttcactga caccgagaac tgggagatct cgaagctcct ggctgccatc ctgcacctgg   2148
gcaacctgca gtatgaggca cgcacatttg aaaacctgga tgcctgtgag gttctcttct   2208
ccccatcgct ggccacagct gcatccctgc ttgaggtgaa ccccccagac ctgatgagct   2268
gcctgactag ccgcaccctc atcacccgcg gggagacggt gtccacccca ctgagcaggg   2328
aacaggcact ggacgtgcgc gacgccttcg taaaggggat ctacgggcgg ctgttcgtgt   2388
ggattgtgga caagatcaac gcagcaattt acaagcctcc ctcccaggat gtgaagaact   2448
ctcgcaggtc catcggcctc ctggacatct ttgggtttga gaactttgct gtgaacagct   2508
ttgagcagct ctgcatcaac ttcgccaatg agcacctgca gcagttcttt gtgcggcacg   2568
tgttcaagct ggagcaggag gaatatgacc tggagagcat tgactggctg cacatcgagt   2628
tcactgacaa ccaggatgcc ctggacatga ttgccaacaa gcccatgaac atcatctccc   2688
tcatcgatga ggagagcaag ttccccaagg gcacagacac caccatgtta cacaagctga   2748
actcccagca caagctcaac gccaactaca tcccccccaa gaacaaccat gagacccagt   2808
ttggcatcaa ccattttgca ggcatcgtct actatgagac ccaaggcttc ctggagaaga   2868
accgagacac cctgcatggg gacattatcc agctggtcca ctcctccagg aacaagttca   2928
tcaagcagat cttccaggcc gatgtcgcca tgggcgccga gaccaggaag cgctcgccca   2988
cacttagcag ccagttcaag cggtcactgg agctgctgat gcgcacgctg ggtgcctgcc   3048
agcccttctt tgtgcgatgc atcaagccca atgagttcaa gaagcccatg ctgttcgacc   3108
ggcacctgtg cgtgcgccag ctgcggtact caggaatgat ggagaccatc cgaatccgcc   3168
gagctggcta ccccatccgc tacagcttcg tagagtttgt ggagcggtac cgtgtgctgc   3228
tgccaggtgt gaagccggcc tacaagcagg gcgacctccg cgggacttgc cagcgcatgg   3288
ctgaggctgt gctgggcacc cacgatgact ggcagatagg caaaaccaag atctttctga   3348
aggaccacca tgacatgctg ctggaagtgg agcgggacaa agccatcacc gacagagtca   3408
tcctccttca gaaagtcatc cggggattca aagacaggtc taactttctg aagctgaaga   3468
acgctgccac actgatccag aggcactggc ggggtcacaa ctgtaggaag aactacgggc   3528
```

-continued

```
tgatgcgtct gggcttcctg cggctgcagg ccctgcaccg ctcccggaag ctgcaccagc   3588
agtaccgcct ggcccgccag cgcatcatcc agttccaggc ccgctgccgc gcctatctgg   3648
tgcgcaaggc cttccgccac cgcctctggg ctgtgctcac cgtgcaggcc tatgcccggg   3708
gcatgatcgc ccgcaggctg caccaacgcc tcagggctga gtatctgtgg cgcctcgagg   3768
ctgagaaaat gcggctggcg gaggaagaga agcttcggaa ggagatgagc gccaagaagg   3828
ccaaggagga ggccgagcgc aagcatcagg agcgcctggc ccagctggct cgtgaggacg   3888
ctgagcggga gctgaaggag aaggaggccg ctcggcggaa gaaggagctc ctggagcaga   3948
tggaaagggc ccgccatgag cctgtcaatc actcagacat ggtggacaag atgtttggct   4008
tcctggggac ttcaggtggc ctgccaggcc aggagggcca ggcacctagt ggctttgagg   4068
acctggagcg agggcggagg gagatggtgg aggaggacct ggatgcagcc ctgcccctgc   4128
ctgacgagga tgaggaggac ctctctgagt ataaatttgc caagttcgcg gccacctact   4188
tccaggggac aaccacgcac tcctacaccc ggcggccact caaacagcca ctgctctacc   4248
atgacgacga gggtgaccag ctggcagccc tggcggtctg gatcaccatc ctccgcttca   4308
tgggggacct ccctgagccc aagtaccaca cagccatgag tgatggcagt gagaagatcc   4368
ctgtgatgac caagatttat gagaccctgg gcaagaagac gtacaagagg gagctgcagg   4428
ccctgcaggg cgagggcgag gcccagctcc ccgagggcca gaagaagagc agtgtgaggc   4488
acaagctggt gcatttgact ctgaaaaaga agtccaagct cacagaggag gtgaccaaga   4548
ggctgcatga cggggagtcc acagtgcagg gcaacagcat gctggaggac cggcccacct   4608
ccaacctgga gaagctgcac ttcatcatcg gcaatggcat cctgcggcca gcactccggg   4668
acgagatcta ctgccagatc agcaagcagc tgacccacaa cccctccaag agcagctatg   4728
cccggggctg gattctcgtg tctctctgcg tgggctgttt cgccccctcc gagaagtttg   4788
tcaagtacct gcggaacttc gctagcgggc actagtccgt cgactgttaa ttaagcatgc   4848
tggggagaga tctaggaacc cctagtgatg gagttggcca ctccctctct gcgcgctcgc   4908
tcgctcactg aggccgcccg ggcaaagccc gggcgtcggg cgacctttgg tcgcccggcc   4968
tcagtgagcg agcgagcgcg cagagaggga gtggccaacc cccccccccc ccccccctgca   5028
gccctgcatt aatgaatcgg ccaacgcgcg gggagaggcg gtttgcgtat tgggcgctct   5088
tccgcttcct cgctcactga ctcgctgcgc tcggtcgttc ggctgcggcg agcggtatca   5148
gctcactcaa aggcggtaat acggttatcc acagaatcag gggataacgc aggaaagaac   5208
atgtgagcaa aaggccagca aaaggccagg aaccgtaaaa aggccgcgtt gctggcgttt   5268
ttccataggc tccgcccccc tgacgagcat cacaaaaatc gacgctcaag tcagaggtgg   5328
cgaaacccga caggactata aagataccag gcgtttcccc ctggaagctc cctcgtgcgc   5388
tctcctgttc cgaccctgcc gcttaccgga tacctgtccg cctttctccc ttcgggaagc   5448
gtggcgcttt ctcaatgctc acgctgtagg tatctcagtt cggtgtaggt cgttcgctcc   5508
aagctgggct gtgtgcacga accccccgtt cagcccgacc gctgcgcctt atccggtaac   5568
tatcgtcttg agtccaaccc ggtaagacac gacttatcgc cactggcagc agccactggt   5628
aacaggatta gcagagcgag gtatgtaggc ggtgctacag agttcttgaa gtggtggcct   5688
aactacggct acactagaag gacagtattt ggtatctgcg ctctgctgaa gccagttacc   5748
ttcggaaaaa gagttggtag ctcttgatcc ggcaaacaaa ccaccgctgg tagcggtggt   5808
tttttgttt gcaagcagca gattacgcgc agaaaaaaag gatctcaaga agatcctttg   5868
atcttttcta cggggtctga cgctcagtgg aacgaaaact cacgttaagg gattttggtc   5928
```

atgagattat caaaaaggat cttcacctag atccttttaa attaaaaatg aagttttaaa 5988 tcaatctaaa gtatatatga gtaaacttgg tctgacagtt accaatgctt aatcagtgag 6048 gcacctatct cagcgatctg tctatttcgt tcatccatag ttgcctgact ccccgtcgtg 6108 tagataacta cgatacggga gggcttacca tctggcccca gtgctgcaat gataccgcga 6168 gacccacgct caccggctcc agatttatca gcaataaacc agccagccgg aagggccgag 6228 cgcagaagtg gtcctgcaac tttatccgcc tccatccagt ctattaattg ttgccgggaa 6288 gctagagtaa gtagttcgcc agttaatagt ttgcgcaacg ttgttgccat tgctacaggc 6348 atcgtggtgt cacgctcgtc gtttggtatg gcttcattca gctccggttc ccaacgatca 6408 aggcgagtta catgatcccc catgttgtgc aaaaaagcgg ttagctcctt cggtcctccg 6468 atcgttgtca gaagtaagtt ggccgcagtg ttatcactca tggttatggc agcactgcat 6528 aattctctta ctgtcatgcc atccgtaaga tgcttttctg tgactggtga gtactcaacc 6588 aagtcattct gagaatagtg tatgcggcga ccgagttgct cttgcccggc gtcaatacgg 6648 gataataccg cgccacatag cagaacttta aaagtgctca tcattggaaa acgttcttcg 6708 gggcgaaaac tctcaaggat cttaccgctg ttgagatcca gttcgatgta acccactcgt 6768 gcacccaact gatcttcagc atcttttact ttcaccagcg tttctgggtg agcaaaaaca 6828 ggaaggcaaa atgccgcaaa aaagggaata agggcgacac ggaaatgttg aatactcata 6888 ctcttccttt ttcaatatta ttgaagcatt tatcagggtt attgtctcat gagcggatac 6948 atatttgaat gtatttagaa aaataaacaa ataggggttc cgcgcacatt tccccgaaaa 7008 gtgccacctg acgtctaaga aaccattatt atcatgacat taacctataa aaataggcgt 7068 atcacgaggc cctttcgtct cgcgcgtttc ggtgatgacg gtgaaaacct ctgacacatg 7128 cagctcccgg agacggtcac agcttgtctg taagcggatg ccgggagcag acaagcccgt 7188 cagggcgcgt cagcgggtgt tggcgggtgt cggggctggc ttaactatgc ggcatcagag 7248 cagattgtac tgagagtgca ccatatgcgg tgtgaaatac cgcacagatg cgtaaggaga 7308 aaataccgca tcaggaaatt gtaaacgtta atattttgtt aaaattcgcg ttaaattttt 7368 gttaaatcag ctcatttttt aaccaatagg ccgaaatcgg caaaatccct tataaatcaa 7428 aagaatagac cgagataggg ttgagtgttg ttccagtttg gaacaagagt ccactattaa 7488 agaacgtgga ctccaacgtc aaagggcgaa aaaccgtcta tcagggcgat ggcccactac 7548 gtgaaccatc accctaatca agttttttgg ggtcgaggtg ccgtaaagca ctaaatcgga 7608 accctaaagg gagcccccga tttagagctt gacggggaaa gccggcgaac gtggcgagaa 7668 aggaagggaa gaaagcgaaa ggagcgggcg ctagggcgct ggcaagtgta gcggtcacgc 7728 tgcgcgtaac caccacaccc gccgcgctta atgcgccgct acagggcgcg tcgcgccatt 7788 cgccattcag gctacgcaac tgttgggaag ggcgatcggt gcgggcctct tcgctatta 7847

<210> SEQ ID NO 2
<211> LENGTH: 7779
<212> TYPE: DNA
<213> ORGANISM: Artificial sequence
<220> FEATURE:
<223> OTHER INFORMATION: the nucleotide of an “hMyo7a coding overlap vector B” of the subject invention

<400> SEQUENCE: 2
aggggggggg gggggggggt tggccactcc ctctctgcgc gctcgctcgc tcactgaggc 60
cgggcgacca aaggtcgccc gacgcccggg ctttgcccgg gcggcctcag tgagcgagcg 120

```
agcgcgcaga gagggagtgg ccaactccat cactaggggt tcctcagatc tggcgcgccc    180
aattggcttc gaattctagc ggccgctgct taagcaggtc taactttctg aagctgaaga    240
acgctgccac actgatccag aggcactggc ggggtcacaa ctgtaggaag aactacgggc    300
tgatgcgtct gggcttcctg cggctgcagg ccctgcaccg ctcccggaag ctgcaccagc    360
agtaccgcct ggcccgccag cgcatcatcc agttccaggc ccgctgccgc gcctatctgg    420
tgcgcaaggc cttccgccac cgcctctggg ctgtgctcac cgtgcaggcc tatgcccggg    480
gcatgatcgc ccgcaggctg caccaacgcc tcagggctga gtatctgtgg cgcctcgagg    540
ctgagaaaat gcggctggcg gaggaagaga agcttcggaa ggagatgagc gccaagaagg    600
ccaaggagga ggccgagcgc aagcatcagg agcgcctggc ccagctggct cgtgaggacg    660
ctgagcggga gctgaaggag aaggaggccg ctcggcggaa gaaggagctc ctggagcaga    720
tggaaagggc ccgccatgag cctgtcaatc actcagacat ggtggacaag atgtttggct    780
tcctggggac ttcaggtggc ctgccaggcc aggagggcca ggcacctagt ggctttgagg    840
acctggagcg agggcggagg gagatggtgg aggaggacct ggatgcagcc ctgcccctgc    900
ctgacgagga tgaggaggac ctctctgagt ataaatttgc caagttcgcg gccacctact    960
tccaggggac aaccacgcac tcctacaccc ggcggccact caaacagcca ctgctctacc   1020
atgacgacga gggtgaccag ctggcagccc tggcggtctg gatcaccatc ctccgcttca   1080
tgggggacct ccctgagccc aagtaccaca cagccatgag tgatggcagt gagaagatcc   1140
ctgtgatgac caagatttat gagaccctgg gcaagaagac gtacaagagg gagctgcagg   1200
ccctgcaggg cgagggcgag gcccagctcc ccgagggcca gaagaagagc agtgtgaggc   1260
acaagctggt gcatttgact ctgaaaaaga agtccaagct cacagaggag gtgaccaaga   1320
ggctgcatga cggggagtcc acagtgcagg gcaacagcat gctggaggac cggcccacct   1380
ccaacctgga gaagctgcac ttcatcatcg gcaatggcat cctgcggcca gcactccggg   1440
acgagatcta ctgccagatc agcaagcagc tgacccacaa cccctccaag agcagctatg   1500
cccggggctg gattctcgtg tctctctgcg tgggctgttt cgccccctcc gagaagtttg   1560
tcaagtacct gcggaacttc atccacgggg gcccgcccgg ctacgccccg tactgtgagg   1620
agcgcctgag aaggaccttt gtcaatggga cacggacaca gccgcccagc tggctggagc   1680
tgcaggccac caagtccaag aagccaatca tgttgcccgt gacattcatg gatgggacca   1740
ccaagaccct gctgacggac tcggcaacca cggccaagga gctctgcaac gcgctggccg   1800
acaagatctc tctcaaggac cggttcgggt tctccctcta cattgccctg tttgacaagg   1860
tgtcctccct gggcagcggc agtgaccacg tcatggacgc catctcccag tgcgagcagt   1920
acgccaagga gcagggcgcc caggagcgca acgcccccctg gaggctcttc ttccgcaaag   1980
aggtcttcac gccctggcac agcccctccg aggacaacgt ggccaccaac ctcatctacc   2040
agcaggtggt gcgaggagtc aagtttgggg agtacaggtg tgagaaggag gacgacctgg   2100
ctgagctggc ctcccagcag tactttgtag actatggctc tgagatgatc ctggagcgcc   2160
tcctgaacct cgtgcccacc tacatccccg accgcgagat cacgcccctg aagacgctgg   2220
agaagtgggc ccagctggcc atcgccgccc acaagaaggg gatttatgcc cagaggagaa   2280
ctgatgccca gaaggtcaaa gaggatgtgg tcagttatgc ccgcttcaag tggcccttgc   2340
tcttctccag gttttatgaa gcctacaaat tctcaggccc cagtctcccc aagaacgacg   2400
tcatcgtggc cgtcaactgg acgggtgtgt actttgtgga tgagcaggag caggtacttc   2460
```

-continued tggagctgtc cttcccagag atcatggccg tgtccagcag caggggagcg aaaacgacgg 2520
cccccagctt cacgctggcc accatcaagg gggacgaata caccttcacc tccagcaatg 2580
ctgaggacat tcgtgacctg gtggtcacct tcctagaggg gctccggaag agatctaagt 2640
atgttgtggc cctgcaggat aaccccaacc ccgcaggcga ggagtcaggc ttcctcagct 2700
ttgccaaggg agacctcatc atcctggacc atgacacggg cgagcaggtc atgaactcgg 2760
gctgggccaa cggcatcaat gagaggacca agcagcgtgg ggacttcccc accgacagtg 2820
tgtacgtcat gcccactgtc accatgccac cgcgggagat tgtggccctg gtcaccatga 2880
ctcccgatca gaggcaggac gttgtccggc tcttgcagct gcgaacggcg gagcccgagg 2940
tgcgtgccaa gccctacacg ctggaggagt tttcctatga ctacttcagg cccccaccca 3000
agcacacgct gagccgtgtc atggtgtcca aggcccgagg caaggaccgg ctgtggagcc 3060
acacgcggga accgctcaag caggcgctgc tcaagaagct cctgggcagt gaggagctct 3120
cgcaggaggc ctgcctggcc ttcattgctg tgctcaagta catgggcgac tacccgtcca 3180
agaggacacg ctccgtcaac gagctcaccg accagatctt tgagggtccc ctgaaagccg 3240
agcccctgaa ggacgaggca tatgtgcaga tcctgaagca gctgaccgac aaccacatca 3300
ggtacagcga ggagcggggt tgggagctgc tctggctgtg cacgggcctt ttcccaccca 3360
gcaacatcct cctgccccac gtgcagcgct tcctgcagtc ccgaaagcac tgcccactcg 3420
ccatcgactg cctgcaacgg ctccagaaag ccctgagaaa cgggtcccgg aagtaccctc 3480
cgcacctggt ggaggtggag gccatccagc acaagaccac ccagattttc cacaaagtct 3540
acttccctga tgacactgac gaggccttcg aagtggagtc cagcaccaag gccaaggact 3600
tctgccagaa catcgccacc aggctgctcc tcaagtcctc agagggattc agcctctttg 3660
tcaaaattgc agacaaggtc atcagcgttc ctgagaatga cttcttcttt gactttgttc 3720
gacacttgac agactggata aagaaagctc ggcccatcaa ggacggaatt gtgccctcac 3780
tcacctacca ggtgttcttc atgaagaagc tgtggaccac cacggtgcca gggaaggatc 3840
ccatggccga ttccatcttc cactattacc aggagttgcc caagtatctc cgaggctacc 3900
acaagtgcac gcgggaggag gtgctgcagc tgggggcgct gatctacagg gtcaagttcg 3960
aggaggacaa gtcctacttc cccagcatcc ccaagctgct gcgggagctg gtgccccagg 4020
accttatccg gcaggtctca cctgatgact ggaagcggtc catcgtcgcc tacttcaaca 4080
agcacgcagg gaagtccaag gaggaggcca agctggcctt cctgaagctc atcttcaagt 4140
ggcccacctt tggctcagcc ttcttcgagg tgaagcaaac tacggagcca aacttccctg 4200
agatcctcct aattgccatc aacaagtatg gggtcagcct catcgatccc aaaacgaagg 4260
atatcctcac cactcatccc ttcaccaaga tctccaactg gagcagcggc aacacctact 4320
tccacatcac cattgggaac ttggtgcgcg ggagcaaact gctctgcgag acgtcactgg 4380
gctacaagat ggatgacctc ctgacttcct acattagcca gatgctcaca gccatgagca 4440
aacagcgggg ctccaggagc ggcaagtgag gtaccaaggg cgaattctgc agtcgactag 4500
agctcgctga tcagcctcga ctgtgccttc tagttgccag ccatctgttg tttgcccctc 4560
ccccgtgcct tccttgaccc tggaaggtgc cactcccact gtcctttcct aataaaatga 4620
ggaaattgca tcgcattgtc tgagtaggtg tcattctatt ctggggggtg gggtggggca 4680
ggacagcaag ggggaggatt gggaagacaa tagcaggcat gctggggaga gatctgagga 4740
ctagtccgtc gactgttaat taagcatgct ggggagagat ctaggaaccc ctagtgatgg 4800
agttggccac tccctctctg cgcgctcgct cgctcactga ggccgcccgg gcaaagcccg 4860
ggcgtcgggc gacctttggt cgcccggcct cagtgagcga gcgagcgcgc agagagggag 4920
tggccaaccc cccccccccc cccccctgcag ccctgcatta atgaatcggc caacgcgcgg 4980
ggagaggcgg tttgcgtatt gggcgctctt ccgcttcctc gctcactgac tcgctgcgct 5040
cggtcgttcg gctgcggcga gcggtatcag ctcactcaaa ggcggtaata cggttatcca 5100
cagaatcagg ggataacgca ggaaagaaca tgtgagcaaa aggccagcaa aaggccagga 5160
accgtaaaaa ggccgcgttg ctggcgtttt tccataggct ccgcccccct gacgagcatc 5220
acaaaaatcg acgctcaagt cagaggtggc gaaacccgac aggactataa agataccagg 5280
cgtttccccc tggaagctcc ctcgtgcgct ctcctgttcc gaccctgccg cttaccggat 5340
acctgtccgc ctttctccct tcgggaagcg tggcgctttc tcaatgctca cgctgtaggt 5400
atctcagttc ggtgtaggtc gttcgctcca agctgggctg tgtgcacgaa ccccccgttc 5460
agcccgaccg ctgcgcctta tccggtaact atcgtcttga gtccaacccg gtaagacacg 5520
acttatcgcc actggcagca gccactggta acaggattag cagagcgagg tatgtaggcg 5580
gtgctacaga gttcttgaag tggtggccta actacggcta cactagaagg acagtatttg 5640
gtatctgcgc tctgctgaag ccagttacct tcggaaaaag agttggtagc tcttgatccg 5700
gcaaacaaac caccgctggt agcggtggtt tttttgtttg caagcagcag attacgcgca 5760
gaaaaaaagg atctcaagaa gatcctttga tcttttctac ggggtctgac gctcagtgga 5820
acgaaaactc acgttaaggg attttggtca tgagattatc aaaaaggatc ttcacctaga 5880
tccttttaaa ttaaaaatga agttttaaat caatctaaag tatatatgag taaacttggt 5940
ctgacagtta ccaatgctta atcagtgagg cacctatctc agcgatctgt ctatttcgtt 6000
catccatagt tgcctgactc cccgtcgtgt agataactac gatacgggag ggcttaccat 6060
ctggccccag tgctgcaatg ataccgcgag acccacgctc accggctcca gatttatcag 6120
caataaacca gccagccgga agggccgagc gcagaagtgg tcctgcaact ttatccgcct 6180
ccatccagtc tattaattgt tgccgggaag ctagagtaag tagttcgcca gttaatagtt 6240
tgcgcaacgt tgttgccatt gctacaggca tcgtggtgtc acgctcgtcg tttggtatgg 6300
cttcattcag ctccggttcc caacgatcaa ggcgagttac atgatccccc atgttgtgca 6360
aaaaagcggt tagctccttc ggtcctccga tcgttgtcag aagtaagttg gccgcagtgt 6420
tatcactcat ggttatggca gcactgcata attctcttac tgtcatgcca tccgtaagat 6480
gcttttctgt gactggtgag tactcaacca agtcattctg agaatagtgt atgcggcgac 6540
cgagttgctc ttgcccggcg tcaatacggg ataataccgc gccacatagc agaactttaa 6600
aagtgctcat cattggaaaa cgttcttcgg ggcgaaaact ctcaaggatc ttaccgctgt 6660
tgagatccag ttcgatgtaa cccactcgtg cacccaactg atcttcagca tcttttactt 6720
tcaccagcgt ttctgggtga gcaaaaacag gaaggcaaaa tgccgcaaaa aagggaataa 6780
gggcgacacg gaaatgttga atactcatac tcttcctttt tcaatattat tgaagcattt 6840
atcagggtta ttgtctcatg agcggataca tatttgaatg tatttagaaa aataaacaaa 6900
taggggttcc gcgcacattt ccccgaaaag tgccacctga cgtctaagaa accattatta 6960
tcatgacatt aacctataaa aataggcgta tcacgaggcc ctttcgtctc gcgcgtttcg 7020
gtgatgacgg tgaaaacctc tgacacatgc agctcccgga gacggtcaca gcttgtctgt 7080
aagcggatgc cgggagcaga caagcccgtc agggcgcgtc agcgggtgtt ggcgggtgtc 7140
ggggctggct taactatgcg gcatcagagc agattgtact gagagtgcac catatgcggt 7200

-continued

```
gtgaaatacc gcacagatgc gtaaggagaa aataccgcat caggaaattg taaacgttaa   7260

tattttgtta aaattcgcgt taaatttttg ttaaatcagc tcatttttta accaataggc   7320

cgaaatcggc aaaatccctt ataaatcaaa agaatagacc gagatagggt tgagtgttgt   7380

tccagtttgg aacaagagtc cactattaaa gaacgtggac tccaacgtca aagggcgaaa   7440

aaccgtctat cagggcgatg gcccactacg tgaaccatca ccctaatcaa gttttttggg   7500

gtcgaggtgc cgtaaagcac taaatcggaa ccctaaaggg agcccccgat ttagagcttg   7560

acggggaaag ccggcgaacg tggcgagaaa ggaagggaag aaagcgaaag gagcgggcgc   7620

tagggcgctg gcaagtgtag cggtcacgct gcgcgtaacc accacacccg ccgcgcttaa   7680

tgcgccgcta cagggcgcgt cgcgccattc gccattcagg ctacgcaact gttgggaagg   7740

gcgatcggtg cgggcctctt cgctattacg ccaggctgc                          7779


<210> SEQ ID NO 3
<211> LENGTH: 7405
<212> TYPE: DNA
<213> ORGANISM: Artificial sequence
<220> FEATURE:
<223> OTHER INFORMATION: the nucleotide of an “hMyo7a intron 23 splicing
      vector A” of the subject invention
<220> FEATURE:
<221> NAME/KEY: exon
<222> LOCATION: (1153)..(1167)

<400> SEQUENCE: 3

aggggggggg gggggggggt tggccactcc ctctctgcgc gctcgctcgc tcactgaggc     60

cgggcgacca aaggtcgccc gacgcccggg ctttgcccgg gcggcctcag tgagcgagcg    120

agcgcgcaga gagggagtgg ccaactccat cactaggggt tcctcagatc tggcgcgccc    180

aattcggtac cctagttatt aatagtaatc aattacgggg tcattagttc atagcccata    240

tatggagttc cgcgttacat aacttacggt aaatggcccg cctggctgac cgcccaacga    300

cccccgccca ttgacgtcaa taatgacgta tgttcccata gtaacgccaa tagggacttt    360

ccattgacgt caatgggtgg actatttacg gtaaactgcc cacttggcag tacatcaagt    420

gtatcatatg ccaagtacgc cccctattga cgtcaatgac ggtaaatggc ccgcctggca    480

ttatgcccag tacatgacct tatgggactt tcctacttgg cagtacatct acgtattagt    540

catcgctatt accatggtcg aggtgagccc cacgttctgc ttcactctcc ccatctcccc    600

cccctcccca cccccaattt tgtatttatt tattttttaa ttattttgtg cagcgatggg    660

ggcggggggg gggggggggc gcgcgccagg cggggcgggg cggggcgagg ggcggggcgg    720

ggcgaggcgg agaggtgcgg cggcagccaa tcagagcggc gcgctccgaa agtttccttt    780

tatggcgagg cggcggcggc ggcggcccta taaaaagcga agcgcgcggc gggcgggagt    840

cgctgcgacg ctgccttcgc cccgtgcccc gctccgccgc cgcctcgcgc cgcccgcccc    900

ggctctgact gaccgcgtta ctcccacagg tgagcgggcg ggacggccct tctcctccgg    960

gctgtaatta gcgcttggtt taatgacggc ttgtttcttt tctgtggctg cgtgaaagcc   1020

ttgaggggct ccgggagcta gagcctctgc taaccatgtt catgccttct tcttttccct   1080

acagctcctg ggcaacgtgc tggttattgt gctgtctcat cattttggca aagaattcta   1140

gcggccgcca cc atg gtg att ctt cag cagggggacc atgtgtggat             1187
              Met Val Ile Leu Gln
              1               5

ggacctgaga ttggggcagg agttcgacgt gcccatcggg gcggtggtga agctctgcga   1247

ctctgggcag gtccaggtgg tggatgatga agacaatgaa cactggatct ctccgcagaa   1307
```

cgcaacgcac atcaagccta tgcaccccac gtcggtccac ggcgtggagg acatgatccg 1367
cctgggggac ctcaacgagg cgggcatctt gcgcaacctg cttatccgct accgggacca 1427
cctcatctac acgtatacgg gctccatcct ggtggctgtg aacccctacc agctgctctc 1487
catctactcg ccagagcaca tccgccagta taccaacaag aagattgggg agatgccccc 1547
ccacatcttt gccattgctg acaactgcta cttcaacatg aaacgcaaca gccgagacca 1607
gtgctgcatc atcagtgggg aatctggggc cgggaagacg gagagcacaa agctgatcct 1667
gcagttcctg gcagccatca gtgggcagca ctcgtggatt gagcagcagg tcttggaggc 1727
cacccccatt ctggaagcat ttgggaatgc caagaccatc cgcaatgaca actcaagccg 1787
tttcggaaag tacatcgaca tccacttcaa caagcggggc gccatcgagg gcgcgaagat 1847
tgagcagtac ctgctggaaa agtcacgtgt ctgtcgccag gccctggatg aaaggaacta 1907
ccacgtgttc tactgcatgc tggagggtat gagtgaggat cagaagaaga agctgggctt 1967
gggccaggcc tctgactaca actacttggc catgggtaac tgcataacct gtgagggccg 2027
ggtggacagc caggagtacg ccaacatccg ctccgccatg aaggtgctca tgttcactga 2087
caccgagaac tgggagatct cgaagctcct ggctgccatc ctgcacctgg gcaacctgca 2147
gtatgaggca cgcacatttg aaaacctgga tgcctgtgag gttctcttct ccccatcgct 2207
ggccacagct gcatccctgc ttgaggtgaa ccccccagac ctgatgagct gcctgactag 2267
ccgcaccctc atcacccgcg gggagacggt gtccacccca ctgagcaggg aacaggcact 2327
ggacgtgcgc gacgccttcg taaaggggat ctacgggcgg ctgttcgtgt ggattgtgga 2387
caagatcaac gcagcaattt acaagcctcc ctcccaggat gtgaagaact ctcgcaggtc 2447
catcggcctc ctggacatct ttgggtttga gaactttgct gtgaacagct ttgagcagct 2507
ctgcatcaac ttcgccaatg agcacctgca gcagttcttt gtgcggcacg tgttcaagct 2567
ggagcaggag gaatatgacc tggagagcat tgactggctg cacatcgagt tcactgacaa 2627
ccaggatgcc ctggacatga ttgccaacaa gcccatgaac atcatctccc tcatcgatga 2687
ggagagcaag ttccccaagg gcacagacac caccatgtta cacaagctga actcccagca 2747
caagctcaac gccaactaca tcccccccaa gaacaaccat gagacccagt ttggcatcaa 2807
ccattttgca ggcatcgtct actatgagac ccaaggcttc ctggagaaga accgagacac 2867
cctgcatggg gacattatcc agctggtcca ctcctccagg aacaagttca tcaagcagat 2927
cttccaggcc gatgtcgcca tgggcgccga gaccaggaag cgctcgccca cacttagcag 2987
ccagttcaag cggtcactgg agctgctgat gcgcacgctg ggtgcctgcc agcccttctt 3047
tgtgcgatgc atcaagccca atgagttcaa gaagcccatg ctgttcgacc ggcacctgtg 3107
cgtgcgccag ctgcggtact caggaatgat ggagaccatc cgaatccgcc gagctggcta 3167
ccccatccgc tacagcttcg tagagtttgt ggagcggtac cgtgtgctgc tgccaggtgt 3227
gaagccggcc tacaagcagg gcgacctccg cgggacttgc cagcgcatgg ctgaggctgt 3287
gctgggcacc cacgatgact ggcagatagg caaaaccaag atctttctga aggaccacca 3347
tgacatgctg ctggaagtgg agcgggacaa agccatcacc gacagagtca tcctccttca 3407
gaaagtcatc cggggattca aagacaggtc taactttctg aagctgaaga acgctgccac 3467
actgatccag aggcactggc ggggtcacaa ctgtaggaag aactacgggc tgatgcgtct 3527
gggcttcctg cggctgcagg ccctgcaccg ctcccggaag ctgcaccagc agtaccgcct 3587
ggcccgccag cgcatcatcc agttccaggc ccgctgccgc gcctatctgg tgcgcaaggc 3647

-continued

```
cttccgccac cgcctctggg ctgtgctcac cgtgcaggcc tatgcccggg gcatgatcgc   3707
ccgcaggctg caccaacgcc tcagggctga gtatctgtgg cgcctcgagg ctgagaaaat   3767
gcggctggcg gaggaagaga agcttcggaa ggagatgagc gccaagaagg ccaaggagga   3827
ggccgagcgc aagcatcagg agcgcctggc ccagctggct cgtgaggacg ctgagcggga   3887
gctgaaggag aaggaggccg ctcggcggaa gaaggagctc ctggagcaga tggaaagggc   3947
ccgccatgag cctgtcaatc actcagacat ggtggacaag atgtttggct tcctggggac   4007
ttcaggtggc ctgccaggcc aggagggcca ggcacctagt ggctttgagg taccaggcta   4067
gggacagggg ctccagaggc ccacacacac cgcttgtgtt gatcctccct ccttctgtgc   4127
ccttggcctt aaagcccacc cagtccctct gaacagtggg gagcagagat gaactgggtc   4187
cgggctgcag gtcccaggtc ctgtccctct ccaacgccct tctcaagttt ttttttttgt   4247
tttttttttt tttttttttt ttgagatggg gtcgtaccct gttgctcagg ctggagtgca   4307
gtagcgtgat cacagctcac tgcagccttg aacttctggg ctcaggcggc tagcgggcac   4367
tagtccgtcg actgttaatt aagcatgctg gggagagatc taggaacccc tagtgatgga   4427
gttggccact ccctctctgc gcgctcgctc gctcactgag gccgcccggg caaagcccgg   4487
gcgtcgggcg acctttggtc gcccggcctc agtgagcgag cgagcgcgca gagagggagt   4547
ggccaacccc cccccccccc cccctgcagc cctgcattaa tgaatcggcc aacgcgcggg   4607
gagaggcggt ttgcgtattg ggcgctcttc cgcttcctcg ctcactgact cgctgcgctc   4667
ggtcgttcgg ctgcggcgag cggtatcagc tcactcaaag gcggtaatac ggttatccac   4727
agaatcaggg gataacgcag gaaagaacat gtgagcaaaa ggccagcaaa aggccaggaa   4787
ccgtaaaaag gccgcgttgc tggcgttttt ccataggctc cgcccccctg acgagcatca   4847
caaaaatcga cgctcaagtc agaggtggcg aaacccgaca ggactataaa gataccaggc   4907
gtttccccct ggaagctccc tcgtgcgctc tcctgttccg accctgccgc ttaccggata   4967
cctgtccgcc tttctccctt cgggaagcgt ggcgctttct caatgctcac gctgtaggta   5027
tctcagttcg gtgtaggtcg ttcgctccaa gctgggctgt gtgcacgaac cccccgttca   5087
gcccgaccgc tgcgccttat ccggtaacta tcgtcttgag tccaacccgg taagacacga   5147
cttatcgcca ctggcagcag ccactggtaa caggattagc agagcgaggt atgtaggcgg   5207
tgctacagag ttcttgaagt ggtggcctaa ctacggctac actagaagga cagtatttgg   5267
tatctgcgct ctgctgaagc cagttacctt cggaaaaaga gttggtagct cttgatccgg   5327
caaacaaacc accgctggta gcggtggttt ttttgtttgc aagcagcaga ttacgcgcag   5387
aaaaaaagga tctcaagaag atcctttgat cttttctacg gggtctgacg ctcagtggaa   5447
cgaaaactca cgttaaggga ttttggtcat gagattatca aaaaggatct tcacctagat   5507
ccttttaaat taaaaatgaa gttttaaatc aatctaaagt atatatgagt aaacttggtc   5567
tgacagttac caatgcttaa tcagtgaggc acctatctca gcgatctgtc tatttcgttc   5627
atccatagtt gcctgactcc ccgtcgtgta gataactacg atacgggagg gcttaccatc   5687
tggccccagt gctgcaatga taccgcgaga cccacgctca ccggctccag atttatcagc   5747
aataaaccag ccagccggaa gggccgagcg cagaagtggt cctgcaactt tatccgcctc   5807
catccagtct attaattgtt gccgggaagc tagagtaagt agttcgccag ttaatagttt   5867
gcgcaacgtt gttgccattg ctacaggcat cgtggtgtca cgctcgtcgt ttggtatggc   5927
ttcattcagc tccggttccc aacgatcaag gcgagttaca tgatccccca tgttgtgcaa   5987
aaaagcggtt agctccttcg gtcctccgat cgttgtcaga agtaagttgg ccgcagtgtt   6047
```

-continued

```
atcactcatg gttatggcag cactgcataa ttctcttact gtcatgccat ccgtaagatg   6107

cttttctgtg actggtgagt actcaaccaa gtcattctga gaatagtgta tgcggcgacc   6167

gagttgctct tgcccggcgt caatacggga taataccgcg ccacatagca gaactttaaa   6227

agtgctcatc attggaaaac gttcttcggg gcgaaaactc tcaaggatct taccgctgtt   6287

gagatccagt tcgatgtaac ccactcgtgc acccaactga tcttcagcat cttttacttt   6347

caccagcgtt tctgggtgag caaaaacagg aaggcaaaat gccgcaaaaa agggaataag   6407

ggcgacacgg aaatgttgaa tactcatact cttccttttt caatattatt gaagcattta   6467

tcagggttat tgtctcatga gcggatacat atttgaatgt atttagaaaa ataaacaaat   6527

aggggttccg cgcacatttc cccgaaaagt gccacctgac gtctaagaaa ccattattat   6587

catgacatta acctataaaa ataggcgtat cacgaggccc tttcgtctcg cgcgtttcgg   6647

tgatgacggt gaaaacctct gacacatgca gctcccggag acggtcacag cttgtctgta   6707

agcggatgcc gggagcagac aagcccgtca gggcgcgtca gcgggtgttg gcgggtgtcg   6767

gggctggctt aactatgcgg catcagagca gattgtactg agagtgcacc atatgcggtg   6827

tgaaataccg cacagatgcg taaggagaaa ataccgcatc aggaaattgt aaacgttaat   6887

attttgttaa aattcgcgtt aaatttttgt taaatcagct cattttttaa ccaataggcc   6947

gaaatcggca aaatccctta taaatcaaaa gaatagaccg agatagggtt gagtgttgtt   7007

ccagtttgga acaagagtcc actattaaag aacgtggact ccaacgtcaa agggcgaaaa   7067

accgtctatc agggcgatgg cccactacgt gaaccatcac cctaatcaag ttttttgggg   7127

tcgaggtgcc gtaaagcact aaatcggaac cctaaaggga gcccccgatt tagagcttga   7187

cggggaaagc cggcgaacgt ggcgagaaag gaagggaaga aagcgaaagg agcgggcgct   7247

agggcgctgg caagtgtagc ggtcacgctg cgcgtaacca ccacacccgc cgcgcttaat   7307

gcgccgctac agggcgcgtc gcgccattcg ccattcaggc tacgcaactg ttgggaaggg   7367

cgatcggtgc gggcctcttc gctattacgc caggctgc                           7405
```

<210> SEQ ID NO 4
<211> LENGTH: 7477
<212> TYPE: DNA
<213> ORGANISM: Artificial sequence
<220> FEATURE:
<223> OTHER INFORMATION: the nucleotide of an “hMyo7a intron 23 splicing vector B” of the subject invention

<400> SEQUENCE: 4

```
cgccaggctg caggggggggg gggggggggg ttggccactc cctctctgcg cgctcgctcg     60

ctcactgagg ccgggcgacc aaaggtcgcc cgacgcccgg gctttgcccg ggcggcctca    120

gtgagcgagc gagcgcgcag agagggagtg gccaactcca tcactagggg ttcctcagat    180

ctggcgcgcc caattggctt cgaattctag cggccgctgc ttaagcaccg cttgtgttga    240

tcctccctcc ttctgtgccc ttggccttaa agcccaccca gtccctctga acagtgggga    300

gcagagatga actgggtccg ggctgcaggt cccaggtcct gtccctctcc aacgcccttc    360

tcaagttttt ttttttgttt tttttttttt tttttttttt gagatggggt cgtaccctgt    420

tgctcaggct ggagtgcagt agcgtgatca cagctcactg cagccttgaa cttctgggct    480

caggcgatcc tcccacctga gcttcctgag tagctgggac tccagggcat acctcttgtc    540

tccttcagga cctggagcga gggcggaggg agatggtgga ggaggacctg gatgcagccc    600

tgcccctgcc tgacgaggat gaggaggacc tctctgagta taaatttgcc aagttcgcgg    660
```

-continued

```
ccacctactt ccaggggaca accacgcact cctacacccg gcggccactc aaacagccac    720
tgctctacca tgacgacgag ggtgaccagc tggcagccct ggcggtctgg atcaccatcc    780
tccgcttcat gggggacctc cctgagccca agtaccacac agccatgagt gatggcagtg    840
agaagatccc tgtgatgacc aagatttatg agaccctggg caagaagacg tacaagaggg    900
agctgcaggc cctgcagggc gagggcgagg cccagctccc cgagggccag aagaagagca    960
gtgtgaggca caagctggtg catttgactc tgaaaaagaa gtccaagctc acagaggagg   1020
tgaccaagag gctgcatgac ggggagtcca cagtgcaggg caacagcatg ctggaggacc   1080
ggcccacctc caacctggag aagctgcact tcatcatcgg caatggcatc ctgcggccag   1140
cactccggga cgagatctac tgccagatca gcaagcagct gacccacaac ccctccaaga   1200
gcagctatgc ccggggctgg attctcgtgt ctctctgcgt gggctgtttc gccccctccg   1260
agaagtttgt caagtacctg cggaacttca tccacggggg cccgcccggc tacgccccgt   1320
actgtgagga gcgcctgaga aggacctttg tcaatgggac acggacacag ccgcccagct   1380
ggctggagct gcaggccacc aagtccaaga agccaatcat gttgcccgtg acattcatgg   1440
atgggaccac caagaccctg ctgacggact cggcaaccac ggccaaggag ctctgcaacg   1500
cgctggccga caagatctct ctcaaggacc ggttcgggtt ctccctctac attgccctgt   1560
ttgacaaggt gtcctccctg ggcagcggca gtgaccacgt catggacgcc atctcccagt   1620
gcgagcagta cgccaaggag cagggcgccc aggagcgcaa cgcccccctgg aggctcttct   1680
tccgcaaaga ggtcttcacg ccctggcaca gcccctccga ggacaacgtg gccaccaacc   1740
tcatctacca gcaggtggtg cgaggagtca agtttgggga gtacaggtgt gagaaggagg   1800
acgacctggc tgagctggcc tcccagcagt actttgtaga ctatggctct gagatgatcc   1860
tggagcgcct cctgaacctc gtgcccacct acatccccga ccgcgagatc acgcccctga   1920
agacgctgga gaagtgggcc cagctggcca tcgccgccca caagaagggg atttatgccc   1980
agaggagaac tgatgcccag aaggtcaaag aggatgtggt cagttatgcc cgcttcaagt   2040
ggcccttgct cttctccagg ttttatgaag cctacaaatt ctcaggcccc agtctcccca   2100
agaacgacgt catcgtggcc gtcaactgga cgggtgtgta ctttgtggat gagcaggagc   2160
aggtacttct ggagctgtcc ttcccagaga tcatggccgt gtccagcagc aggggagcga   2220
aaacgacggc cccagcttc acgctggcca ccatcaaggg ggacgaatac accttcacct   2280
ccagcaatgc tgaggacatt cgtgacctgg tggtcacctt cctagagggg ctccggaaga   2340
gatctaagta tgttgtggcc ctgcaggata accccaaccc cgcaggcgag gagtcaggct   2400
tcctcagctt tgccaaggga gacctcatca tcctggacca tgacacgggc gagcaggtca   2460
tgaactcggg ctgggccaac ggcatcaatg agaggaccaa gcagcgtggg gacttcccca   2520
ccgacagtgt gtacgtcatg cccactgtca ccatgccacc gcgggagatt gtggccctgg   2580
tcaccatgac tcccgatcag aggcaggacg ttgtccggct cttgcagctg cgaacggcgg   2640
agcccgaggt gcgtgccaag ccctacacgc tggaggagtt ttcctatgac tacttcaggc   2700
ccccacccaa gcacacgctg agccgtgtca tggtgtccaa ggcccgaggc aaggaccggc   2760
tgtggagcca cacgcgggaa ccgctcaagc aggcgctgct caagaagctc ctgggcagtg   2820
aggagctctc gcaggaggcc tgcctggcct tcattgctgt gctcaagtac atgggcgact   2880
acccgtccaa gaggacacgc tccgtcaacg agctcaccga ccagatcttt gagggtcccc   2940
tgaaagccga gcccctgaag gacgaggcat atgtgcagat cctgaagcag ctgaccgaca   3000
```

-continued

```
accacatcag gtacagcgag gagcggggtt gggagctgct ctggctgtgc acgggccttt   3060
tcccacccag caacatcctc ctgccccacg tgcagcgctt cctgcagtcc cgaaagcact   3120
gcccactcgc catcgactgc ctgcaacggc tccagaaagc cctgagaaac gggtcccgga   3180
agtaccctcc gcacctggtg gaggtggagg ccatccagca caagaccacc cagattttcc   3240
acaaagtcta cttccctgat gacactgacg aggccttcga agtggagtcc agcaccaagg   3300
ccaaggactt ctgccagaac atcgccacca ggctgctcct caagtcctca gagggattca   3360
gcctctttgt caaaattgca gacaaggtca tcagcgttcc tgagaatgac ttcttctttg   3420
actttgttcg acacttgaca gactggataa agaaagctcg gcccatcaag gacggaattg   3480
tgccctcact cacctaccag gtgttcttca tgaagaagct gtggaccacc acggtgccag   3540
ggaaggatcc catggccgat tccatcttcc actattacca ggagttgccc aagtatctcc   3600
gaggctacca caagtgcacg cgggaggagg tgctgcagct gggggcgctg atctacaggg   3660
tcaagttcga ggaggacaag tcctacttcc ccagcatccc caagctgctg cgggagctgg   3720
tgccccagga ccttatccgg caggtctcac ctgatgactg gaagcggtcc atcgtcgcct   3780
acttcaacaa gcacgcaggg aagtccaagg aggaggccaa gctggccttc ctgaagctca   3840
tcttcaagtg gcccaccttt ggctcagcct tcttcgaggt gaagcaaact acggagccaa   3900
acttccctga gatcctccta attgccatca acaagtatgg ggtcagcctc atcgatccca   3960
aaacgaagga tatcctcacc actcatccct tcaccaagat ctccaactgg agcagcggca   4020
acacctactt ccacatcacc attgggaact tggtgcgcgg gagcaaactg ctctgcgaga   4080
cgtcactggg ctacaagatg gatgacctcc tgacttccta cattagccag atgctcacag   4140
ccatgagcaa acagcggggc tccaggagcg gcaagtgagg taccaagggc gaattctgca   4200
gtcgactaga gctcgctgat cagcctcgac tgtgccttct agttgccagc catctgttgt   4260
ttgcccctcc cccgtgcctt ccttgaccct ggaaggtgcc actcccactg tcctttccta   4320
ataaaatgag gaaattgcat cgcattgtct gagtaggtgt cattctattc tggggggtgg   4380
ggtggggcag gacagcaagg gggaggattg ggaagacaat agcaggcatg ctggggagag   4440
atctgaggac tagtccgtcg actgttaatt aagcatgctg gggagagatc taggaacccc   4500
tagtgatgga gttggccact ccctctctgc gcgctcgctc gctcactgag gccgcccggg   4560
caaagcccgg gcgtcgggcg acctttggtc gcccggcctc agtgagcgag cgagcgcgca   4620
gagagggagt ggccaacccc cccccccccc cccctgcagc cctgcattaa tgaatcggcc   4680
aacgcgcggg gagaggcggt ttgcgtattg ggcgctcttc cgcttcctcg ctcactgact   4740
cgctgcgctc ggtcgttcgg ctgcggcgag cggtatcagc tcactcaaag gcggtaatac   4800
ggttatccac agaatcaggg gataacgcag gaaagaacat gtgagcaaaa ggccagcaaa   4860
aggccaggaa ccgtaaaaag gccgcgttgc tggcgttttt ccataggctc cgcccccctg   4920
acgagcatca caaaaatcga cgctcaagtc agaggtggcg aaacccgaca ggactataaa   4980
gataccaggc gtttccccct ggaagctccc tcgtgcgctc tcctgttccg accctgccgc   5040
ttaccggata cctgtccgcc tttctccctt cgggaagcgt ggcgctttct caatgctcac   5100
gctgtaggta tctcagttcg gtgtaggtcg ttcgctccaa gctgggctgt gtgcacgaac   5160
cccccgttca gcccgaccgc tgcgccttat ccggtaacta tcgtcttgag tccaacccgg   5220
taagacacga cttatcgcca ctggcagcag ccactggtaa caggattagc agagcgaggt   5280
atgtaggcgg tgctacagag ttcttgaagt ggtggcctaa ctacggctac actagaagga   5340
cagtatttgg tatctgcgct ctgctgaagc cagttacctt cggaaaaaga gttggtagct   5400
```

-continued

```
cttgatccgg caaacaaacc accgctggta gcggtggttt ttttgtttgc aagcagcaga   5460
ttacgcgcag aaaaaaagga tctcaagaag atcctttgat cttttctacg gggtctgacg   5520
ctcagtggaa cgaaaactca cgttaaggga ttttggtcat gagattatca aaaaggatct   5580
tcacctagat ccttttaaat taaaaatgaa gttttaaatc aatctaaagt atatatgagt   5640
aaacttggtc tgacagttac caatgcttaa tcagtgaggc acctatctca gcgatctgtc   5700
tatttcgttc atccatagtt gcctgactcc ccgtcgtgta gataactacg atacgggagg   5760
gcttaccatc tggccccagt gctgcaatga taccgcgaga cccacgctca ccggctccag   5820
atttatcagc aataaaccag ccagccggaa gggccgagcg cagaagtggt cctgcaactt   5880
tatccgcctc catccagtct attaattgtt gccgggaagc tagagtaagt agttcgccag   5940
ttaatagttt gcgcaacgtt gttgccattg ctacaggcat cgtggtgtca cgctcgtcgt   6000
ttggtatggc ttcattcagc tccggttccc aacgatcaag gcgagttaca tgatccccca   6060
tgttgtgcaa aaaagcggtt agctccttcg gtcctccgat cgttgtcaga agtaagttgg   6120
ccgcagtgtt atcactcatg gttatggcag cactgcataa ttctcttact gtcatgccat   6180
ccgtaagatg cttttctgtg actggtgagt actcaaccaa gtcattctga gaatagtgta   6240
tgcggcgacc gagttgctct tgcccggcgt caatacggga taataccgcg ccacatagca   6300
gaactttaaa agtgctcatc attggaaaac gttcttcggg gcgaaaactc tcaaggatct   6360
taccgctgtt gagatccagt tcgatgtaac ccactcgtgc acccaactga tcttcagcat   6420
cttttacttt caccagcgtt tctgggtgag caaaaacagg aaggcaaaat gccgcaaaaa   6480
agggaataag ggcgacacgg aaatgttgaa tactcatact cttccttttt caatattatt   6540
gaagcattta tcagggttat tgtctcatga gcggatacat atttgaatgt atttagaaaa   6600
ataaacaaat aggggttccg cgcacatttc cccgaaaagt gccacctgac gtctaagaaa   6660
ccattattat catgacatta acctataaaa ataggcgtat cacgaggccc tttcgtctcg   6720
cgcgtttcgg tgatgacggt gaaaacctct gacacatgca gctcccggag acggtcacag   6780
cttgtctgta agcggatgcc gggagcagac aagcccgtca gggcgcgtca gcgggtgttg   6840
gcgggtgtcg gggctggctt aactatgcgg catcagagca gattgtactg agagtgcacc   6900
atatgcggtg tgaaataccg cacagatgcg taaggagaaa ataccgcatc aggaaattgt   6960
aaacgttaat attttgttaa aattcgcgtt aaatttttgt taaatcagct cattttttaa   7020
ccaataggcc gaaatcggca aaatccctta taaatcaaaa gaatagaccg agatagggtt   7080
gagtgttgtt ccagtttgga acaagagtcc actattaaag aacgtggact ccaacgtcaa   7140
agggcgaaaa accgtctatc agggcgatgg cccactacgt gaaccatcac cctaatcaag   7200
ttttttgggg tcgaggtgcc gtaaagcact aaatcggaac cctaaaggga gcccccgatt   7260
tagagcttga cggggaaagc cggcgaacgt ggcgagaaag gaagggaaga aagcgaaagg   7320
agcgggcgct agggcgctgg caagtgtagc ggtcacgctg cgcgtaacca ccacacccgc   7380
cgcgcttaat gcgccgctac agggcgcgtc gcgccattcg ccattcaggc tacgcaactg   7440
ttgggaaggg cgatcggtgc gggcctcttc gctatta                            7477
```

<210> SEQ ID NO 5
<211> LENGTH: 7465
<212> TYPE: DNA
<213> ORGANISM: Homo sapiens

<400> SEQUENCE: 5

-continued

```
gctctgggca ggagagagag tgagagacaa gagacacaca cagagagacg gcgaggaagg     60
gaaagaccca gagggacgcc tagaacgaga cttggagcca gacagaggaa gaggggacgt    120
gtgtttgcag actggctggg cccgtgaccc agcttcctga gtcctccgtg caggtggcag    180
ctgtaccagg ctggcaggtc actgagagtg ggcagctggg ccccagaact gtgcctggcc    240
cagtgggcag caggagctcc tgacttggga ccatggtgat tcttcagcag gggaccatg     300
tgtggatgga cctgagattg ggcaggagt tcgacgtgcc catcggggcg gtggtgaagc     360
tctgcgactc tgggcaggtc caggtggtgg atgatgaaga caatgaacac tggatctctc    420
cgcagaacgc aacgcacatc aagcctatgc accccacgtc ggtccacggc gtggaggaca    480
tgatccgcct gggggacctc aacgaggcgg gcatcttgcg caacctgctt atccgctacc    540
gggaccacct catctacacg tatacgggct ccatcctggt ggctgtgaac ccctaccagc    600
tgctctccat ctactcgcca gagcacatcc gccagtatac caacaagaag attggggaga    660
tgcccccccca catctttgcc attgctgaca actgctactt caacatgaaa cgcaacagcc    720
gagaccagtg ctgcatcatc agtggggaat ctggggccgg gaagacggag agcacaaagc    780
tgatcctgca gttcctggca gccatcagtg ggcagcactc gtggattgag cagcaggtct    840
tggaggccac ccccattctg gaagcatttg ggaatgccaa gaccatccgc aatgacaact    900
caagccgttt cggaaagtac atcgacatcc acttcaacaa gcggggcgcc atcgagggcg    960
cgaagattga gcagtacctg ctggaaaagt cacgtgtctg tcgccaggcc ctggatgaaa   1020
ggaactacca cgtgttctac tgcatgctgg agggtatgag tgaggatcag aagaagaagc   1080
tgggcttggg ccaggcctct gactacaact acttggccat gggtaactgc ataacctgtg   1140
agggccgggt ggacagccag gagtacgcca acatccgctc cgccatgaag gtgctcatgt   1200
tcactgacac cgagaactgg gagatctcga agctcctggc tgccatcctg cacctgggca   1260
acctgcagta tgaggcacgc acatttgaaa acctggatgc ctgtgaggtt ctcttctccc   1320
catcgctggc cacagctgca tccctgcttg aggtgaaccc cccagacctg atgagctgcc   1380
tgactagccg caccctcatc acccgcgggg agacggtgtc caccccactg agcagggaac   1440
aggcactgga cgtgcgcgac gccttcgtaa aggggatcta cgggcggctg ttcgtgtgga   1500
ttgtggacaa gatcaacgca gcaatttaca agcctccctc ccaggatgtg aagaactctc   1560
gcaggtccat cggcctcctg gacatctttg ggtttgagaa ctttgctgtg aacagctttg   1620
agcagctctg catcaacttc gccaatgagc acctgcagca gttctttgtg cggcacgtgt   1680
tcaagctgga gcaggaggaa tatgacctgg agagcattga ctggctgcac atcgagttca   1740
ctgacaacca ggatgccctg gacatgattg ccaacaagcc catgaacatc atctccctca   1800
tcgatgagga gagcaagttc cccaagggca cagacaccac catgttacac aagctgaact   1860
cccagcacaa gctcaacgcc aactacatcc cccccaagaa caaccatgag acccagtttg   1920
gcatcaacca ttttgcaggc atcgtctact atgagaccca aggcttcctg gagaagaacc   1980
gagacaccct gcatggggac attatccagc tggtccactc ctccaggaac aagttcatca   2040
agcagatctt ccaggccgat gtcgccatgg gcgccgagac caggaagcgc tcgcccacac   2100
ttagcagcca gttcaagcgg tcactggagc tgctgatgcg cacgctgggt gcctgccagc   2160
ccttctttgt gcgatgcatc aagcccaatg agttcaagaa gcccatgctg ttcgaccggc   2220
acctgtgcgt gcgccagctg cggtactcag gaatgatgga gaccatccga atccgccgag   2280
ctggctaccc catccgctac agcttcgtag agtttgtgga gcggtaccgt gtgctgctgc   2340
caggtgtgaa gccggcctac aagcagggcg acctccgcgg gacttgccag cgcatggctg   2400
```

```
aggctgtgct gggcacccac gatgactggc agataggcaa aaccaagatc tttctgaagg   2460
accaccatga catgctgctg gaagtggagc gggacaaagc catcaccgac agagtcatcc   2520
tccttcagaa agtcatccgg ggattcaaag acaggtctaa ctttctgaag ctgaagaacg   2580
ctgccacact gatccagagg cactggcggg gtcacaactg taggaagaac tacgggctga   2640
tgcgtctggg cttcctgcgg ctgcaggccc tgcaccgctc ccggaagctg caccagcagt   2700
accgcctggc ccgccagcgc atcatccagt tccaggcccg ctgccgcgcc tatctggtgc   2760
gcaaggcctt ccgccaccgc ctctgggctg tgctcaccgt gcaggcctat gcccggggca   2820
tgatcgcccg caggctgcac caacgcctca gggctgagta tctgtggcgc ctcgaggctg   2880
agaaaatgcg gctggcggag gaagagaagc ttcggaagga gatgagcgcc aagaaggcca   2940
aggaggaggc cgagcgcaag catcaggagc gcctggccca gctggctcgt gaggacgctg   3000
agcgggagct gaaggagaag gaggccgctc ggcggaagaa ggagctcctg gagcagatgg   3060
aaagggcccg ccatgagcct gtcaatcact cagacatggt ggacaagatg tttggcttcc   3120
tggggacttc aggtggcctg ccaggccagg agggccaggc acctagtggc tttgaggacc   3180
tggagcgagg gcggagggag atggtggagg aggacctgga tgcagccctg cccctgcctg   3240
acgaggatga ggaggacctc tctgagtata aatttgccaa gttcgcggcc acctacttcc   3300
aggggacaac cacgcactcc tacacccggc ggccactcaa acagccactg ctctaccatg   3360
acgacgaggg tgaccagctg gcagccctgg cggtctggat caccatcctc cgcttcatgg   3420
gggacctccc tgagcccaag taccacacag ccatgagtga tggcagtgag aagatccctg   3480
tgatgaccaa gatttatgag accctgggca agaagacgta caagagggag ctgcaggccc   3540
tgcagggcga gggcgaggcc cagctccccg agggccagaa gaagagcagt gtgaggcaca   3600
agctggtgca tttgactctg aaaaagaagt ccaagctcac agaggaggtg accaagaggc   3660
tgcatgacgg ggagtccaca gtgcagggca acagcatgct ggaggaccgg cccacctcca   3720
acctggagaa gctgcacttc atcatcggca atggcatcct gcggccagca ctccgggacg   3780
agatctactg ccagatcagc aagcagctga cccacaaccc ctccaagagc agctatgccc   3840
ggggctggat tctcgtgtct ctctgcgtgg gctgtttcgc cccctccgag aagtttgtca   3900
agtacctgcg gaacttcatc cacgggggcc cgcccggcta cgccccgtac tgtgaggagc   3960
gcctgagaag gacctttgtc aatgggacac ggacacagcc gcccagctgg ctggagctgc   4020
aggccaccaa gtccaagaag ccaatcatgt tgcccgtgac attcatggat gggaccacca   4080
agaccctgct gacggactcg gcaaccacgg ccaaggagct ctgcaacgcg ctggccgaca   4140
agatctctct caaggaccgg ttcgggttct ccctctacat tgccctgttt gacaaggtgt   4200
cctccctggg cagcggcagt gaccacgtca tggacgccat ctcccagtgc gagcagtacg   4260
ccaaggagca gggcgcccag gagcgcaacg ccccctggag gctcttcttc cgcaaagagg   4320
tcttcacgcc ctggcacagc cctccgagg acaacgtggc caccaacctc atctaccagc   4380
aggtggtgcg aggagtcaag tttggggagt acaggtgtga gaaggaggac gacctggctg   4440
agctggcctc ccagcagtac tttgtagact atggctctga gatgatcctg gagcgcctcc   4500
tgaacctcgt gcccacctac atccccgacc gcgagatcac gcccctgaag acgctggaga   4560
agtgggccca gctggccatc gccgcccaca agaaggggat ttatgcccag aggagaactg   4620
atgcccagaa ggtcaaagag gatgtggtca gttatgcccg cttcaagtgg cccttgctct   4680
tctccaggtt ttatgaagcc tacaaattct caggccccag tctccccaag aacgacgtca   4740
```

tcgtggccgt caactggacg ggtgtgtact ttgtggatga gcaggagcag gtacttctgg 4800
agctgtcctt cccagagatc atggccgtgt ccagcagcag ggagtgccgt gtctggctct 4860
cactgggctg ctctgatctt ggctgtgctg cgcctcactc aggctgggca ggactgaccc 4920
cggcggggcc ctgttctccg tgttggtcct gcaggggagc gaaaacgacg gcccccagct 4980
tcacgctggc caccatcaag gggacgaat acaccttcac ctccagtaat gctgaggaca 5040
ttcgtgacct ggtggtcacc ttcctagagg ggctccggaa gagatctaag tatgttgtgg 5100
ccctgcagga taaccccaac cccgcaggcg aggagtcagg cttcctcagc tttgccaagg 5160
gagacctcat catcctggac catgacacgg gcgagcaggt catgaactcg ggctgggcca 5220
acggcatcaa tgagaggacc aagcagcgtg gggacttccc caccgactgt gtgtacgtca 5280
tgcccactgt caccatgcca ccgcgggaga ttgtggccct ggtcaccatg actcccgatc 5340
agaggcagga cgttgtccgg ctcttgcagc tgcgaacggc ggagcccgag gtgcgtgcca 5400
agccctacac gctggaggag ttttcctatg actacttcag gcccccaccc aagcacacgc 5460
tgagccgtgt catggtgtcc aaggcccgag gcaaggaccg gctgtggagc cacacgcggg 5520
aaccgctcaa gcaggcgctg ctcaagaagc tcctgggcag tgaggagctc tcgcaggagg 5580
cctgcctggc cttcattgct gtgctcaagt acatgggcga ctacccgtcc aagaggacac 5640
gctccgtcaa cgagctcacc gaccagatct ttgagggtcc cctgaaagcc gagcccctga 5700
aggacgaggc atatgtgcag atcctgaagc agctgaccga caaccacatc aggtacagcg 5760
aggagcgggg ttgggagctg ctctggctgt gcacgggcct tttcccaccc agcaacatcc 5820
tcctgcccca cgtgcagcgc ttcctgcagt cccgaaagca ctgcccactc gccatcgact 5880
gcctgcaacg gctccagaaa gccctgagaa acgggtcccg gaagtaccct ccgcacctgg 5940
tggaggtgga ggccatccag cacaagacca cccagatttt ccacaaggtc tacttccctg 6000
atgacactga cgaggccttc gaagtggagt ccagcaccaa ggccaaggac ttctgccaga 6060
acatcgccac caggctgctc ctcaagtcct cagagggatt cagcctcttt gtcaaaattg 6120
cagacaaggt catcagcgtt cctgagaatg acttcttctt tgactttgtt cgacacttga 6180
cagactggat aaagaaagct cggcccatca aggacggaat tgtgccctca ctcacctacc 6240
aggtgttctt catgaagaag ctgtggacca ccacggtgcc agggaaggat cccatggccg 6300
attccatctt ccactattac caggagttgc ccaagtatct ccgaggctac cacaagtgca 6360
cgcgggagga ggtgctgcag ctgggggcgc tgatctacag ggtcaagttc gaggaggaca 6420
agtcctactt ccccagcatc cccaagctgc tgcgggagct ggtgccccag gaccttatcc 6480
ggcaggtctc acctgatgac tggaagcggt ccatcgtcgc ctacttcaac aagcacgcag 6540
ggaagtccaa ggaggaggcc aagctggcct tcctgaagct catcttcaag tggcccacct 6600
ttggctcagc cttcttcgag gtgaagcaaa ctacggagcc aaacttccct gagatcctcc 6660
taattgccat caacaagtat ggggtcagcc tcatcgatcc caaaacgaag gatatcctca 6720
ccactcatcc cttcaccaag atctccaact ggagcagcgg caacacctac ttccacatca 6780
ccattgggaa cttggtgcgc gggagcaaac tgctctgcga gacgtcactg ggctacaaga 6840
tggatgacct cctgacttcc tacattagcc agatgctcac agccatgagc aaacagcggg 6900
gctccaggag cggcaagtga acagtcacgg ggaggtgctg gttccatgcc tgctctcgag 6960
gcagcagtgg gttcaggccc atcagctacc cctgcagctg ggaagactt atgccatccc 7020
ggcagcgagg ctgggctggc cagccaccac tgactatacc aactgggcct ctgatgttct 7080
tccagtgagg catctctctg ggatgcagaa cttccctcca tccacccctc tggcacctgg 7140

-continued

```
gttggtctaa tcctagtttg ctgtggcctt cccggttgtg agagcctgtg atccttagat   7200

gtgtctcctg tttcagacca gccccaccat gcaacttcct ttgactttct gtgtaccact   7260

gggatagagg aatcaagagg acaatctagc tctccatact ttgaacaacc aaatgtgcat   7320

tgaatactct gaaaccgaag ggactggatc tgcaggtggg atgagggaga cagaccactt   7380

ttctatattg cagtgtgaat gctgggcccc tgctcaagtc taccctgatc acctcagggc   7440

ataaagcatg tttcattctc tgaaa                                         7465
```

<210> SEQ ID NO 6
<211> LENGTH: 2215
<212> TYPE: PRT
<213> ORGANISM: Homo sapiens

<400> SEQUENCE: 6

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
```

```
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735
```

Glu Val Glu Arg Asp Lys Ala Ile Thr Asp Arg Val Ile Leu Leu Gln
740 745 750

Lys Val Ile Arg Gly Phe Lys Asp Arg Ser Asn Phe Leu Lys Leu Lys
755 760 765

Asn Ala Ala Thr Leu Ile Gln Arg His Trp Arg Gly His Asn Cys Arg
770 775 780

Lys Asn Tyr Gly Leu Met Arg Leu Gly Phe Leu Arg Leu Gln Ala Leu
785 790 795 800

His Arg Ser Arg Lys Leu His Gln Gln Tyr Arg Leu Ala Arg Gln Arg
805 810 815

Ile Ile Gln Phe Gln Ala Arg Cys Arg Ala Tyr Leu Val Arg Lys Ala
820 825 830

Phe Arg His Arg Leu Trp Ala Val Leu Thr Val Gln Ala Tyr Ala Arg
835 840 845

Gly Met Ile Ala Arg Arg Leu His Gln Arg Leu Arg Ala Glu Tyr Leu
850 855 860

Trp Arg Leu Glu Ala Glu Lys Met Arg Leu Ala Glu Glu Glu Lys Leu
865 870 875 880

Arg Lys Glu Met Ser Ala Lys Lys Ala Lys Glu Glu Ala Glu Arg Lys
885 890 895

His Gln Glu Arg Leu Ala Gln Leu Ala Arg Glu Asp Ala Glu Arg Glu
900 905 910

Leu Lys Glu Lys Glu Ala Ala Arg Arg Lys Lys Glu Leu Leu Glu Gln
915 920 925

Met Glu Arg Ala Arg His Glu Pro Val Asn His Ser Asp Met Val Asp
930 935 940

Lys Met Phe Gly Phe Leu Gly Thr Ser Gly Gly Leu Pro Gly Gln Glu
945 950 955 960

Gly Gln Ala Pro Ser Gly Phe Glu Asp Leu Glu Arg Gly Arg Arg Glu
965 970 975

Met Val Glu Glu Asp Leu Asp Ala Ala Leu Pro Leu Pro Asp Glu Asp
980 985 990

Glu Glu Asp Leu Ser Glu Tyr Lys Phe Ala Lys Phe Ala Ala Thr Tyr
995 1000 1005

Phe Gln Gly Thr Thr Thr His Ser Tyr Thr Arg Arg Pro Leu Lys
1010 1015 1020

Gln Pro Leu Leu Tyr His Asp Asp Glu Gly Asp Gln Leu Ala Ala
1025 1030 1035

Leu Ala Val Trp Ile Thr Ile Leu Arg Phe Met Gly Asp Leu Pro
1040 1045 1050

Glu Pro Lys Tyr His Thr Ala Met Ser Asp Gly Ser Glu Lys Ile
1055 1060 1065

Pro Val Met Thr Lys Ile Tyr Glu Thr Leu Gly Lys Lys Thr Tyr
1070 1075 1080

Lys Arg Glu Leu Gln Ala Leu Gln Gly Glu Gly Glu Ala Gln Leu
1085 1090 1095

Pro Glu Gly Gln Lys Lys Ser Ser Val Arg His Lys Leu Val His
1100 1105 1110

Leu Thr Leu Lys Lys Lys Ser Lys Leu Thr Glu Glu Val Thr Lys
1115 1120 1125

Arg Leu His Asp Gly Glu Ser Thr Val Gln Gly Asn Ser Met Leu
1130 1135 1140

-continued

```
Glu Asp  Arg Pro Thr Ser Asn  Leu Glu Lys Leu His  Phe Ile Ile
    1145                 1150                 1155

Gly Asn  Gly Ile Leu Arg Pro  Ala Leu Arg Asp Glu  Ile Tyr Cys
    1160                 1165                 1170

Gln Ile  Ser Lys Gln Leu Thr  His Asn Pro Ser Lys  Ser Ser Tyr
    1175                 1180                 1185

Ala Arg  Gly Trp Ile Leu Val  Ser Leu Cys Val Gly  Cys Phe Ala
    1190                 1195                 1200

Pro Ser  Glu Lys Phe Val Lys  Tyr Leu Arg Asn Phe  Ile His Gly
    1205                 1210                 1215

Gly Pro  Pro Gly Tyr Ala Pro  Tyr Cys Glu Glu Arg  Leu Arg Arg
    1220                 1225                 1230

Thr Phe  Val Asn Gly Thr Arg  Thr Gln Pro Pro Ser  Trp Leu Glu
    1235                 1240                 1245

Leu Gln  Ala Thr Lys Ser Lys  Lys Pro Ile Met Leu  Pro Val Thr
    1250                 1255                 1260

Phe Met  Asp Gly Thr Thr Lys  Thr Leu Leu Thr Asp  Ser Ala Thr
    1265                 1270                 1275

Thr Ala  Lys Glu Leu Cys Asn  Ala Leu Ala Asp Lys  Ile Ser Leu
    1280                 1285                 1290

Lys Asp  Arg Phe Gly Phe Ser  Leu Tyr Ile Ala Leu  Phe Asp Lys
    1295                 1300                 1305

Val Ser  Ser Leu Gly Ser Gly  Ser Asp His Val Met  Asp Ala Ile
    1310                 1315                 1320

Ser Gln  Cys Glu Gln Tyr Ala  Lys Glu Gln Gly Ala  Gln Glu Arg
    1325                 1330                 1335

Asn Ala  Pro Trp Arg Leu Phe  Phe Arg Lys Glu Val  Phe Thr Pro
    1340                 1345                 1350

Trp His  Ser Pro Ser Glu Asp  Asn Val Ala Thr Asn  Leu Ile Tyr
    1355                 1360                 1365

Gln Gln  Val Val Arg Gly Val  Lys Phe Gly Glu Tyr  Arg Cys Glu
    1370                 1375                 1380

Lys Glu  Asp Asp Leu Ala Glu  Leu Ala Ser Gln Gln  Tyr Phe Val
    1385                 1390                 1395

Asp Tyr  Gly Ser Glu Met Ile  Leu Glu Arg Leu Leu  Asn Leu Val
    1400                 1405                 1410

Pro Thr  Tyr Ile Pro Asp Arg  Glu Ile Thr Pro Leu  Lys Thr Leu
    1415                 1420                 1425

Glu Lys  Trp Ala Gln Leu Ala  Ile Ala Ala His Lys  Lys Gly Ile
    1430                 1435                 1440

Tyr Ala  Gln Arg Arg Thr Asp  Ala Gln Lys Val Lys  Glu Asp Val
    1445                 1450                 1455

Val Ser  Tyr Ala Arg Phe Lys  Trp Pro Leu Leu Phe  Ser Arg Phe
    1460                 1465                 1470

Tyr Glu  Ala Tyr Lys Phe Ser  Gly Pro Ser Leu Pro  Lys Asn Asp
    1475                 1480                 1485

Val Ile  Val Ala Val Asn Trp  Thr Gly Val Tyr Phe  Val Asp Glu
    1490                 1495                 1500

Gln Glu  Gln Val Leu Leu Glu  Leu Ser Phe Pro Glu  Ile Met Ala
    1505                 1510                 1515

Val Ser  Ser Ser Arg Glu Cys  Arg Val Trp Leu Ser  Leu Gly Cys
    1520                 1525                 1530

Ser Asp  Leu Gly Cys Ala Ala  Pro His Ser Gly Trp  Ala Gly Leu
```

-continued 1535 1540 1545

Thr Pro Ala Gly Pro Cys Ser Pro Cys Trp Ser Cys Arg Gly Ala
1550 1555 1560

Lys Thr Thr Ala Pro Ser Phe Thr Leu Ala Thr Ile Lys Gly Asp
1565 1570 1575

Glu Tyr Thr Phe Thr Ser Ser Asn Ala Glu Asp Ile Arg Asp Leu
1580 1585 1590

Val Val Thr Phe Leu Glu Gly Leu Arg Lys Arg Ser Lys Tyr Val
1595 1600 1605

Val Ala Leu Gln Asp Asn Pro Asn Pro Ala Gly Glu Glu Ser Gly
1610 1615 1620

Phe Leu Ser Phe Ala Lys Gly Asp Leu Ile Ile Leu Asp His Asp
1625 1630 1635

Thr Gly Glu Gln Val Met Asn Ser Gly Trp Ala Asn Gly Ile Asn
1640 1645 1650

Glu Arg Thr Lys Gln Arg Gly Asp Phe Pro Thr Asp Cys Val Tyr
1655 1660 1665

Val Met Pro Thr Val Thr Met Pro Pro Arg Glu Ile Val Ala Leu
1670 1675 1680

Val Thr Met Thr Pro Asp Gln Arg Gln Asp Val Val Arg Leu Leu
1685 1690 1695

Gln Leu Arg Thr Ala Glu Pro Glu Val Arg Ala Lys Pro Tyr Thr
1700 1705 1710

Leu Glu Glu Phe Ser Tyr Asp Tyr Phe Arg Pro Pro Pro Lys His
1715 1720 1725

Thr Leu Ser Arg Val Met Val Ser Lys Ala Arg Gly Lys Asp Arg
1730 1735 1740

Leu Trp Ser His Thr Arg Glu Pro Leu Lys Gln Ala Leu Leu Lys
1745 1750 1755

Lys Leu Leu Gly Ser Glu Glu Leu Ser Gln Glu Ala Cys Leu Ala
1760 1765 1770

Phe Ile Ala Val Leu Lys Tyr Met Gly Asp Tyr Pro Ser Lys Arg
1775 1780 1785

Thr Arg Ser Val Asn Glu Leu Thr Asp Gln Ile Phe Glu Gly Pro
1790 1795 1800

Leu Lys Ala Glu Pro Leu Lys Asp Glu Ala Tyr Val Gln Ile Leu
1805 1810 1815

Lys Gln Leu Thr Asp Asn His Ile Arg Tyr Ser Glu Glu Arg Gly
1820 1825 1830

Trp Glu Leu Leu Trp Leu Cys Thr Gly Leu Phe Pro Pro Ser Asn
1835 1840 1845

Ile Leu Leu Pro His Val Gln Arg Phe Leu Gln Ser Arg Lys His
1850 1855 1860

Cys Pro Leu Ala Ile Asp Cys Leu Gln Arg Leu Gln Lys Ala Leu
1865 1870 1875

Arg Asn Gly Ser Arg Lys Tyr Pro Pro His Leu Val Glu Val Glu
1880 1885 1890

Ala Ile Gln His Lys Thr Thr Gln Ile Phe His Lys Val Tyr Phe
1895 1900 1905

Pro Asp Asp Thr Asp Glu Ala Phe Glu Val Glu Ser Ser Thr Lys
1910 1915 1920

Ala Lys Asp Phe Cys Gln Asn Ile Ala Thr Arg Leu Leu Leu Lys
1925 1930 1935

```
Ser Ser Glu Gly Phe Ser Leu Phe Val Lys Ile Ala Asp Lys Val
    1940                1945                1950

Ile Ser Val Pro Glu Asn Asp Phe Phe Phe Asp Phe Val Arg His
    1955                1960                1965

Leu Thr Asp Trp Ile Lys Lys Ala Arg Pro Ile Lys Asp Gly Ile
    1970                1975                1980

Val Pro Ser Leu Thr Tyr Gln Val Phe Phe Met Lys Lys Leu Trp
    1985                1990                1995

Thr Thr Thr Val Pro Gly Lys Asp Pro Met Ala Asp Ser Ile Phe
    2000                2005                2010

His Tyr Tyr Gln Glu Leu Pro Lys Tyr Leu Arg Gly Tyr His Lys
    2015                2020                2025

Cys Thr Arg Glu Glu Val Leu Gln Leu Gly Ala Leu Ile Tyr Arg
    2030                2035                2040

Val Lys Phe Glu Glu Asp Lys Ser Tyr Phe Pro Ser Ile Pro Lys
    2045                2050                2055

Leu Leu Arg Glu Leu Val Pro Gln Asp Leu Ile Arg Gln Val Ser
    2060                2065                2070

Pro Asp Asp Trp Lys Arg Ser Ile Val Ala Tyr Phe Asn Lys His
    2075                2080                2085

Ala Gly Lys Ser Lys Glu Glu Ala Lys Leu Ala Phe Leu Lys Leu
    2090                2095                2100

Ile Phe Lys Trp Pro Thr Phe Gly Ser Ala Phe Phe Glu Val Lys
    2105                2110                2115

Gln Thr Thr Glu Pro Asn Phe Pro Glu Ile Leu Leu Ile Ala Ile
    2120                2125                2130

Asn Lys Tyr Gly Val Ser Leu Ile Asp Pro Lys Thr Lys Asp Ile
    2135                2140                2145

Leu Thr Thr His Pro Phe Thr Lys Ile Ser Asn Trp Ser Ser Gly
    2150                2155                2160

Asn Thr Tyr Phe His Ile Thr Ile Gly Asn Leu Val Arg Gly Ser
    2165                2170                2175

Lys Leu Leu Cys Glu Thr Ser Leu Gly Tyr Lys Met Asp Asp Leu
    2180                2185                2190

Leu Thr Ser Tyr Ile Ser Gln Met Leu Thr Ala Met Ser Lys Gln
    2195                2200                2205

Arg Gly Ser Arg Ser Gly Lys
    2210                2215
```

```
<210> SEQ ID NO 7
<211> LENGTH: 6648
<212> TYPE: DNA
<213> ORGANISM: Homo sapiens

<400> SEQUENCE: 7

atggtgattc ttcagcaggg ggaccatgtg tggatggacc tgagattggg gcaggagttc      60

gacgtgccca tcggggcggt ggtgaagctc tgcgactctg ggcaggtcca ggtggtggat     120

gatgaagaca atgaacactg gatctctccg cagaacgcaa cgcacatcaa gcctatgcac     180

cccacgtcgg tccacggcgt ggaggacatg atccgcctgg gggacctcaa cgaggcgggc     240

atcttgcgca acctgcttat ccgctaccgg gaccacctca tctacacgta tacgggctcc     300

atcctggtgg ctgtgaaccc ctaccagctg ctctccatct actcgccaga gcacatccgc     360

cagtatacca acaagaagat tggggagatg cccccccaca tctttgccat tgctgacaac     420
```

```
tgctacttca acatgaaacg caacagccga gaccagtgct gcatcatcag tggggaatct    480
ggggccggga agacggagag cacaaagctg atcctgcagt tcctggcagc catcagtggg    540
cagcactcgt ggattgagca gcaggtcttg gaggccaccc ccattctgga agcatttggg    600
aatgccaaga ccatccgcaa tgacaactca agccgtttcg gaaagtacat cgacatccac    660
ttcaacaagc ggggcgccat cgagggcgcg aagattgagc agtacctgct ggaaaagtca    720
cgtgtctgtc gccaggccct ggatgaaagg aactaccacg tgttctactg catgctggag    780
ggtatgagtg aggatcagaa gaagaagctg ggcttgggcc aggcctctga ctacaactac    840
ttggccatgg gtaactgcat aacctgtgag ggccgggtgg acagccagga gtacgccaac    900
atccgctccg ccatgaaggt gctcatgttc actgacaccg agaactggga gatctcgaag    960
ctcctggctg ccatcctgca cctgggcaac ctgcagtatg aggcacgcac atttgaaaac   1020
ctggatgcct gtgaggttct cttctcccca tcgctggcca cagctgcatc cctgcttgag   1080
gtgaaccccc cagacctgat gagctgcctg actagccgca ccctcatcac ccgcggggag   1140
acggtgtcca ccccactgag cagggaacag gcactggacg tgcgcgacgc cttcgtaaag   1200
gggatctacg ggcggctgtt cgtgtggatt gtggacaaga tcaacgcagc aatttacaag   1260
cctccctccc aggatgtgaa gaactctcgc aggtccatcg gcctcctgga catctttggg   1320
tttgagaact ttgctgtgaa cagctttgag cagctctgca tcaacttcgc caatgagcac   1380
ctgcagcagt tctttgtgcg gcacgtgttc aagctggagc aggaggaata tgacctggag   1440
agcattgact ggctgcacat cgagttcact gacaaccagg atgccctgga catgattgcc   1500
aacaagccca tgaacatcat ctccctcatc gatgaggaga gcaagttccc caagggcaca   1560
gacaccacca tgttacacaa gctgaactcc cagcacaagc tcaacgccaa ctacatcccc   1620
cccaagaaca accatgagac ccagtttggc atcaaccatt ttgcaggcat cgtctactat   1680
gagacccaag gcttcctgga gaagaaccga gacaccctgc atggggacat tatccagctg   1740
gtccactcct ccaggaacaa gttcatcaag cagatcttcc aggccgatgt cgccatgggc   1800
gccgagacca ggaagcgctc gcccacactt agcagccagt tcaagcggtc actggagctg   1860
ctgatgcgca cgctgggtgc ctgccagccc ttctttgtgc gatgcatcaa gcccaatgag   1920
ttcaagaagc ccatgctgtt cgaccggcac ctgtgcgtgc gccagctgcg gtactcagga   1980
atgatggaga ccatccgaat ccgccgagct ggctacccca tccgctacag cttcgtagag   2040
tttgtggagc ggtaccgtgt gctgctgcca ggtgtgaagc cggcctacaa gcagggcgac   2100
ctccgcggga cttgccagcg catggctgag gctgtgctgg gcacccacga tgactggcag   2160
ataggcaaaa ccaagatctt tctgaaggac caccatgaca tgctgctgga agtggagcgg   2220
gacaaagcca tcaccgacag agtcatcctc cttcagaaag tcatccgggg attcaaagac   2280
aggtctaact ttctgaagct gaagaacgct gccacactga tccagaggca ctggcggggt   2340
cacaactgta ggaagaacta cgggctgatg cgtctgggct tcctgcggct gcaggccctg   2400
caccgctccc ggaagctgca ccagcagtac cgcctggccc gccagcgcat catccagttc   2460
caggcccgct gccgcgccta tctggtgcgc aaggccttcc gccaccgcct ctgggctgtg   2520
ctcaccgtgc aggcctatgc ccggggcatg atcgcccgca ggctgcacca acgcctcagg   2580
gctgagtatc tgtggcgcct cgaggctgag aaaatgcggc tggcggagga agagaagctt   2640
cggaaggaga tgagcgccaa gaaggccaag gaggaggccg agcgcaagca tcaggagcgc   2700
ctggcccagc tggctcgtga ggacgctgag cgggagctga aggagaagga ggccgctcgg   2760
```

-continued cggaagaagg agctcctgga gcagatggaa agggcccgcc atgagcctgt caatcactca 2820
gacatggtgg acaagatgtt tggcttcctg gggacttcag gtggcctgcc aggccaggag 2880
ggccaggcac ctagtggctt tgaggacctg gagcgagggc ggagggagat ggtggaggag 2940
gacctggatg cagccctgcc cctgcctgac gaggatgagg aggacctctc tgagtataaa 3000
tttgccaagt tcgcggccac ctacttccag gggacaacca cgcactccta cacccggcgg 3060
ccactcaaac agccactgct ctaccatgac gacgagggtg accagctggc agccctggcg 3120
gtctggatca ccatcctccg cttcatgggg gacctccctg agcccaagta ccacacagcc 3180
atgagtgatg gcagtgagaa gatccctgtg atgaccaaga tttatgagac cctgggcaag 3240
aagacgtaca agagggagct gcaggccctg cagggcgagg gcgaggccca gctccccgag 3300
ggccagaaga agagcagtgt gaggcacaag ctggtgcatt tgactctgaa aaagaagtcc 3360
aagctcacag aggaggtgac caagaggctg catgacgggg agtccacagt gcagggcaac 3420
agcatgctgg aggaccggcc cacctccaac ctggagaagc tgcacttcat catcggcaat 3480
ggcatcctgc ggccagcact ccgggacgag atctactgcc agatcagcaa gcagctgacc 3540
cacaacccct ccaagagcag ctatgcccgg ggctggattc tcgtgtctct ctgcgtgggc 3600
tgtttcgccc cctccgagaa gtttgtcaag tacctgcgga acttcatcca cgggggcccg 3660
cccggctacg ccccgtactg tgaggagcgc ctgagaagga cctttgtcaa tgggacacgg 3720
acacagccgc ccagctggct ggagctgcag gccaccaagt ccaagaagcc aatcatgttg 3780
cccgtgacat tcatggatgg gaccaccaag accctgctga cggactcggc aaccacggcc 3840
aaggagctct gcaacgcgct ggccgacaag atctctctca aggaccggtt cgggttctcc 3900
ctctacattg ccctgtttga caaggtgtcc tccctgggca gcggcagtga ccacgtcatg 3960
gacgccatct cccagtgcga gcagtacgcc aaggagcagg gcgcccagga gcgcaacgcc 4020
ccctggaggc tcttcttccg caaagaggtc ttcacgccct ggcacagccc ctccgaggac 4080
aacgtggcca ccaacctcat ctaccagcag gtggtgcgag gagtcaagtt tggggagtac 4140
aggtgtgaga aggaggacga cctggctgag ctggcctccc agcagtactt tgtagactat 4200
ggctctgaga tgatcctgga gcgcctcctg aacctcgtgc ccacctacat ccccgaccgc 4260
gagatcacgc ccctgaagac gctggagaag tgggcccagc tggccatcgc cgcccacaag 4320
aaggggattt atgcccagag gagaactgat gcccagaagg tcaaagagga tgtggtcagt 4380
tatgcccgct tcaagtggcc cttgctcttc tccaggtttt atgaagccta caaattctca 4440
ggccccagtc tccccaagaa cgacgtcatc gtggccgtca actggacggg tgtgtacttt 4500
gtggatgagc aggagcaggt acttctggag ctgtccttcc cagagatcat ggccgtgtcc 4560
agcagcaggg agtgccgtgt ctggctctca ctgggctgct ctgatcttgg ctgtgctgcg 4620
cctcactcag gctgggcagg actgaccccg gcggggccct gttctccgtg ttggtcctgc 4680
aggggagcga aaacgacggc ccccagcttc acgctggcca ccatcaaggg ggacgaatac 4740
accttcacct ccagtaatgc tgaggacatt cgtgacctgg tggtcacctt cctagagggg 4800
ctccggaaga gatctaagta tgttgtggcc ctgcaggata accccaaccc cgcaggcgag 4860
gagtcaggct tcctcagctt tgccaaggga gacctcatca tcctggacca tgacacgggc 4920
gagcaggtca tgaactcggg ctgggccaac ggcatcaatg agaggaccaa gcagcgtggg 4980
gacttcccca ccgactgtgt gtacgtcatg cccactgtca ccatgccacc gcgggagatt 5040
gtggccctgg tcaccatgac tcccgatcag aggcaggacg ttgtccggct cttgcagctg 5100
cgaacggcgg agcccgaggt gcgtgccaag ccctacacgc tggaggagtt ttcctatgac 5160

```
tacttcaggc ccccacccaa gcacacgctg agccgtgtca tggtgtccaa ggcccgaggc   5220

aaggaccggc tgtggagcca cacgcgggaa ccgctcaagc aggcgctgct caagaagctc   5280

ctgggcagtg aggagctctc gcaggaggcc tgcctggcct tcattgctgt gctcaagtac   5340

atgggcgact acccgtccaa gaggacacgc tccgtcaacg agctcaccga ccagatcttt   5400

gagggtcccc tgaaagccga gcccctgaag gacgaggcat atgtgcagat cctgaagcag   5460

ctgaccgaca accacatcag gtacagcgag gagcggggtt gggagctgct ctggctgtgc   5520

acgggccttt tcccacccag caacatcctc ctgccccacg tgcagcgctt cctgcagtcc   5580

cgaaagcact gcccactcgc catcgactgc ctgcaacggc tccagaaagc cctgagaaac   5640

gggtcccgga agtaccctcc gcacctggtg gaggtggagg ccatccagca caagaccacc   5700

cagattttcc acaaggtcta cttccctgat gacactgacg aggccttcga agtggagtcc   5760

agcaccaagg ccaaggactt ctgccagaac atcgccacca ggctgctcct caagtcctca   5820

gagggattca gcctctttgt caaaattgca gacaaggtca tcagcgttcc tgagaatgac   5880

ttcttctttg actttgttcg acacttgaca gactggataa agaaagctcg gcccatcaag   5940

gacggaattg tgccctcact cacctaccag gtgttcttca tgaagaagct gtggaccacc   6000

acggtgccag ggaaggatcc catggccgat tccatcttcc actattacca ggagttgccc   6060

aagtatctcc gaggctacca caagtgcacg cgggaggagg tgctgcagct gggggcgctg   6120

atctacaggg tcaagttcga ggaggacaag tcctacttcc ccagcatccc caagctgctg   6180

cgggagctgg tgccccagga ccttatccgg caggtctcac ctgatgactg gaagcggtcc   6240

atcgtcgcct acttcaacaa gcacgcaggg aagtccaagg aggaggccaa gctggccttc   6300

ctgaagctca tcttcaagtg gcccaccttt ggctcagcct tcttcgaggt gaagcaaact   6360

acggagccaa acttccctga gatcctccta attgccatca acaagtatgg ggtcagcctc   6420

atcgatccca aaacgaagga tatcctcacc actcatccct tcaccaagat ctccaactgg   6480

agcagcggca acacctactt ccacatcacc attgggaact tggtgcgcgg gagcaaactg   6540

ctctgcgaga cgtcactggg ctacaagatg gatgacctcc tgacttccta cattagccag   6600

atgctcacag ccatgagcaa acagcggggc tccaggagcg gcaagtga                6648
```

<210> SEQ ID NO 8
<211> LENGTH: 2175
<212> TYPE: PRT
<213> ORGANISM: Homo sapiens

<400> SEQUENCE: 8

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110
```

-continued

```
Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525
```

-continued

```
Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Lys Leu Lys
        755                 760                 765

Asn Ala Ala Thr Leu Ile Gln Arg His Trp Arg Gly His Asn Cys Arg
    770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
                805                 810                 815

Ile Ile Gln Phe Gln Ala Arg Cys Arg Ala Tyr Leu Val Arg Lys Ala
            820                 825                 830

Phe Arg His Arg Leu Trp Ala Val Leu Thr Val Gln Ala Tyr Ala Arg
        835                 840                 845

Gly Met Ile Ala Arg Arg Leu His Gln Arg Leu Arg Ala Glu Tyr Leu
    850                 855                 860

Trp Arg Leu Glu Ala Glu Lys Met Arg Leu Ala Glu Glu Glu Lys Leu
865                 870                 875                 880

Arg Lys Glu Met Ser Ala Lys Lys Ala Lys Glu Glu Ala Glu Arg Lys
                885                 890                 895

His Gln Glu Arg Leu Ala Gln Leu Ala Arg Glu Asp Ala Glu Arg Glu
            900                 905                 910

Leu Lys Glu Lys Glu Ala Ala Arg Arg Lys Lys Glu Leu Leu Glu Gln
        915                 920                 925

Met Glu Arg Ala Arg His Glu Pro Val Asn His Ser Asp Met Val Asp
    930                 935                 940

Lys Met Phe Gly Phe Leu Gly Thr Ser Gly Gly Leu Pro Gly Gln Glu
```

-continued

```
945                 950                 955                 960

Gly Gln Ala Pro Ser Gly Phe Glu Asp Leu Glu Arg Gly Arg Arg Glu
                965                 970                 975

Met Val Glu Glu Asp Leu Asp Ala Ala Leu Pro Leu Pro Asp Glu Asp
            980                 985                 990

Glu Glu Asp Leu Ser Glu Tyr Lys  Phe Ala Lys Phe Ala  Ala Thr Tyr
        995                 1000                1005

Phe Gln  Gly Thr Thr Thr His  Ser Tyr Thr Arg Arg  Pro Leu Lys
    1010                 1015                1020

Gln Pro  Leu Leu Tyr His Asp  Asp Glu Gly Asp Gln  Leu Ala Ala
    1025                 1030                1035

Leu Ala  Val Trp Ile Thr Ile  Leu Arg Phe Met Gly  Asp Leu Pro
    1040                 1045                1050

Glu Pro  Lys Tyr His Thr Ala  Met Ser Asp Gly Ser  Glu Lys Ile
    1055                 1060                1065

Pro Val  Met Thr Lys Ile Tyr  Glu Thr Leu Gly Lys  Lys Thr Tyr
    1070                 1075                1080

Lys Arg  Glu Leu Gln Ala Leu  Gln Gly Glu Gly Glu  Ala Gln Leu
    1085                 1090                1095

Pro Glu  Gly Gln Lys Lys Ser  Ser Val Arg His Lys  Leu Val His
    1100                 1105                1110

Leu Thr  Leu Lys Lys Lys Ser  Lys Leu Thr Glu Glu  Val Thr Lys
    1115                 1120                1125

Arg Leu  His Asp Gly Glu Ser  Thr Val Gln Gly Asn  Ser Met Leu
    1130                 1135                1140

Glu Asp  Arg Pro Thr Ser Asn  Leu Glu Lys Leu His  Phe Ile Ile
    1145                 1150                1155

Gly Asn  Gly Ile Leu Arg Pro  Ala Leu Arg Asp Glu  Ile Tyr Cys
    1160                 1165                1170

Gln Ile  Ser Lys Gln Leu Thr  His Asn Pro Ser Lys  Ser Ser Tyr
    1175                 1180                1185

Ala Arg  Gly Trp Ile Leu Val  Ser Leu Cys Val Gly  Cys Phe Ala
    1190                 1195                1200

Pro Ser  Glu Lys Phe Val Lys  Tyr Leu Arg Asn Phe  Ile His Gly
    1205                 1210                1215

Gly Pro  Pro Gly Tyr Ala Pro  Tyr Cys Glu Glu Arg  Leu Arg Arg
    1220                 1225                1230

Thr Phe  Val Asn Gly Thr Arg  Thr Gln Pro Pro Ser  Trp Leu Glu
    1235                 1240                1245

Leu Gln  Ala Thr Lys Ser Lys  Lys Pro Ile Met Leu  Pro Val Thr
    1250                 1255                1260

Phe Met  Asp Gly Thr Thr Lys  Thr Leu Leu Thr Asp  Ser Ala Thr
    1265                 1270                1275

Thr Ala  Lys Glu Leu Cys Asn  Ala Leu Ala Asp Lys  Ile Ser Leu
    1280                 1285                1290

Lys Asp  Arg Phe Gly Phe Ser  Leu Tyr Ile Ala Leu  Phe Asp Lys
    1295                 1300                1305

Val Ser  Ser Leu Gly Ser Gly  Ser Asp His Val Met  Asp Ala Ile
    1310                 1315                1320

Ser Gln  Cys Glu Gln Tyr Ala  Lys Glu Gln Gly Ala  Gln Glu Arg
    1325                 1330                1335

Asn Ala  Pro Trp Arg Leu Phe  Phe Arg Lys Glu Val  Phe Thr Pro
    1340                 1345                1350
```

-continued

```
Trp His  Ser Pro Ser Glu Asp  Asn Val Ala Thr Asn  Leu Ile Tyr
    1355                 1360                 1365

Gln Gln  Val Val Arg Gly Val  Lys Phe Gly Glu Tyr  Arg Cys Glu
    1370                 1375                 1380

Lys Glu  Asp Asp Leu Ala Glu  Leu Ala Ser Gln Gln  Tyr Phe Val
    1385                 1390                 1395

Asp Tyr  Gly Ser Glu Met Ile  Leu Glu Arg Leu Leu  Asn Leu Val
    1400                 1405                 1410

Pro Thr  Tyr Ile Pro Asp Arg  Glu Ile Thr Pro Leu  Lys Thr Leu
    1415                 1420                 1425

Glu Lys  Trp Ala Gln Leu Ala  Ile Ala Ala His Lys  Lys Gly Ile
    1430                 1435                 1440

Tyr Ala  Gln Arg Arg Thr Asp  Ala Gln Lys Val Lys  Glu Asp Val
    1445                 1450                 1455

Val Ser  Tyr Ala Arg Phe Lys  Trp Pro Leu Leu Phe  Ser Arg Phe
    1460                 1465                 1470

Tyr Glu  Ala Tyr Lys Phe Ser  Gly Pro Ser Leu Pro  Lys Asn Asp
    1475                 1480                 1485

Val Ile  Val Ala Val Asn Trp  Thr Gly Val Tyr Phe  Val Asp Glu
    1490                 1495                 1500

Gln Glu  Gln Val Leu Leu Glu  Leu Ser Phe Pro Glu  Ile Met Ala
    1505                 1510                 1515

Val Ser  Ser Ser Arg Gly Ala  Lys Thr Thr Ala Pro  Ser Phe Thr
    1520                 1525                 1530

Leu Ala  Thr Ile Lys Gly Asp  Glu Tyr Thr Phe Thr  Ser Ser Asn
    1535                 1540                 1545

Ala Glu  Asp Ile Arg Asp Leu  Val Val Thr Phe Leu  Glu Gly Leu
    1550                 1555                 1560

Arg Lys  Arg Ser Lys Tyr Val  Val Ala Leu Gln Asp  Asn Pro Asn
    1565                 1570                 1575

Pro Ala  Gly Glu Glu Ser Gly  Phe Leu Ser Phe Ala  Lys Gly Asp
    1580                 1585                 1590

Leu Ile  Ile Leu Asp His Asp  Thr Gly Glu Gln Val  Met Asn Ser
    1595                 1600                 1605

Gly Trp  Ala Asn Gly Ile Asn  Glu Arg Thr Lys Gln  Arg Gly Asp
    1610                 1615                 1620

Phe Pro  Thr Asp Ser Val Tyr  Val Met Pro Thr Val  Thr Met Pro
    1625                 1630                 1635

Pro Arg  Glu Ile Val Ala Leu  Val Thr Met Thr Pro  Asp Gln Arg
    1640                 1645                 1650

Gln Asp  Val Val Arg Leu Leu  Gln Leu Arg Thr Ala  Glu Pro Glu
    1655                 1660                 1665

Val Arg  Ala Lys Pro Tyr Thr  Leu Glu Glu Phe Ser  Tyr Asp Tyr
    1670                 1675                 1680

Phe Arg  Pro Pro Pro Lys His  Thr Leu Ser Arg Val  Met Val Ser
    1685                 1690                 1695

Lys Ala  Arg Gly Lys Asp Arg  Leu Trp Ser His Thr  Arg Glu Pro
    1700                 1705                 1710

Leu Lys  Gln Ala Leu Leu Lys  Lys Leu Leu Gly Ser  Glu Glu Leu
    1715                 1720                 1725

Ser Gln  Glu Ala Cys Leu Ala  Phe Ile Ala Val Leu  Lys Tyr Met
    1730                 1735                 1740
```

```
Gly Asp  Tyr Pro Ser Lys Arg  Thr Arg Ser Val Asn  Glu Leu Thr
    1745                 1750                 1755

Asp Gln  Ile Phe Glu Gly Pro  Leu Lys Ala Glu Pro  Leu Lys Asp
    1760                 1765                 1770

Glu Ala  Tyr Val Gln Ile Leu  Lys Gln Leu Thr Asp  Asn His Ile
    1775                 1780                 1785

Arg Tyr  Ser Glu Glu Arg Gly  Trp Glu Leu Leu Trp  Leu Cys Thr
    1790                 1795                 1800

Gly Leu  Phe Pro Pro Ser Asn  Ile Leu Leu Pro His  Val Gln Arg
    1805                 1810                 1815

Phe Leu  Gln Ser Arg Lys His  Cys Pro Leu Ala Ile  Asp Cys Leu
    1820                 1825                 1830

Gln Arg  Leu Gln Lys Ala Leu  Arg Asn Gly Ser Arg  Lys Tyr Pro
    1835                 1840                 1845

Pro His  Leu Val Glu Val Glu  Ala Ile Gln His Lys  Thr Thr Gln
    1850                 1855                 1860

Ile Phe  His Lys Val Tyr Phe  Pro Asp Asp Thr Asp  Glu Ala Phe
    1865                 1870                 1875

Glu Val  Glu Ser Ser Thr Lys  Ala Lys Asp Phe Cys  Gln Asn Ile
    1880                 1885                 1890

Ala Thr  Arg Leu Leu Leu Lys  Ser Ser Glu Gly Phe  Ser Leu Phe
    1895                 1900                 1905

Val Lys  Ile Ala Asp Lys Val  Leu Ser Val Pro Glu  Asn Asp Phe
    1910                 1915                 1920

Phe Phe  Asp Phe Val Arg His  Leu Thr Asp Trp Ile  Lys Lys Ala
    1925                 1930                 1935

Arg Pro  Ile Lys Asp Gly Ile  Val Pro Ser Leu Thr  Tyr Gln Val
    1940                 1945                 1950

Phe Phe  Met Lys Lys Leu Trp  Thr Thr Thr Val Pro  Gly Lys Asp
    1955                 1960                 1965

Pro Met  Ala Asp Ser Ile Phe  His Tyr Tyr Gln Glu  Leu Pro Lys
    1970                 1975                 1980

Tyr Leu  Arg Gly Tyr His Lys  Cys Thr Arg Glu Glu  Val Leu Gln
    1985                 1990                 1995

Leu Gly  Ala Leu Ile Tyr Arg  Val Lys Phe Glu Glu  Asp Lys Ser
    2000                 2005                 2010

Tyr Phe  Pro Ser Ile Pro Lys  Leu Leu Arg Glu Leu  Val Pro Gln
    2015                 2020                 2025

Asp Leu  Ile Arg Gln Val Ser  Pro Asp Asp Trp Lys  Arg Ser Ile
    2030                 2035                 2040

Val Ala  Tyr Phe Asn Lys His  Ala Gly Lys Ser Lys  Glu Glu Ala
    2045                 2050                 2055

Lys Leu  Ala Phe Leu Lys Leu  Ile Phe Lys Trp Pro  Thr Phe Gly
    2060                 2065                 2070

Ser Ala  Phe Phe Glu Gln Thr  Thr Glu Pro Asn Phe  Pro Glu Ile
    2075                 2080                 2085

Leu Leu  Ile Ala Ile Asn Lys  Tyr Gly Val Ser Leu  Ile Asp Pro
    2090                 2095                 2100

Lys Thr  Lys Asp Ile Leu Thr  Thr His Pro Phe Thr  Lys Ile Ser
    2105                 2110                 2115

Asn Trp  Ser Ser Gly Asn Thr  Tyr Phe His Ile Thr  Ile Gly Asn
    2120                 2125                 2130

Leu Val  Arg Gly Ser Lys Leu  Leu Cys Glu Thr Ser  Leu Gly Tyr
```

```
    2135                2140                2145

Lys Met  Asp Asp Leu Leu Thr  Ser Tyr Ile Ser Gln  Met Leu Thr
    2150                2155                2160

Ala Met  Ser Lys Gln Arg Gly  Ser Arg Ser Gly Lys
    2165                2170                2175


<210> SEQ ID NO 9
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 9

gcggcggccg ccaccatggt gattcttcag caggggac                              39


<210> SEQ ID NO 10
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 10

gcggctagcg aagttccgca ggtacttgac                                       30


<210> SEQ ID NO 11
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 11

gcgcttaagc aggtctaact ttctgaagct g                                     31


<210> SEQ ID NO 12
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 12

gcgggtacct cacttgccgc tcctggagcc                                       30


<210> SEQ ID NO 13
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 13

ggcacctagt ggctttgagg taagtatcaa ggttacaaga c                          41


<210> SEQ ID NO 14
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 14

gcggctagct cagaaacgca agagtcttc                                        29
```

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 15
cttctttgtg cgatgcatca ag 22

<210> SEQ ID NO 16
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 16
gcgcttaagc gacgcatgct cgcgatag 28

<210> SEQ ID NO 17
<211> LENGTH: 37
<212> TYPE: DNA
<213> ORGANISM: Artificial Sequence
<220> FEATURE:
<223> OTHER INFORMATION: Synthetic Oligonucleotide

<400> SEQUENCE: 17
cgccctcgct ccaggtcctg tggagagaaa ggcaaag 37

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
gaacccgaac cggtccttg 19

<210> SEQ ID NO 19
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 19
gcggctagcc cccgggtgcg cggcg 25

<210> SEQ ID NO 20
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 20
gcggtcgacg aaacggtcca ggctatgtg 29

<210> SEQ ID NO 21
<211> LENGTH: 27
<212> TYPE: DNA
<213> ORGANISM: Artificial Sequence
<220> FEATURE:

-continued

<223> OTHER INFORMATION: Synthetic Olligonucleotide

<400> SEQUENCE: 21
gcggcggccg cccccgggtg cgcggcg 27

<210> SEQ ID NO 22
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 22
gcgcttaagg aaacggtcca ggctatgtg 29

<210> SEQ ID NO 23
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 23
caggcaccta gtggctttga ggtaccaggc tagggacagg 40

<210> SEQ ID NO 24
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 24
gcggctagcc gcctgagccc agaagttc 28

<210> SEQ ID NO 25
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 25
cgccctcgct ccaggtcctg aaggagacaa gaggtatg 38

<210> SEQ ID NO 26
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 26
gcgcttaagc accgcttgtg ttgatcctc 29

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 27
gccagggaag gatcccatg 19

-continued

```
<210> SEQ ID NO 28
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 28

gcgggtacct catgcgtaat ccggtacatc gtaagggtac ttgccgctcc tggagcc        57


<210> SEQ ID NO 29
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 29

agcttcgtag agtttgtgga gcgg                                            24


<210> SEQ ID NO 30
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 30

gaggggcaaa caacagatg                                                  19
```